US012234265B2

(12) United States Patent
Zhang et al.

(10) Patent No.: US 12,234,265 B2
(45) Date of Patent: *Feb. 25, 2025

(54) STABILIZED RSV F PROTEINS AND USES THEREOF

(71) Applicant: Merck Sharp & Dohme LLC, Rahway, NJ (US)

(72) Inventors: Lan Zhang, Chalfont, PA (US); Arthur Fridman, Lake Ariel, PA (US); Eberhard Durr, Quakertown, PA (US); Andrew Bett, Lansdale, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 21 days.

This patent is subject to a terminal disclaimer.

(21) Appl. No.: 18/068,867

(22) Filed: Dec. 20, 2022

(65) Prior Publication Data

US 2023/0141153 A1 May 11, 2023

Related U.S. Application Data

(63) Continuation of application No. 16/964,118, filed as application No. PCT/US2019/014873 on Jan. 24, 2019, now Pat. No. 11,566,051.

(60) Provisional application No. 62/623,184, filed on Jan. 29, 2018.

(51) Int. Cl.
| | | |
|---|---|---|
| *C07K 14/135* | (2006.01) | |
| *A61K 39/155* | (2006.01) | |
| *C12N 7/00* | (2006.01) | |
| *A61K 39/00* | (2006.01) | |

(52) U.S. Cl.
CPC .......... *C07K 14/135* (2013.01); *A61K 39/155* (2013.01); *C12N 7/00* (2013.01); *A61K 2039/54* (2013.01); *A61K 2039/55505* (2013.01); *A61K 2039/55555* (2013.01); *C12N 2760/18534* (2013.01)

(58) Field of Classification Search
None
See application file for complete search history.

(56) References Cited

U.S. PATENT DOCUMENTS

| | | | |
|---|---|---|---|
| 2004/0096451 A1 | 5/2004 | Young et al. | |
| 2016/0361411 A1* | 12/2016 | Gindy | A61K 39/292 |
| 2018/0311336 A1 | 11/2018 | Ciaramella et al. | |

FOREIGN PATENT DOCUMENTS

| | | | |
|---|---|---|---|
| RU | 2012105308 A | 8/2013 | |
| WO | 2011008974 A2 | 1/2011 | |
| WO | 2014160463 A1 | 10/2014 | |
| WO | 2015130584 A2 | 9/2015 | |
| WO | 2017075124 A1 | 5/2017 | |
| WO | 2017109629 A1 | 6/2017 | |
| WO | WO-2017172890 A1 * | 10/2017 | A61K 39/12 |

OTHER PUBLICATIONS

U.S. Appl. No. 16/964,118, filed Jul. 22, 2020.
Anez, German et al., Passage of Dengue Virus Type 4 Vaccine Candidates in Fetal Rhesus Lung Cells Selects Heparin-Sensitive Variants That Result in Loss of Infectivity and Immunogenicity in Rhesus Macaques, Journal of Virology, 2009, 10384-10394, 83(20).
Chen, Xiaoying et al., Fusion Protein Linkers: Property, Design and Functionality, Adv. Drug Deliv. Rev., 2013, 1357-1369, 65.
Collins, Peter L., Nucleotide sequence of the gene encoding the fusion (F) glycoprotein of human respiratory syncytial virus, Proc. Natl. Acad. Sci. USA, 1984, 7683-7687, vol. 81, No. 24.
Flynn, Jessica A. et al., Stability Characterization of a Vaccine Antigen Based on the Respiratory Syncytial Virus Fusion Glycoprotein, PLoS One, 2016, 1-18, 11(10):e0164789.
Maeda, Yumi et al., Engineering of Functional Chimeric Protein G-Vargula Luciferase, Analytical Biochemistry, 1997, 147-152, 249.
Pakula, Andrew A., Genetic Analysis of Protein Stability and Function, Annu. Rev. Genet., 1989, 289-310, 23.
Tokuriki, Nobuhiko et al., Stability effects of mutations and protein evolvability, Curr Opin Structural Biol, 2009, 596-604, 19.
Zhang, Lan et al., Design and characterization of a fusion glycoprotein vaccine for Respiratory Syncytial Virus with Improved stability, Vaccine, 2018, 8119-8130, 36.

* cited by examiner

*Primary Examiner* — Shanon A. Foley
*Assistant Examiner* — Myron G Hill
(74) *Attorney, Agent, or Firm* — Nichole Martiak Valeyko; Emily Sauter

(57) ABSTRACT

The disclosure relates to stable RSV F proteins and immunogenic compositions containing the same, as well as methods of using the immunogenic compositions and compositions comprising the RSV F proteins.

11 Claims, 27 Drawing Sheets

Specification includes a Sequence Listing.

STABILIZED RSV F PROTEINS AND USES THEREOF

CROSS-REFERENCE TO RELATED APPLICATIONS

This application is a continuation of U.S. patent application Ser. No. 16/964,118, filed Jul. 22, 2020, which claims the benefit of International Application No. PCT/US2019/014873, filed Jan. 24, 2019, which claims the benefit of U.S. Provisional Application No. 62/632,184, filed Jan. 29, 2018, the contents of which are hereby incorporated by reference in their entirety.

FILED OF THE INVENTION

The present disclosure relates to stable RSV F proteins and immunogenic compositions containing the same, as well as methods of using the immunogenic compositions and compositions comprising the RSV F proteins.

REFERENCE TO SEQUENCE LISTING SUBMITTED ELECTRONICALLY

The instant application contains a Sequence Listing which has been submitted electronically in XML format and is hereby incorporated by reference in its entirety. The XML file, created on Dec. 7, 2022, is named 24566-US-CNT.XML and is 79 KB in size.

BACKGROUND OF INVENTION

Respiratory Syncytial Virus (RSV) is a member of the pneumovirus family. RSV infection is the leading cause of lower respiratory tract infection in both young children and older adults (>65 years). Currently, there is no licensed vaccine available, and therapeutic options are limited.

The envelope of RSV contains three surface glycoproteins: F, G, and SH. The G and F proteins are protective antigens and targets of neutralizing antibodies. The F protein, however, is more conserved across RSV strains and types (A and B). RSV F is a type I viral fusion protein which structurally rearranges from a metastable prefusion form to a highly stable postfusion form. Although targets for neutralizing monoclonal antibodies exist on the postfusion conformation of F protein, the neutralizing Ab response primarily targets the F protein prefusion conformation in people naturally infected with RSV (Magro M et al., *Proc Natl Acad Sci USA;* 109(8):3089-94, 2012; Ngwuta J O et al., *Sci Transl Med* 2015; 7(309):309ra162). Therefore, engineered RSV F protein stabilized in its prefusion conformation has been an attractive strategy for developing RSV F vaccine antigens. For example, a recombinant RSV F trimer including the "DS-Cav1" substitutions (155C, 290C, 190F, and 207L) was previously shown to elicit neutralizing immune response in animal models that is greater than the response observed for post-fusion F based RSV immunogens (McLellan et al., *Science,* 342: 592-598, 2013). Described herein are new RSV antigens which are even more stable in the prefusion form of interest.

SUMMARY OF INVENTION

The present disclosure provides a recombinant respiratory syncytial virus (RSV) F trimer, comprising: three recombinant RSV F peptides each comprising a deletion of RSV F wild type amino acids at positions 98-146 and a linker of eight to fourteen amino acids between RSV F wild type amino acid positions 97 and 147, wherein the recombinant F peptides comprise the following modifications to stabilize the recombinant RSV F trimer in a prefusion conformation: (i) 190F and 207L amino acid substitutions, (ii) 155C and 290C amino acid substitutions, and one (or more) of (a) 486C and 490C amino acid substitutions; (b) 180C and 186C amino acid substitutions; (c) 486C and 489C amino acid substitutions; (d) 512C and 513C amino acid substitutions; (e) an 505C amino acid substitution; and (f) a deletion of RSV F wild type amino acids 482-513. In one embodiment, each RSV F peptide further comprises at the C-terminus a deletion of the RSV F wild type transmembrane domain and cystoplasmic domain (for example, comprises at the c-terminus a deletion of RSV F wild type amino acids 525-574). In a further embodiment, each RSV F peptide comprises a deletion of RSV F wild type amino acids 514-574.

In one embodiment of the recombinant RSV F trimer, each of the recombinant F peptides further comprise a foldon sequence at the C-terminus of each peptide. In a further embodiment, the sequence of the foldon domain begins at the C-terminus of the peptide and replaces the RSV F wild type transmembrane domain and cytoplasmic domain (for example, the foldon domain replaces RSV F wild type amino acids 525-574). In a further embodiment, the sequence of the foldon domain begins after amino acid position 513 of wild type RSV F (i.e., the foldon sequence replaces amino acids 514-574 of wild type RSV-F). In another embodiment, when the RSV F peptides contain an additional deletion of amino acids 482-513 of wild type RSV F, the sequence of the foldon domain begins after amino acid position 481 of wild type RSV F (see, e.g., SEQ ID NO: 44). In some embodiments, the foldon sequence comprises SEQ ID NO: 8.

In one embodiment of the RSV F trimer, the recombinant F peptides each comprise the 190F and 207L amino acid substitutions, the 155C and 290C amino acid substitutions, the 486C and 490C amino acid substitutions, and the deletion of amino acids 514-574 of wild type RSV F. In one embodiment, each recombinant F peptide further comprises a non-native intra peptide disulfide bond between cysteines introduced by the 155C and 290C amino acid substitutions. In another embodiment, the RSV F trimer comprises one or more non-native inter peptide disulfide bond between cysteines introduced by the 486C and 490C amino acid substitutions. In a further embodiment, the C-terminus of the recombinant RSV F peptides each comprises a sequence of a foldon domain. In another embodiment, the sequence of the foldon domain comprises SEQ ID NO: 8.

In one embodiment of the RSV F trimer, the recombinant F peptides each comprise the 190F and 207L amino acid substitutions, the 155C and 290C amino acid substitutions, the 180C and 186C amino acid substitutions, and the deletion of amino acids 514-574 of wild type RSV F. In one embodiment, each recombinant RSV F peptide further comprises a non-native intra peptide disulfide bond between cysteines introduced by the 155C and 290C amino acid substitutions and/or a non-native intra peptide disulfide bond between cysteines introduced by the 190C and 186C amino acid substitutions. In a further embodiment, the C-terminus of the recombinant RSV F peptides each comprises a sequence of a foldon domain. In another embodiment, the sequence of the foldon domain comprises SEQ ID NO: 8.

In one embodiment of the recombinant RSV F trimer, the recombinant F peptides each comprise the 190F and 207L amino acid substitutions, the 155C and 290C amino acid substitutions, the 486C and 489C amino acid substitutions, and the deletion of amino acids 514-574 of wild type RSV F. In one embodiment, each recombinant RSV F peptide further comprises a non-native intra peptide disulfide bond between cysteines introduced by the 155C and 290C amino acid substitutions. In another embodiment, the RSV F trimer comprises a non-native inter-peptide disulfide bond between cysteines introduced by the 486C and 489C amino acid substitutions. In a further embodiment, the C-terminus of the recombinant RSV F peptides each comprises a sequence of a foldon domain. In another embodiment, the sequence of the foldon domain comprises SEQ ID NO: 8.

In one embodiment of the RSV trimer, the recombinant F peptides each comprise the 190F and 207L amino acid substitutions, the 155C and 290C amino acid substitutions, the 512C and 513C amino acid substitutions, and the deletion of amino acids 514-574 of wild type RSV F. In one embodiment, each recombinant RSV F peptide further comprises a non-native intra peptide disulfide bond between cysteines introduced by the 155C and 290C amino acid substitutions. In another embodiment, the RSV F trimer comprises a non-native inter-peptide disulfide bond between cysteines introduced by 512C and 513C amino acid substitutions. In a further embodiment, the C-terminus of the recombinant RSV F peptides each comprises a sequence of a foldon domain. In another embodiment, the sequence of the foldon domain comprises SEQ ID NO: 8.

In one embodiment of the recombinant RSV F trimer, the recombinant F peptides each comprise the 190F and 207L amino acid substitutions, the 155C and 290C amino acid substitutions, the 505C amino acid substitution, and the deletion of amino acids 514-574 of wild type RSV F. In another embodiment, each recombinant RSV F peptide further comprises a non-native intra peptide disulfide bond between cysteines introduced by the 155C and 290C amino acid substitutions. In a further embodiment, the C-terminus of the recombinant RSV F peptides each comprises a sequence of a foldon domain. In another embodiment, the sequence of the foldon domain comprises SEQ ID NO: 8.

In one embodiment of the recombinant RSV F trimer, the recombinant F peptides each comprise the 190F and 207L amino acid substitutions, the 155C and 290C amino acid substitutions and the deletion of amino acids 482-513 of wild type RSV F, as well as the deletion of amino acids 514-574 of wild type RSV F. In one embodiment, each recombinant RSV F peptide further comprises a non-native intra peptide disulfide bond between cysteines introduced by the 155C and 290C amino acid substitutions. In a further embodiment, the C-terminus of the recombinant RSV F peptides each comprises a sequence of a foldon domain. In another embodiment, the sequence of the foldon domain comprises SEQ ID NO: 8.

In one embodiment, the linker is eight (8), ten (10), twelve (12), or fourteen (14) amino acids in length. In one embodiment, the linker comprises the amino acid sequence set forth in SEQ ID NO: 46. In another embodiment, the linker has the amino acid sequence as set forth in any of SEQ ID NOS: 1, 2, 3, or 4.

In one embodiment, the recombinant F peptides of the RSV F trimer each comprise, consist essentially of, or consist of, the mature amino acid sequence as set forth in SEQ ID NO: 22. In one embodiment, the recombinant F peptides of the RSV F trimer each comprise, consist essentially of, or consist of, the mature amino acid sequence as set forth in SEQ ID NO: 24. In one embodiment, the recombinant F peptides of the RSV F trimer each comprise, consist essentially of, or consist of, the mature amino acid sequence as set forth in SEQ ID NO 26. In one embodiment, the recombinant F peptides of the RSV F trimer each comprise, consist essentially of, or consist of, the mature amino acid sequence as set forth in SEQ ID NO 28. In one embodiment, the recombinant F peptides of the RSV F trimer each comprise, consist essentially of, or consist of, the mature amino acid sequence as set forth in SEQ ID NO: 30. In one embodiment, the recombinant F peptides of the RSV F trimer each comprise, consist essentially of, or consist of, the mature amino acid sequence as set forth in SEQ ID NO: 44.

The present disclosure also provides an RSV immunogenic composition comprising a recombinant respiratory syncytial virus (RSV) F trimer, comprising: three recombinant RSV F peptides each comprising a deletion of RSV F wild type amino acids at positions 98-146 and a linker of eight to fourteen amino acids between RSV F wild type amino acid positions 97 and 147, wherein the recombinant F peptides comprise the following modifications to stabilize the recombinant RSV F trimer in a prefusion conformation: (i) 190F and 207L amino acid substitutions, (ii) 155C and 290C amino acid substitutions, and one (or more) of (a) 486C and 490C amino acid substitutions; (b) 180C and 186C amino acid substitutions; (c) 486C and 489C amino acid substitutions; (d) 512C and 513C amino acid substitutions; (e) an 505C amino acid substitution; and (f) a deletion of RSV F wild type amino acids 482-513. In one embodiment, each RSV F peptide further comprises at the C-terminus a deletion of the RSV F wild type transmembrane domain and cystoplasmic domain (for example, comprises at the c-terminus a deletion of RSV F wild type amino acids 525-574). In a further embodiment, each RSV F peptide comprises a deletion of RSV F wild type amino acids 514-574.

In one embodiment of the immunogenic composition, each of the recombinant F peptides further comprise a foldon sequence at the C-terminus of each peptide. In a further embodiment, the sequence of the foldon domain begins after amino acid position 513 of wild type RSV F (i.e., the foldon sequence replaces amino acids 514-574 of wild type RSV-F). In another embodiment, when the RSV F peptides contain an additional deletion of amino acids 482-513 of wild type RSV F, the sequence of the foldon domain begins after amino acid position 481 of wild type RSV F (see, e.g., SEQ ID NO: 44). In some embodiments, the foldon sequence comprises SEQ ID NO: 8.

In one embodiment of the immunogenic composition, the RSV F trimer is any of the RSV trimers described herein. In another embodiment of the immunogenic composition, the recombinant F peptides of the RSV F trimer each comprise, consist essentially of, or consist of, the mature amino acid sequence as set forth in any of SEQ ID NO: 22, 24, 26, 28, 30 and 44.

The present disclosure also provides an RSV peptide which comprises a deletion of RSV F wild type amino acids at positions 98-146 and a linker of eight to fourteen amino acids between RSV F wild type positions 97 and 147, and additional modifications to stabilize a recombinant RSV F trimer containing three of such recombinant RSV peptides in the prefusion conformation. Such additional modifications in the single chain RSV peptide comprise: (i) 190F and 207L amino acid substitutions, (ii) 155C and 290C amino acid substitutions, and one (or more) of (a) 486C and 490C amino acid substitutions; (b) 180C and 186C amino acid substitutions; (c) 486C and 489C amino acid substitutions; (d) 512C and 513C amino acid substitutions; (e) an 505C amino acid substitution; and (f) a deletion of RSV F wild type amino acids 482-513. In one embodiment, the RSV F peptide further comprises at the C-terminus a deletion of the RSV F wild type transmembrane domain and cystoplasmic domain (for example, comprises at the c-terminus a deletion of RSV F wild type amino acids 525-574). In a further embodiment, the RSV F peptide comprises a deletion of RSV F wild type amino acids 514-574.

In one embodiment, the RSV F peptide further comprises a foldon sequence at the C-terminus. In a further embodiment, the sequence of the foldon domain begins after amino acid position 513 of wild type RSV F (i.e., the foldon sequence replaces amino acids 514-574 of wild type RSV-F). In another embodiment, when the RSV F peptide contains an additional deletion of amino acids 482-513 of wild type RSV F, the sequence of the foldon domain begins after amino acid position 482 of wild type RSV F (see, e.g., SEQ ID NO: 44). In some embodiments, the foldon sequence comprises SEQ ID NO: 8.

In one embodiment, the RSV F peptide comprises the 190F and 207L amino acid substitutions, the 155C and 290C amino acid substitutions, the 486C and 490C amino acid substitutions, and the deletion of amino acids 514-574 of wild type RSV F. In one embodiment, the RSV F peptide further comprises a non-native intra peptide disulfide bond between cysteines introduced by the 155C and 290C amino acid substitutions. In a further embodiment, the C-terminus of the RSV F peptide comprises a sequence of a foldon domain. In another embodiment, the sequence of the foldon domain comprises SEQ ID NO: 8.

In one embodiment, the RSV F peptide comprises the 190F and 207L amino acid substitutions, the 155C and 290C amino acid substitutions, the 180C and 186C amino acid substitutions, and the deletion of amino acids 514-574 of wild type RSV F. In one embodiment, the RSV F peptide further comprises a non-native intra peptide disulfide bond between cysteines introduced by the 155C and 290C amino acid substitutions and/or a non-native intra peptide disulfide bond between cysteines introduced by the 190C and 186C amino acid substitutions. In a further embodiment, the C-terminus of the RSV F peptide comprises a sequence of a foldon domain. In another embodiment, the sequence of the foldon domain comprises SEQ ID NO: 8.

In one embodiment, the RSV F peptide comprises the 190F and 207L amino acid substitutions, the 155C and 290C amino acid substitutions, the 486C and 489C amino acid substitutions, and the deletion of amino acids 514-574 of wild type RSV F. In one embodiment, the RSV F peptide further comprises a non-native intra peptide disulfide bond between cysteines introduced by the 155C and 290C amino acid substitutions. In a further embodiment, the C-terminus of the RSV F peptide comprises a sequence of a foldon domain. In another embodiment, the sequence of the foldon domain comprises SEQ ID NO: 8.

In one embodiment, the RSV F peptide comprises the 190F and 207L amino acid substitutions, the 155C and 290C amino acid substitutions, the 512C and 513C amino acid substitutions, and the deletion of amino acids 514-574 of wild type RSV F. In one embodiment, the RSV F peptide further comprises a non-native intra peptide disulfide bond between cysteines introduced by the 155C and 290C amino acid substitutions. In a further embodiment, the C-terminus of the RSV F peptide comprises a sequence of a foldon domain. In another embodiment, the sequence of the foldon domain comprises SEQ ID NO: 8.

In one embodiment, the RSV F peptide comprises the 190F and 207L amino acid substitutions, the 155C and 290C amino acid substitutions, the 505C amino acid substitution, and the deletion of amino acids 514-574 of wild type RSV F. In another embodiment, the RSV F peptide further comprises a non-native intra peptide disulfide bond between cysteines introduced by the 155C and 290C amino acid substitutions. In a further embodiment, the C-terminus of the RSV F peptide comprises a sequence of a foldon domain. In another embodiment, the sequence of the foldon domain comprises SEQ ID NO: 8.

In one embodiment, the RSV F peptide comprises the 190F and 207L amino acid substitutions, the 155C and 290C amino acid substitutions and the deletion of amino acids 482-513 of wild type RSV F, as well as the deletion of amino acids 514-574 of wild type RSV F. In one embodiment, the RSV F peptide further comprises a non-native intra peptide disulfide bond between cysteines introduced by the 155C and 290C amino acid substitutions. In a further embodiment, the C-terminus of the RSV F peptides each comprises a sequence of a foldon domain. In another embodiment, the sequence of the foldon domain comprises SEQ ID NO: 8.

In one embodiment, the linker is eight (8), ten (10), twelve (12), or fourteen (14) amino acids in length. In one embodiment, the linker comprises the amino acid sequence set forth in SEQ ID NO: 46. In another embodiment, the linker has the amino acid sequence as set forth in any of SEQ ID NOS: 1, 2, 3, or 4.

In one embodiment, the RSV F peptide comprises, consists essentially of, or consists of, the mature amino acid sequence as set forth in SEQ ID NO: 22. In one embodiment, the RSV F peptide comprises, consists essentially of, or consists of, the mature amino acid sequence as set forth in SEQ ID NO: 24. In one embodiment, the RSV F peptides comprises, consists essentially of, or consists of, the mature amino acid sequence as set forth in SEQ ID NO 26. In one embodiment, the RSV F peptide comprises, consists essentially of, or consists of, the mature amino acid sequence as set forth in SEQ ID NO 28. In one embodiment, the RSV F peptide comprises, consists essentially of, or consists of, the mature amino acid sequence as set forth in SEQ ID NO: 30. In one embodiment, the RSV F peptide comprises, consists essentially of, or consists of, the mature amino acid sequence as set forth in SEQ ID NO: 44.

In one embodiment, the RSV peptide, when produced recombinantly, forms an RSV F trimer, as described herein.

The present disclosure also provides for an isolated nucleic acid molecule encoding a single chain RSV peptide as described herein. In one embodiment, the isolated nucleic acid molecule is a DNA molecule. The present disclosure further provides for a vector comprising said nucleic acid molecule.

The present disclosure also provides a method of making a recombinant respiratory syncytial virus (RSV) F trimer as described herein, said method comprising (i) expressing the nucleic acid molecule, or the vector, each described above, and (ii) purifying a recombinant RSV F trimer produced therefrom.

The present disclosure also provides antibody molecules, including full length antibodies and antibody derivatives, directed against the RSV F trimer described herein, or against the RSV F peptides described herein.

In some embodiments, the immunogenic composition is formulated with an adjuvant. In one embodiment, the adjuvant is an aluminum adjuvant. In some embodiments, the aluminum adjuvant is MAA or MAPA.

In some embodiments, the recombinant RSV F trimer or RSV F peptides, each described herein, is formulated with a lipid nanoparticle (LNP) comprising a cationic lipid, a PEG-modified lipid, a sterol, and a non-cationic lipid.

Some embodiments of the present disclosure provide methods of an RSV F specific immune response in a subject, comprising administering to the subject any of the immunogenic compositions described herein, or the recombinant RSV F trimers as described herein, in an amount effective to produce an RSV F specific immune response. In some embodiments, the antigen-specific immune response comprises a T cell response or a B cell response.

In some embodiments, the method comprises administering to a subject a single dose (no booster dose) of an immunogenic composition, or an RSV F trimer, as described herein. In another embodiment, the method further comprises administering to the subject a second (booster) dose of an immunogenic composition, or an RSV F trimer, as described herein. In another embodiment, the method further comprises administering at least one booster dose of the RSV F trimer or RSV immunogenic composition. Additional doses may be administered.

In some embodiments, the RSV immunogenic composition, or RSV F trimer, is administered to a subject by intradermal injection, intramuscular injection, or by intranasal administration. In some embodiments, an RSV vaccine is administered to a subject by intramuscular injection.

In some embodiments, the RSV F trimer, or immunogenic composition, immunizes the subject against RSV for up to 1 or 2 years. In some embodiments, the RSV F trimer, or immunogenic composition, immunizes the subject against RSV for more than 2 years, more than 3 years, more than 4 years, or for 5-10 years. In one embodiment, the immunogenic composition is administered as a vaccine yearly.

In some embodiments, the subject is about 5 years old or younger. For example, the subject may be between the ages of about 1 year and about 5 years (e.g., about 1, 2, 3, 4 or 5 years), or between the ages of about 6 months and about 1 year (e.g., about 6, 7, 8, 9, 10, 11 or 12 months). In some embodiments, the subject is about 12 months or younger (e.g., 12, 11, 10, 9, 8, 7, 6, 5, 4, 3, 2 months or 1 month). In some embodiments, the subject is about 6 months or younger.

In some embodiments, the subject was born full term (e.g., about 37-42 weeks). In some embodiments, the subject was born prematurely, for example, at about 36 weeks of gestation or earlier (e.g., about 36, 35, 34, 33, 32, 31, 30, 29, 28, 27, 26 or 25 weeks). For example, the subject may have been born at about 32 weeks of gestation or earlier. In some embodiments, the subject was born prematurely between about 32 weeks and about 36 weeks of gestation. In such subjects, a vaccine may be administered later in life, for example, at the age of about 6 months to about 5 years, or older.

In some embodiments, the subject is a young adult between the ages of about 20 years and about 50 years (e.g., about 20, 25, 30, 35, 40, 45 or 50 years old).

In some embodiments, the subject is an elderly subject about 50-60 years old, 60 years old, about 70 years old, or older, 80 years or older, 90 years or older (e.g., about 60, 65, 70, 75, 80, 85 or 90 years old). In some embodiments, the subject is immunocompromised (e.g., has an immune disorder or autoimmune disorder).

In some embodiments, the subject is pregnant when administered the RSV immunogenic composition. In some embodiments, the subject has a chronic pulmonary disease, such as chronic obstructive pulmonary disease (COPD) or asthma.

In some embodiments, the subject has been exposed to RSV, is infective with (has) RSV, or is at risk of infection by RSV.

The details of various embodiments of the disclosure are set forth in the description below. Other features, objects, and advantages of the disclosure will be apparent from the description and from the claims.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIGS. 2A, 2B, and 2C, respectively) or those stored at 4° C. for 7 days (FIGS. 2D, 2E, and 2F, respectively) to D25 and Synagis® (palivizumab).

FIG. 16A is high dose immunization. FIG. 16 B is low dose immunization. FIG. 16 C shows the area under the curve.

FIG. 17A is high dose immunization. FIG. 17 B is low dose immunization. FIG. 17 C shows the area under the curve.

DETAILED DESCRIPTION

Figure 1A:
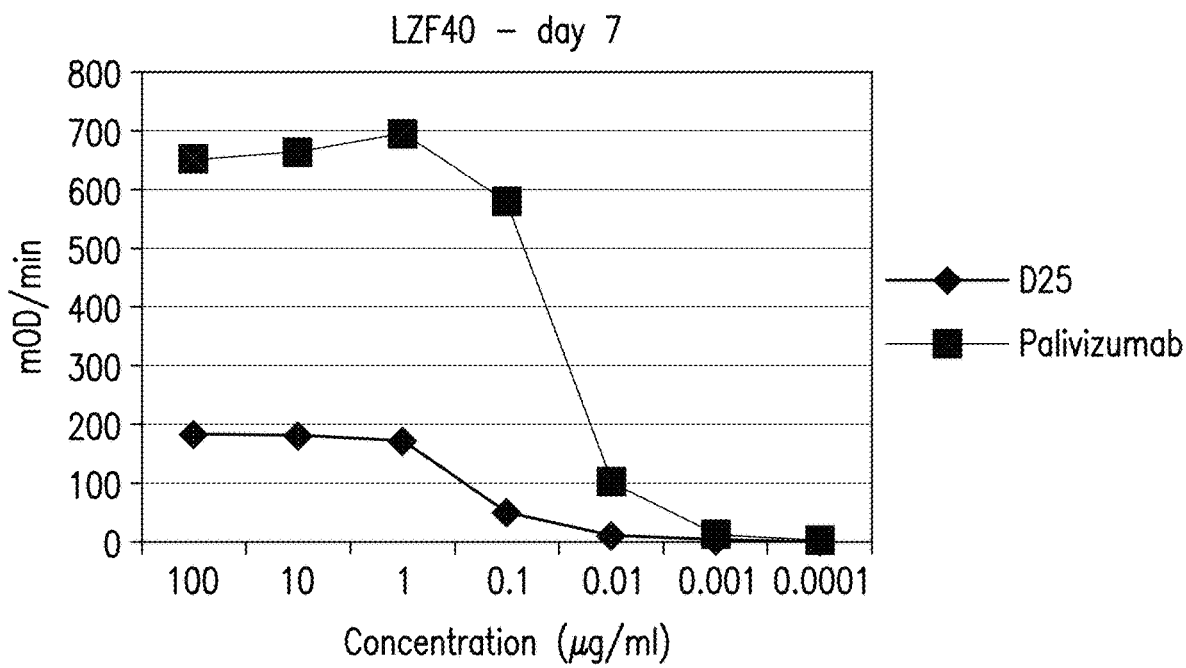
FIGS. 1A and 1B show binding of freshly harvested day 7 post-transfection cell culture supernatants (supe) of LZF40 (DS-Cav1 with an 8 a.a. linker) (FIG. 1A) or those stored at 4° C. for 8 days (FIG. 1B) to D25 and Synagis® (palivizumab) monoclonal antibodies.

RSV F protein is a type I fusion glycoprotein that is well conserved between clinical isolates, including between the RSV-A and RSV-B antigenic subgroups. The F protein transitions between prefusion and more stable postfusion states, thereby facilitating entry into target cells. RSV F glycoprotein is initially synthesized as an $F_0$ precursor protein. RSV $F_0$ folds into a trimer, which is activated by furin cleavage into the mature prefusion protein comprising F1 and F2 subunits (Bolt, et al., Virus Res., 68:25, 2000). RSV F protein stabilized in the prefusion conformation produces a greater neutralizing immune response in animal models than that observed with RSV F protein stabilized in the post fusion conformation (McLellan et al., *Science,* 342: 592-598, 2013). As such, stabilized prefusion RSV F proteins are good candidates for inclusion in an RSV vaccine. Soluble RSV ectodomains stabilized in the prefusion conformation have previously been generated, including the "DS-Cav1" substitutions. See, WO 2014/160463A1 and WO 2017/172890A1, the contents of each of which are hereby incorporated by reference.

It has been previously shown that the prefusion stabilized RSV F construct, DS-Cav1, undergoes conformational changes and forms intermediate structures upon long-term storage at 4° C. (Flynn J A et al., *PLoS ONE* 2016; 11(10): e0164789). Long term stability at 4° C. or higher is a desirable attribute for an RSV F subunit vaccine antigen. Described herein are additional structure-based modifications to further improve the stability of the RSV F trimer in the prefusion conformation. Such constructs have increased stability at 4° C. as compared to DS-Cav1 while retaining immunogenicity.

"RSV Fusion Protein" and "RSV F protein", each as used herein refers to an RSV envelope glycoprotein that facilitates fusion of viral and cellular membranes. In nature, the RSV F protein is synthesized into a single polypeptide precursor designated $F_0$, which includes a signal peptide that directs localization to the endoplasmic reticulum, where the signal peptide is cleaved. The remaining $F_0$ residues oligomerize to form a trimer and are proteolytically processed by a protease at two conserved furin cleavage sequences to generate two disulfide linked fragments, $F_1$ and F2. In nature, three $F_2$-$F_1$ peptides oligomerize into a trimer to form the mature F protein, which adopts a prefusion conformation that is metastable and can undergo a conformation change to a postfusion conformation.

"RSV F transmembrane domain" corresponds to the transmembrane domain of wild type RSV F (i.e., amino acids 525-550 of SEQ ID NO: 10).

"RSV F cytoplasmic domain" or "RSV F cytoplasmic tail" corresponds to the cytoplasmic tail domain of wild type RSV F (i.e., amino acid 551-574 of SEQ ID NO: 10).

"D25" or "D25 antibody" as used herein describes a neutralizing antibody that specifically binds to prefusion RSV F peptides. This antibody is described in U.S. Patent Application Publication No. US 2010/0239593, the entire content of which is hereby incorporated by reference.

"Single chain RSV mutants" refer to an RSV F protein that has been modified so that it does not include the furin cleavage sites such that when a single chain RSV mutant is produced in cells, the $F_0$ peptide is not cleaved into separate $F_1$ and $F_2$ chains. A non-limiting example of a single chain RSV mutant includes position 97 of the $F_2$ polypeptide linked to position 97 to position 147 of the $F_1$ peptide by a flexible linker to generate the single chain RSV mutant.

"DS-Cav1"; "DS-Cav1 substitutions", each as used herein, refer to genetic modifications to the RSV F protein, which contains the "DS" substitutions 155C and 290C so as to introduce a non-native disulfide bond between cysteines introduced by the substitutions (such as S155C and S290C substitutions) and the "Cav1" substitutions, which include 190F and 207L cavity filling amino acid substitutions (such as S190F and V207L). DS-Cav1 is described in WO 2014/160463, the entire contents of which are hereby incorporated by reference.

"Foldon domain" or "foldon", each as used herein, refers to a T4 fibritin trimerization domain that comprises an amino acid sequence that naturally forms a trimeric structure. In some examples, the sequence of the RSV F protein is modified to contain a foldon domain. In other examples, the single chain RSV mutants contain a foldon domain. An example of a foldon trimerization domain comprises the amino acid sequence as set forth in SEQ ID NO: 8.

As used herein, a "signal peptide" or "signal sequence" are short amino acid sequences that direct newly synthesized secretory or membrane proteins to and through membranes, and thus universally control the entry of most proteins both in eukaryotes and prokaryotes to the secretory pathway. Endoplasmic reticulum processing produces mature proteins, wherein the signal peptide is cleaved from the precursor proteins. As referred to herein, the "mature amino acid sequence" does not contain the signal peptide. The mature amino acid sequence of the single chain RSV mutants does not contain a signal peptide. In addition, the RSV trimer which is comprised of three mature single chain RSV mutants does not contain the signal peptide sequence.

As used herein, the term "substitution", "amino acid substitution," or" substitutional variant" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more (e.g., 3, 4 or 5) amino acids have been substituted in the same molecule. For example, as used herein, reference to a "155C" substitution in an RSV F protein or single chain RSV F mutant refers to the single chain RSV F protein having a cysteine residue at position 155, which cysteine residue has been substituted for the corresponding native residue at position 155 in the RSV F protein. By way of reference, SEQ ID NO: 10 is a reference sequence with regard to the location of the substitution. For example, a "S155C" substitution is a substitution of the S at position 155 of SEQ ID NO: 10 with at a C.

"Isolated" polypeptides or polynucleotides are at least partially free of other biological molecules from the cells or cell cultures in which they are produced. Such biological molecules include other nucleic acids, proteins, lipids, carbohydrates, or other material such as cellular debris and growth medium. It may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the polypeptides or polynucleotides.

A "polypeptide variant" is a molecule that differs in its amino acid sequence relative to a native sequence or a reference sequence. Amino acid sequence variants may possess substitutions, deletions, insertions, or a combination of any two or three of the foregoing, at certain positions within the amino acid sequence, as compared to a native sequence or a reference sequence. Ordinarily, variants possess at least 50% identity to a native sequence or a reference sequence. In some embodiments, variants share at least 80% identity or at least 90% identity with a native sequence or a reference sequence.

"Analogs" is meant to include polypeptide variants that differ by one or more amino acid alterations, for example, substitutions, additions, or deletions of amino acid residues that still maintain one or more of the properties of the parent or starting polypeptide.

The present disclosure provides several types of compositions that are polynucleotide or polypeptide based, including variants and derivatives. These include, for example, substitutional, insertional, deletion and covalent variants and derivatives. The term "derivative" is synonymous with the term "variant" and generally refers to a molecule that has been modified and/or changed in any way relative to a reference molecule or a starting molecule.

As such, polynucleotides encoding peptides or polypeptides containing substitutions, insertions and/or additions, deletions, and covalent modifications with respect to reference sequences, in particular the polypeptide sequences disclosed herein, are included within the scope of this disclosure. For example, sequence tags or amino acids, such as one or more lysines, can be added to peptide sequences (e.g., at the N-terminal or C-terminal end). Sequence tags can be used for peptide detection, purification, or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal residues or N-terminal residues) alternatively may be deleted depending on the use of the sequence, as for example, expression of the sequence as part of a larger sequence that is soluble or linked to a solid support.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides the terms "site" as it pertains to amino acid-based embodiments is used synonymously with "amino acid residue" and "amino acid side chain." As used herein when referring to polynucleotides the terms "site" as it pertains to nucleotide-based embodiments is used synonymously with "nucleotide." A site represents a position within a peptide or polypeptide or polynucleotide that may be modified, manipulated, altered, derivatized or varied within the polypeptide-based or polynucleotide-based molecules.

As used herein the terms "termini" or "terminus" when referring to polypeptides or polynucleotides refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide-based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein having a length of 10, 20, 30, 40, 50, 60, 70, 80, 90, 100 or longer than 100 amino acids. In another example, any protein that includes a stretch of 20, 30, 40, 50, or 100 (contiguous) amino acids that are 40%, 50%, 60%, 70%, 80%, 90%, 95%, 96%, 97%, 98%, 99% or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided herein or referenced herein. In another example, any protein that includes a stretch of 20, 30, 40, 50, or 100 amino acids that are greater than 80%, 90%, 95%, or 100% identical to any of the sequences described herein, wherein the protein has a stretch of 5, 10, 15, 20, 25, or 30 amino acids that are less than 80%, 75%, 70%, 65% to 60% identical to any of the sequences described herein can be utilized in accordance with the disclosure.

Polypeptide or polynucleotide molecules of the present disclosure may share a certain degree of sequence similarity or identity with the reference molecules (e.g., reference polypeptides or reference polynucleotides), for example, with art-described molecules (e.g., engineered, or designed molecules or wild-type molecules). The term "identity," as known in the art, refers to a relationship between the sequences of two or more polypeptides or polynucleotides, as determined by comparing the sequences. In the art, identity also means the degree of sequence relatedness between two sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. Identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al. (1997)." Gapped BLAST and PSI-BLAST: a new generation of protein database search programs," *Nucleic Acids Res.* 25:3389-3402). Another popular local alignment technique is based on the Smith-Waterman algorithm (Smith, T. F. & Waterman, M. S. (1981) "Identification of common molecular subsequences." *J. Mol. Biol.* 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." *J. Mol. Biol.* 48:443-453). More recently, a Fast Optimal Global Sequence Alignment Algorithm (FOGSAA) was developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g., between nucleic acid molecules (e.g., DNA molecules) and/or between polypeptide molecules. Polymeric molecules (e.g., nucleic acid molecules (e.g., DNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, 96%, 97%, 98% or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

The term "identity" refers to the overall relatedness between polymeric molecules, for example, between polynucleotide molecules (e.g., DNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleic acid sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM *J Applied Math.*, 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research*, 12, 387 (1984)), BLASTP, BLASTN, and FASTA Altschul, S. F. et al., *J. Molec. Biol.*, 215, 403 (1990)).

Lipid Nanoparticles

As used herein, "lipid nanoparticle" or "LNP" refers to any lipid composition that can be used to deliver a product, including, but not limited to, liposomes or vesicles, wherein an aqueous volume is encapsulated by amphipathic lipid bilayers (e.g., single; unilamellar or multiple; multilamellar), or, in other embodiments, wherein the lipids coat an interior comprising a prophylactic product, or lipid aggregates or micelles, wherein the lipid encapsulated therapeutic product is contained within a relatively disordered lipid mixture. Except where noted, the lipid nanoparticle does not need to have the antigenic polypeptide incorporated therein and may be used to deliver a product when in the same formulation.

As used herein, "polyamine" means compounds having two or more amino groups. Examples include putrescine, cadaverine, spermidine, and spermine.

Unless otherwise specified, mole % refers to a mole percent of total lipids. Generally, the LNPs of the compositions of the invention are composed of one or more cationic lipids (including ionizable cationic lipids) and one or more poly(ethyleneglycol)-lipids (PEG-lipids). In certain embodiments, the LNPs further comprise one or more non-cationic lipids. The one or more non-cationic lipids can include a phospholipid, phospholipid derivative, a sterol, a fatty acid, or a combination thereof.

Cationic lipids and ionizable cationic lipids suitable for the LNPs are described herein. Ionizable cationic lipids are characterized by the weak basicity of their lipid head groups, which affects the surface charge of the lipid in a pH-dependent manner, rendering them positively charged at acidic pH but close to charge-neutral at physiologic pH. Cationic lipids are characterized by monovalent or multivalent cationic charge on their headgroups, which renders them positively charged at neutral pH. In certain embodiments, the cationic and ionizable lipid is capable of complexing with hydrophilic bioactive molecules to produce a hydrophobic complex that partitions into the organic phase of a two-phase aqueous/organic system. It is contemplated that both monovalent and polyvalent cationic lipids may be utilized to form hydrophobic complexes with bioactive molecules.

In some embodiments, the cationic and ionizable cationic lipids for use in forming the LNPs include, but are not limited to, N,N-dioleyl-N,N-dimethylammonium chloride ("DODAC"); N-(2,3dioleyloxy)propyl)-N,N,Ntrimethylammonium chloride ("DOTMA"); N,NdistearylN,N-dimethylammonium bromide ("DDAB"); N-(2,3dioleoyloxy)propyl)-N,N,N-trimethylamntonium chloride ("DODAP"); 1,2 bis (oleoyloxy)-3-(trimethylammonio) propane (DOTAP); 3-(N—(N,N-dimethylaminoethane)-carbam-oyl)cholesterol ('DC-Chol'); diheptadecylamidoglycylspermidine ("DHGS") and N-(1,2-dimyristyloxyprop-3-yl)-N,N-dimethyl-N-hydoxyethyl ammonium bromide ("DMRIE"). Additionally, a number of commercial preparations of cationic lipids, as well as other components, are available which can be used in the present invention. These include, for example, LIPOFECTIN® (commercially available cationic lipid nanoparticles comprising DOTMA and 1,2dioleoyl-sn-3-phosphoethanolamine ("DOPE"), from GIBCO-BRL, Grand Island, N.Y., USA); and LIPOFECTAMINE® (commercially available cationic lipid nanoparticles comprising N-(1-(2,3dioleyloxy)propyl)N-(2-(sperminecarboxamido)ethyl)-N,N-dimethylammonium trifluoroacetate ("DOSPA') and ("DOPE"), from (GIBCOBRL). The following lipids are cationic and have a positive charge at below physiological pH: DODAP, DODMA, DMDMA, 1,2-DiLinoleyloxy-N,N-dimethylaminopropane (DLinDMA), 4-(2,2-diocta-9,12-dienyl-[1,3]dioxolan-4-ylmethyl)-dimethylamine, DLinKDMA (WO 2009/132131 A1), DLin-K-C2-DMA (WO2010/042877), DLin-M-C3-DMA (WO2010/146740 and/or WO2010/105209), DLin-MC3-DMA (heptatriaconta-6,9,28,31-tetraen-19-yl4-(dimethylamino)butanoate; Jayaraman et al., 2012, Angew. Chem. Int. Ed. Engl. 51:8529-8533), 2-{4-[(3β)-cholest-5-en-3-yloxy]butoxy}-N,N-dimethyl-3-[(9Z,12Z)-octadeca-9, 12-dienyloxyl]propan-1-amine) (CLinDMA), and the like. Other cationic lipids suitable for use in the invention include, e.g., the cationic lipids described in U.S. Pat. Nos. 5,208,036, 5,264,618, 5,279,833 and 5,283,185, and U.S. Patent Application Publication Nos. 2008/0085870 and 2008/0057080. Other cationic lipids suitable for use in the invention include, e.g., Lipids E0001-E0118 or E0119-E0180 as disclosed in Table 6 (pages 112-139) of International Patent Application Publication No. WO2011/076807 (which also discloses methods of making, and methods of using these cationic lipids).

In some embodiments, the cationic lipid comprises any one of DLinDMA; DlinKC2DMA; DLin-MC3-DMA; CLinDMA; S-Octyl CLinDMA;

(2 S)-1-{7-[(3β)-cholest-5-en-3-yloxy]heptyloxy}-3-[(4Z)-dec-4-en-1-yloxy]-N, N-dimethylpropan-2-amine;

(2R)-1-{4-[(3β)-cholest-5-en-3-yloxy]butoxy}-3-[(4Z)-dec-4-en-1-yloxy]-N, N-dimethylpropan-2-amine;

1-[(2R)-1-{4-[(3β)-cholest-5-en-3-yloxy]butoxy}-3-(octyloxy)propan-2-yl]guanidine;

1-[(2R)-1-{7-[(3β)-cholest-5-en-3-yloxy]heptyloxy}-N,N-dimethyl-3-[(9Z,12Z)-octadeca-9,12-dien-1-yloxy]propan-2-amine;

1-[(2R)-1-{4-[(3β)-cholest-5-en-3-yloxy]butoxy}-N,N-dimethyl-3-[(9Z,12Z)-octadeca-9,12-dien-1-yloxy]propan-2-amine;

(2S)-1-({6-[(3β))-cholest-5-en-3-yloxy]hexyl}oxy)-N,N-dimethyl-3-[(9Z)-octadec-9-en-1-yloxy]propan-2-amine;

(3β)-3-[6-{[(2S)-34 (9Z)-octadec-9-en-1-yloxy]-2-(pyrrolidin-1-yl)propyl]oxy}hexyl)oxy]cholest-5-ene;
(2R)-1-{4-[(3β)-cholest-5-en-3-yloxy]butoxy}-3-(octyloxy)propan-2-amine;
(2R)-1-({8-[(3β)-cholest-5-en-3-yloxy]octyl}oxy)-N,N-dimethyl-3-(pentyloxy)propan-2-amine;
(2R)-1-({8-[(3β)-cholest-5-en-3-yloxy]octyl}oxy)-3-(heptyloxy)-N,N-dimethylpropan-2-amine;
(2R)-1-({8-[(3β)-cholest-5-en-3-yloxy]octyl}oxy)-N,N-dimethyl-3-[(2Z)-pent-2-en-1-yloxy]propan-2-amine;
(2S)-1-butoxy-3-({8-[(3β)-cholest-5-en-3-yloxy]octyl}oxy)-N,N-dimethylpropan-2-amine;
(2S-1-({8-[(3β)-cholest-5-en-3-yloxy]octyl}oxy)-3-[2,2,3,3,4,4,5,5,6,6,7,7,8,8,9,9-hexadecafluorononyl)oxy]-N,N-dimethylpropan-2-amine;
2-amino-2-{[(9Z,12Z)-octadeca-9,12-dien-1-yloxy]methyl}propane-1,3-diol;
2-amino-3-((9-(((3S,10R,13R)-10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)nonyl)oxy)-2-((((9Z,12Z)-octadeca-9,12-dien-1-yl)oxy)methyl)propan-1-ol;
2-amino-3-((6-(((3S,10R,13R)-10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)hexyl)oxy)-2-((((Z)-octadec-9-en-1-yl)oxy)methyl)propan-1-ol;
(20Z,23Z)-N,N-dimethylnonacosa-20,23-dien-10-amine;
(17Z,20Z)-N,N-dimethylhexacosa-17,20-dien-9-amine;
(16Z,19Z)-N,N-dimethylpentacosa-16,19-dien-8-amine;
(13Z,16Z)-N,N-dimethyldocosa-13,16-dien-5-amine;
(12Z,15Z)-N,N-dimethylhenicosa-12,15-dien-4-amine;
(14Z,17Z)-N,N-dimethyltricosa-14,17-dien-6-amine;
(15Z,18Z)-N,N-dimethyltetracosa-15,18-dien-7-amine;
(18Z,21Z)-N,N-dimethylheptacosa-18,21-dien-10-amine;
(15Z,18Z)-N,N-dimethyltetracosa-15,18-dien-5-amine;
(14Z,17Z)-N,N-dimethyltricosa-14,17-dien-4-amine;
(19Z,22Z)-N,N-dimethyloctacosa-19,22-dien-9-amine;
(18Z,21Z)-N,N-dimethylheptacosa-18,21-dien-8-amine;
(17Z,20Z)-N,N-dimethylhexacosa-17,20-dien-7-amine;
(16Z,19Z)-N,N-dimethylpentacosa-16,19-dien-6-amine;
(22Z,25Z)-N,N-dimethylhentriaconta-22,25-dien-10-amine;
(21Z,24Z)-N,N-dimethyltriaconta-21,24-dien-9-amine;
(18Z)-N,N-dimethylheptacos-18-en-10-amine;
(17Z)-N,N-dimethylhexacos-17-en-9-amine;
(19Z,22Z)-N,N-dimethyloctacosa-19,22-dien-7-amine;
N,N-dimethylheptacosan-10-amine;
(20Z,23Z)-N-ethyl-N-methylnonacosa-20,23-dien-10-amine;
1-[(11Z,14Z)-1-nonylicosa-11,14-dien-1-yl]pyrrolidine;
(20Z)-N,N-dimethylheptacos-20-en-10-amine;
(15Z)-N,N-dimethylheptacos-15-en-10-amine;
(14Z)-N,N-dimethylnonacos-14-en-10-amine;
(17Z)-N,N-dimethylnonacos-17-en-10-amine;
(24Z)-N,N-dimethyltritriacont-24-en-10-amine;
(20Z)-N,N-dimethylnonacos-20-en-10-amine;
(22Z)-N,N-dimethylhentriacont-22-en-10-amine;
(16Z)-N,N-dimethylpentacos-16-en-8-amine;
(12Z,15Z)-N,N-dimethyl-2-nonylhenicosa-12,15-dien-1-amine;
(13Z,16Z)-N,N-dimethyl-3-nonyldocosa-13,16-dien-1-amine;
N,N-dimethyl-1-[(1S,2R)-2-octylcyclopropyl]heptadecan-8-amine;
1-[(1S,2R)-2-hexylcyclopropyl]-N,N-dimethylnonadecan-10-amine;
N,N-dimethyl-1-[(1S,2R)-2-octylcyclopropyl]nonadecan-10-amine;
N,N-dimethyl-21-[(1S,2R)-2-octylcyclopropyl]henicosan-10-amine;
N,N-dimethyl-1-1[(1S,2S)-2-{[(1R,2R)-2-pentylcyclopropyl]methyl}cyclopropyl]nonadecan-10-amine;
N,N-dimethyl-1-1-[(1S,2R)-2-octylcyclopropyl]hexadecan-8-amine;
N,N-dimethyl-1-1-[(1R,2S)-2-undecylcyclopropyl]tetradecan-5-amine;
N,N-dimethyl-3-{7-[(1S,2R)-2-octylcyclopropyl]heptyl}dodecan-1-amine;
1-[(1R,2S)-2-heptylcyclopropyl]-N,N-dimethyloctadecan-9-amine;
1-[(1S,2R)-2-decylcyclopropyl]-N,N-dimethylpentadecan-6-amine;
N,N-dimethyl-1-[(1S,2R)-2-octylcyclopropyl]pentadecan-8-amine; and
(11E,20Z,23Z)-N,N-dimethylnonacosa-11,20,23-trien-10-amine;
or a pharmaceutically acceptable salt thereof, or a stereoisomer of any of the foregoing.

In certain aspects of this embodiment of the invention, the LNPs comprise one or more of the following ionizable cationic lipids: DLinDMA, DlinKC2DMA DLin-MC3-DMA, CLinDMA, or S-Octyl CLinDMA (See International Patent Application Publication No. WO2010/021865). In other aspects of this embodiment of the invention, the LNPs comprise one or more of the following ionizable and cationic lipids: (13Z,16Z)-N,N-dimethyl-3-nonyldocosa-13,16-dien-1-amine or N,N-dimethyl-1-[(1S,2R)-2-octylcyclopropyl]hexadecan-8-amine, each of which are described in PCT/US2011/0523238, published as WO 2012/040184, the entire contents of which are hereby incorporated by reference.

In certain aspects of this embodiment of the invention, the ionizable and cationic lipid may comprise a lipid described in WO 2017/049245, the entire contents of which are hereby incorporated by reference.

In certain aspects of this embodiment of the invention, LNPs comprise one or more ionizable cationic lipids described in International Patent Application Publication No. WO2011/022460 A1, or any pharmaceutically acceptable salt thereof, or a stereoisomer of any of the compounds or salts therein.

When structures of the same constitution differ in respect to the spatial arrangement of certain atoms or groups, they are stereoisomers, and the considerations that are significant in analyzing their interrelationships are topological. If the relationship between two stereoisomers is that of an object and its nonsuperimposable mirror image, the two structures are enantiomeric, and each structure is said to be chiral. Stereoisomers also include diastereomers, cis-trans isomers and conformational isomers. Diastereoisomers can be chiral or achiral and are not mirror images of one another. Cis-trans isomers differ only in the positions of atoms relative to a specified plane in cases where these atoms are, or are considered as if they were, parts of a rigid structure. Conformational isomers are isomers that can be interconverted by rotations about formally single bonds. Examples of such conformational isomers include cyclohexane conformations with chair and boat conformers, carbohydrates, linear alkane conformations with staggered, eclipsed, and gauche conformers, etc. See J. Org. Chem. 35, 2849 (1970).

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, enantiomers are identical except that they are non-superimposable mirror images of one another. A mixture of enantiomers is often called an enantiomeric mixture. A 50:50 mixture of enantiomers is referred to as a racemic mixture. Many of the cationic lipids described herein can have one or more chiral centers and therefore can exist in different enantiomeric forms. If desired, a chiral carbon can be designated with an asterisk (*). When bonds to the chiral carbon are depicted as straight lines in the Formulas of the invention, it is understood that both the (R) and (S) configurations of the chiral carbon, and hence both enantiomers and mixtures thereof, are embraced within the Formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines (bonds to atoms below the plane). The Cahn-Inglod-Prelog system can be used to assign the (R) or (S) configuration to a chiral carbon.

When the cationic lipids of the present invention contain one chiral center, the compounds exist in two enantiomeric forms and the present invention includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the cationic lipids described herein is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%.

When a cationic lipid described herein has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The LNPs described herein includes each diastereoisomer of such cationic lipids and mixtures thereof.

The LNPs may also comprise any combination of two or more of the cationic lipids described herein. In certain aspects, the cationic lipid typically comprises from about 0.1 to about 99.9 mole % of the total lipid present in said particle. In certain aspects, the cationic lipid can comprise from about 80 to about 99.9% mole %. In other aspects, the cationic lipid comprises from about 2% to about 70%, from about 5% to about 50%, from about 10% to about 45%, from about 20% to about 99.8%, from about 30% to about 70%, from about 34% to about 59%, from about 20% to about 40%, or from about 30% to about 40% (mole %) of the total lipid present in said particle.

The LNPs described herein can further comprise a non-cationic lipid, which can be any of a variety of neutral uncharged, zwitterionic or anionic lipids capable of producing a stable complex. They are preferably neutral, although they can be negatively charged. Examples of noncationic lipids useful in the present invention include phospholipid-related materials, such as natural phospholipids, synthetic phospholipid derivatives, fatty acids, sterols, and combinations thereof. Natural phospholipids include phosphatidylcholine (PC), phosphatidylethanolamine (PE), and phosphatidylglycerol (PG), phosphatidylserine (PS), phosphatidylinositol (PI), Phosphatidic acid (phosphatidate) (PA), dipalmitoylphosphatidylcholine, monoacyl-phosphatidylcholine (lyso PC), 1-palmitoyl-2-oleoyl-sn-glycero-3-phosphocholine (POPC), N-Acyl-PE, phosphoinositides, and phosphosphingolipids. Phospholipid derivatives include phosphatidic acid (DMPA, DPPA, DSPA), phosphatidylcholine (DDPC, DLPC, DMPC, DPPC, DSPC, DOPC, POPC, DEPC), phosphatidylglycerol (DMPG, DPPG, DSPG, POPG), phosphatidylethanolamine (DMPE, DPPE, DSPE DOPE), and phosphatidylserine (DOPS). Fatty acids include C14:0, palmitic acid (C16:0), stearic acid (C18:0), oleic acid (C18:1), linoleic acid (C18:2), linolenic acid (C18:3), and arachidonic acid (C20:4), C20:0, C22:0 and lethicin. In certain embodiments of the LNP described herein, the non-cationic lipid is selected from lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidyletha-nolamine (POPE) and dioleoyl-phosphatidylethanolamine 4-(N-maleimidomethyl)-cyclohexane-1-carboxylate (DOPE-mal). Noncationic lipids also include sterols such as cholesterol, stigmasterol or stigmastanol. Cholesterol is known in the art. See U.S. Patent Application Publication Nos: U.S. 2006/0240554 and U.S. 2008/0020058. In certain embodiments, the LNP comprise a combination of a phospholipid and a sterol.

Where present, the non-cationic lipid typically comprises from about 0.1% to about 65%, about 2% to about 65%, about 10% to about 65%, or about 25% to about 65% expressed as mole percent of the total lipid present in the LNP. The LNPs described herein further include a polyethyleneglycol (PEG) lipid conjugate ("PEG-lipid") which may aid as a bilayer stabilizing component. The lipid component of the PEG lipid may be any non-cationic lipid described above including natural phospholipids, synthetic phospholipid derivatives, fatty acids, sterols, and combinations thereof. In certain embodiments of the LNPs described herein, the PEG-lipids include, PEG coupled to dialkyloxypropyls (PEG-DAA) as described in, e.g., International Patent Application Publication No. WO 05/026372, PEG coupled to diacylglycerol (PEG-DAG) as described in, e.g., U.S. Patent Publication Nos. 20030077829 and 2005008689; PEG coupled to phosphatidylethanolamine (PE) (PEG-PE), or PEG conjugated to 1,2-Di-O-hexadecyl-sn-glyceride (PEG-DSG), or any mixture thereof (see, e.g., U.S. Pat. No. 5,885,613).

In one embodiment, the PEG-DAG conjugate is a dilaurylglycerol (C 12)-PEG conjugate, a PEG dimyristylglycerol (C14) conjugate, a PEG-dipalmitoylglycerol (C16) conjugate, a PEG-dilaurylglycamide (C12) conjugate, a PEG-dimyristylglycamide (C14) conjugate, a PEG-dipalmitoylglycamide (C16) conjugate, or a PEG-disterylglycamide (C18). Those of skill in the art will readily appreciate that other diacylglycerols can be used in the PEG-DAG conjugates.

In certain embodiments, PEG-lipids include, but are not limited to, PEG-dimyristolglycerol (PEG-DMG), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), and PEG-1,2-dimyristyloxlpropyl-3-amine (PEG-c-DMA).

In certain embodiments, the PEG-lipid is PEG coupled to dimyristoylglycerol (PEG-DMG), e.g., as described in Abrams et al., 2010, Molecular Therapy 18(1):171, and U.S. Patent Application Publication Nos. US 2006/0240554 and US 2008/0020058, including for example, 2KPEG/PEG200-DMG.

In certain embodiments, the PEG-lipid, such as a PEG-DAG, PEG-cholesterol, PEG-DMB, comprises a polyethylene glycol having an average molecular weight ranging of about 500 daltons to about 10,000 daltons, of about 750 daltons to about 5,000 daltons, of about 1,000 daltons to about 5,000 daltons, of about 1,500 daltons to about 3,000 daltons or of about 2,000 daltons. In certain embodiments, the PEG-lipid comprises PEG400, PEG1500, PEG2000 or PEG5000.

The acyl groups in any of the lipids described above are preferably acyl groups derived from fatty acids having about C10 to about C24 carbon chains. In one embodiment, the acyl group is lauroyl, myristoyl, palmitoyl, stearoyl or oleoyl.

The PEG-lipid conjugate typically comprises from about 0.1% to about 15%, from about 0.5% to about 20%, from about 1.5% to about 18%, from about 4% to about 15%, from about 5% to about 12%, from about 1% to about 4%, or about 2% expressed as a mole % of the total lipid present in said particle.

In certain embodiments of the invention, the LNPs comprise one or more cationic lipids, cholesterol, and 1,2-Dimyristoyl-sn-glycerol methoxypolyethylene glycol (PEG-DMG).

In certain embodiments the invention, the LNPs comprise one or more cationic lipids, cholesterol, 1,2-Distearoyl-sn-glycero-3-phosphocholine (DSPC), and 1,2-Dimyristoyl-sn-glycerol methoxypolyethylene glycol (PEG-DMG).

In certain embodiments of the invention, the LNPs comprise lipid compounds assembled within the following molar ratios:
Cationic Lipid (20-99.8 mole %)
Non-cationic lipid (0.1-65 mole %) and
PEG-DMG (0.1-20 mole %).

In certain embodiments of the invention, the LNPs comprise lipid compounds assembled within the following molar ratios:
Cationic Lipid (30-70 mole %)
Non-cationic lipid (20-65 mole %) and
PEG-DMG (1-15 mole %).

In certain aspects of this embodiment, the non-cationic lipid is cholesterol.

Exemplary LNPs may include cationic lipid/cholesterol/PEG-DMG at about the following molar ratios: 58/30/10.

In certain aspects of this embodiment, the non-cationic lipid is cholesterol and DSPC. Exemplary LNPs may include cationic lipid/cholesterol/DSPC/PEG-DMG at about the following molar ratios: 59/30/10/1; 58/30/10/2; 43/41/15/1; 42/41/15/2; 40/48/10/2; 39/41/19/1; 38/41/19/2; 34/41/24/1; and 33/41/24/2.

Preparation of LNPs

LNPs can be formed, for example, by a rapid precipitation process which entails micro-mixing the lipid components dissolved in ethanol with an aqueous solution using a confined volume mixing apparatus such as a confined volume T-mixer, a multi-inlet vortex mixer (MIVM), or a microfluidics mixer device as described below. The lipid solution contains one or more cationic lipids, one or more noncationic lipids (e.g., DSPC), PEG-DMG, and optionally cholesterol, at specific molar ratios in ethanol. The aqueous solution consists of a sodium citrate or sodium acetate buffered salt solution with pH in the range of 2-6, preferably 3.5-5.5. The two solutions are heated to a temperature in the range of 25° C.-45° C., preferably 30° C.-40° C., and then mixed in a confined volume mixer thereby instantly forming the LNP. When a confined volume T-mixer is used, the T-mixer has an internal diameter (ID) range from 0.25 to 1.0 mm. The alcohol and aqueous solutions are delivered to the inlet of the T-mixer using programmable syringe pumps, and with a total flow rate from 10-600 mL/minute. The alcohol and aqueous solutions are combined in the confined-volume mixer with a ratio in the range of 1:1 to 1:3 vol:vol, but targeting 1:1.1 to 1:2.3. The combination of ethanol volume fraction, reagent solution flow rates and t-mixer tubing ID utilized at this mixing stage has the effect of controlling the particle size of the LNPs between 30 and 300 nm. The resulting LNP suspension is twice diluted into higher pH buffers in the range of 6-8 in a sequential, multi-stage in-line mixing process. For the first dilution, the LNP suspension is mixed with a buffered solution at a higher pH (pH 6-7.5) with a mixing ratio in the range of 1:1 to 1:3 vol:vol, but targeting 1:2 vol:vol. This buffered solution is at a temperature in the range of 15-40° C., targeting 30-40° C. The resulting LNP suspension is further mixed with a buffered solution at a higher pH, e.g., 6-8 and with a mixing ratio in the range of 1:1 to 1:3 vol:vol, but targeting 1:2 vol:vol. This later buffered solution is at a temperature in the range of 15-40° C., targeting 16-25° C. The mixed LNPs are held from 30 minutes to 2 hours prior to an anion exchange filtration step. The temperature during incubation period is in the range of 15-40° C., targeting 30-40° C. After incubation, the LNP suspension is filtered through a 0.8 μm filter containing an anion exchange separation step. This process uses tubing IDs ranging from 1 mm ID to 5 mm ID and a flow rate from 10 to 2000 mL/minute. The LNPs are concentrated and diafiltered via an ultrafiltration process where the alcohol is removed and the buffer is exchanged for the final buffer solution such as phosphate buffered saline or a buffer system suitable for cryopreservation (for example containing sucrose, trehalose, or combinations thereof). The ultrafiltration process uses a tangential flow filtration format (TFF). This process uses a membrane nominal molecular weight cutoff range from 30-500 KD, targeting 100 KD. The membrane format can be hollow fiber or flat sheet cassette. The TFF processes with the proper molecular weight cutoff retains the LNP in the retentate and the filtrate or permeate contains the alcohol and final buffer wastes. The TFF process is a multiple step process with an initial concentration to a lipid concentration of 20-30 mg/mL. Following concentration, the LNP suspension is diafiltered against the final buffer (for example, phosphate buffered saline (PBS) with pH 7-8, 10 mM Tris, 140 mM NaCl with pH 7-8, or 10 mM Tris, 70 mM NaCl, 5 wt % sucrose, with pH 7-8) for 5-20 volumes to remove the alcohol and perform buffer exchange. The material is then concentrated an additional 1-3 fold via ultrafiltration. The final steps of the LNP manufacturing process are to sterile filter the concentrated LNP solution into a suitable container under aseptic conditions. Sterile filtration is accomplished by passing the LNP solution through a pre-filter (Acropak 500 PES 0.45/0.8 μm capsule) and a bioburden reduction filter (Acropak 500 PES 0.2/0.8 μm capsule). Following filtration, the vialed LNP product is stored under suitable storage conditions (2° C.-8° C., or −20° C. if frozen formulation).

In some embodiments, the LNPs of the compositions provided herein have a mean geometric diameter that is less than 1000 nm. In some embodiments, the LNPs have mean geometric diameter that is greater than 50 nm but less than 500 nm. In some embodiments, the mean geometric diameter of a population of LNPs is about 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, the mean geometric diameter is between 100-400 nm, 100-300 nm, 100-250 nm, or 100-200 nm. In some embodiments, the mean geometric diameter is between 60-400 nm, 60-350 nm, 60-300 nm, 60-250 nm, or 60-200 nm. In some embodiments, the mean geometric diameter is between 75-250 nm. In some embodiments, 30%, 40%, 50%, 60%, 70%, 80%, 90%, or more of the LNPs of a population of LNPs have a diameter that is less than 500 nm. In some embodiments, 10%, 20%, 30%, 40%, 50%, 60%, 70%, 80%, 90%, or more of the LNPs of a population of LNPs have a diameter that is greater than 50 nm but less than 500 nm. In some embodiments, 10%, 20%, 30%, 40%, 50%, 60%, 70%, 80%, 90%, or more of the LNPs of a population of LNPs have a diameter of about 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, 10%, 20%, 30%, 40%, 50%, 60%, 70%, 80%, 90%, or more of the LNPs of a population of LNPs have a diameter that is between 100-400 nm, 100-300 nm, 100-250 nm, or 100-200 nm. In some embodiments, 10%, 20%, 30%, 40%, 50%, 60%, 70%, 80%, 90%, or more of the LNPs of a population of LNPs have a diameter that is between 60-400 nm, 60-350 nm, 60-300 nm, 60-250 nm, or 60-200 nm.

In a particular embodiment, the size of the LNPs ranges between about 1 and 1000 nm, preferably between about 10 and 500 nm, more preferably between about 100 to 300 nm, and preferably 100 nm.

Nucleic Acids/Polynucleotides

DNA of the present disclosure, in some embodiments, are codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, a codon optimized sequence shares less than 95% sequence identity, less than 90% sequence identity, less than 85% sequence identity, less than 80% sequence identity, or less than 75% sequence identity to a naturally occurring or wild-type sequence.

In some embodiments, a codon-optimized sequence shares between 65% and 85% (e.g., between about 67% and about 85%, or between about 67% and about 80%) sequence identity to a naturally occurring sequence or a wild-type sequence. In some embodiments, a codon-optimized sequence shares between 65% and 75%, or about 80% sequence identity to a naturally occurring sequence or wild-type sequence.

Methods of Treatment

Provided herein are compositions (e.g., pharmaceutical compositions), methods, kits, and reagents for prevention and/or treatment of RSV in humans and other mammals. RSV virus vaccines can be used as therapeutic or prophylactic agents. They may be used in medicine to prevent and/or treat infectious disease. In exemplary aspects, the RSV immunogenic compositions of the present disclosure are used as vaccines to provide prophylactic protection from RSV virus. Prophylactic protection from RSV virus can be achieved following administration of an RSV vaccine of the present disclosure. Vaccines can be administered once, twice, three times, four times or more. It is possible, although less desirable, to administer the vaccine to an infected individual to achieve a therapeutic response. Dosing may need to be adjusted accordingly.

In some embodiments, the RSV immunogenic compositions of the present disclosure can be used as a method of preventing an RSV infection in a subject, the method comprising administering to said subject at least one RSV immunogenic composition as provided herein. In some embodiments, the RSV immunogenic compositions of the present disclosure can be used as a method of treating an RSV infection in a subject, the method comprising administering to said subject at least one RSV immunogenic composition as provided herein. In some embodiments, the RSV immunogenic compositions of the present disclosure can be used as a method of reducing an incidence of RSV in a subject, the method comprising administering to said subject at least one RSV immunogenic composition as provided herein. In some embodiments, the RSV immunogenic composition of the present disclosure can be used as a method of inhibiting spread of RSV from a first subject infected with RSV to a second subject not infected with RSV, the method comprising administering to at least one of said first subject and said second subject at least one RSV immunogenic composition as provided herein.

A method of eliciting an immune response in a subject against RSV is provided in aspects of the invention. The method involves administering to the subject an RSV immunogenic composition described herein, thereby inducing in the subject an immune response specific to RSV.

A prophylactically effective dose is a therapeutically effective dose that prevents infection with the virus at a clinically acceptable level. In some embodiments the therapeutically effective dose is a dose listed in a package insert for the vaccine.

Therapeutic and Prophylactic Compositions

Provided herein are compositions (e.g., pharmaceutical compositions), methods, kits and reagents for prevention, treatment, or diagnosis of RSV in humans and other mammals, for example. The RSV immunogenic compositions, including vaccines, can be used as therapeutic or prophylactic agents. They may be used in medicine to prevent and/or treat infectious disease. In some embodiments, the RSV immunogenic compositions in accordance with the present disclosure may be used for treatment of RSV.

RSV immunogenic compositions, including RSV vaccines, may be administered prophylactically or therapeutically as part of an active immunization scheme to healthy individuals or early in infection during the incubation phase or during active infection after onset of symptoms. In some embodiments, the amount of vaccine of the present disclosure provided to a cell, a tissue or a subject may be an amount effective for immune prophylaxis.

RSV immunogenic compositions, including RSV vaccines, may be administrated with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In some embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, RSV immunogenic compositions, including RSV vaccines, may be administered intramuscularly, intradermally, or intranasally, similarly to the administration of inactivated vaccines known in the art. In some embodiments, RSV immunogenic compositions, including RSV vaccines, are administered intramuscularly.

RSV immunogenic compositions, including RSV vaccines, may be utilized in various settings depending on the prevalence of the infection or the degree or level of unmet medical need. Vaccines have superior properties in that they produce much larger antibody titers and produce responses early than commercially available anti-viral agents/compositions.

Provided herein are pharmaceutical compositions including RSV immunogenic compositions optionally in combination with one or more pharmaceutically acceptable excipients.

RSV immunogenic compositions, which include RSV vaccines, may be formulated or administered alone or in conjunction with one or more other components. For instance, such compositions may comprise other components including, but not limited to, adjuvants.

In some embodiments, the RSV immunogenic compositions do not include an adjuvant (they are adjuvant free).

Aluminium has long been shown to stimulate the immune response against co-administered antigens, primarily by stimulating a TH2 response. It is preferred that the aluminium adjuvant of the compositions provided herein is not in the form of an aluminium precipitate. Aluminium-precipitated vaccines may increase the immune response to a target antigen, but have been shown to be highly heterogeneous preparations and have had inconsistent results (see Lindblad E. B. Immunology and Cell Biology 82: 497-505 (2004)). Aluminium-adsorbed vaccines, in contrast, can be preformed in a standardized manner, which is an essential characteristic of vaccine preparations for administration into humans. Moreover, it is thought that physical adsorption of a desired antigen onto the aluminium adjuvant has an important role in adjuvant function, perhaps in part by allowing a slower clearing from the injection site or by allowing a more efficient uptake of antigen by antigen presenting cells.

The aluminium adjuvant of the present invention may be in the form of aluminium hydroxide ($Al(OH)_3$), aluminium phosphate ($AlPO_4$), aluminium hydroxyphosphate, amorphous aluminium hydroxyphosphate sulfate (AAHS) or so-called "alum" ($KA1(S04)-12H20$) {see Klein et al, Analysis of aluminium hydroxyphosphate vaccine adjuvants by (27) A1 MAS NMR, J. Pharm. Sci. 89(3): 311-21 (2000)). In exemplary embodiments of the invention provided herein, the aluminium adjuvant is aluminium hydroxyphosphate or AAHS. The ratio of phosphate to aluminium in the aluminium adjuvant can range from 0 to 1.3. In preferred embodiments of this aspect of the invention, the phosphate to aluminium ratio is within the range of 0.1 to 0.70. In particularly preferred embodiments, the phosphate to aluminium ratio is within the range of 0.2 to 0.50. MAPA is an aqueous suspension of aluminum hydroxyphosphate. MAPA is manufactured by blending aluminum chloride and sodium phosphate in a 1:1 volumetric ratio to precipitate aluminum hydroxyphosphate. After the blending process, the material is size-reduced with a high-shear mixer to achieve a target aggregate particle size in the range of 2-8 μm. The product is then diafiltered against physiological saline and steam sterilized. See, e.g., International Patent Application Publication No. WO2013/078102.

In some embodiments of the invention, the aluminium adjuvant is in the form of AAHS (referred to interchangeably herein as Merck aluminium adjuvant (MAA)). MAA carries zero charge at neutral pH, while AlOH carries a net positive charge and $AlPO_4$ typically carries a net negative charge at neutral pH.

One of skill in the art will be able to determine an optimal dosage of aluminium adjuvant that is both safe and effective at increasing the immune response to the targeted antigenic polypeptides. For a discussion of the safety profile of aluminium, as well as amounts of aluminium included in FDA-licensed vaccines, see Baylor et al., Vaccine 20: S18-S23 (2002). Generally, an effective and safe dose of aluminium adjuvant varies from 150 to 600 μg/dose (300 to 1200 μg/mL concentration). In specific embodiments of the formulations and compositions of the present invention, there is between 200 and 300 μg aluminium adjuvant per dose of vaccine. In alternative embodiments of the formulations and compositions of the present invention, there is between 300 and 500 μg aluminium adjuvant per dose of vaccine.

RSV immunogenic compositions, including RSV vaccines, may be formulated or administered in combination with one or more pharmaceutically-acceptable excipients. In some embodiments, the compositions comprise at least one additional active substances, such as, for example, a therapeutically-active substance, a prophylactically-active substance, or a combination of both. The compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety). In some embodiments, the RSV immunogenic compositions, including RSV vaccines, are administered to humans, human patients or subjects.

Formulations of the RSV immunogenic compositions described herein may be prepared by any method known or hereafter developed in the art of pharmacology. In general, such preparatory methods include the step of bringing the active ingredient (e.g., polypeptide or polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

Modes of Vaccine Administration

RSV immunogenic compositions, including RSV vaccines, may be administered by any route which results in a therapeutically effective outcome. These include, but are not limited, to intradermal, intramuscular, intranasal and/or subcutaneous administration. The present disclosure provides methods comprising administering compositions to a subject in need thereof. The exact amount required will vary from subject to subject, depending on the species, age, and general condition of the subject, the severity of the disease, the particular composition, its mode of administration, its mode of activity, and the like. RSV immunogenic compositions are typically formulated in dosage unit form for ease of administration and uniformity of dosage. It will be understood, however, that the total daily usage of vaccine compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, RSV immunogenic compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect. In exemplary embodiments, RSV immunogenic compositions vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, the RSV immunogenic compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

An RSV immunogenic pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, intranasal, and subcutaneous).

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1: Generation of Single Chain Mutants Having $F_1$ and $F_2$ Fragments Joined by a Peptide Linker Wildtype RSV F polypeptide is cleaved into $F_1$ and $F_2$ fragments by host furin protease post translation. To evaluate single chain RSV mutants which are not cleaved by furin and which remain as a single polypeptide, amino acids 98-146 of WT RSV (which amino acids include the furin cleavage sites, the p27 peptide and part of the fusion peptide) were replaced with a flexible amino acid linker of various lengths (8-14 a.a.), in the background of prefusion stabilizing DS-Cav1 mutations (S155C, S190F, V207L, and S290C) (McLellan et al. 2013). In these mutants, the T4 phage fibritin trimerization domain (foldon) was appended to the C-terminus of the RSV F ectodomain, followed by a protease cleavage site and purification tags. Mutant RSV F sequences were codon optimized for mammalian codon usage, cloned into an expression vector, and transiently transfected into Expi293 suspension cells (Life Technologies). Cell culture supernatants were harvested day 3 to 7 post-plasmid transfection to assess binding of these mutants to different antibodies against RSV F. Briefly, 96-well Ni-NTA coated plates (Thermo Scientific) were coated with cell culture supernatants for 1 hour at room temperature. Unbound sites were blocked by addition of 2% (v/v) bovine serum albumin (BSA) in PBS and incubation for 1 hour at room temperature. Plates were washed with PBS containing 0.05% (v/v) Tween™ 20 (polysorbate 20) (PBS-T) and incubated with serial dilutions of antibodies (D25 or Synagis® (palivizumab)) at room temperature for 1 hour. Plates were washed again with PBS-T and incubated for 1 hour at room temperature with goat anti-human IgG HRP-conjugated secondary antibody (Thermo Fisher) diluted 1:2,000. Following an additional wash with PBS-T and brief rinse with ddH$_2$O, Super AquaBlue ELISA substrate (eBiosience) was added, and the plate was immediately read at 405 nm for 5 min. mOD/min was calculated for each well.

Figure 1B:
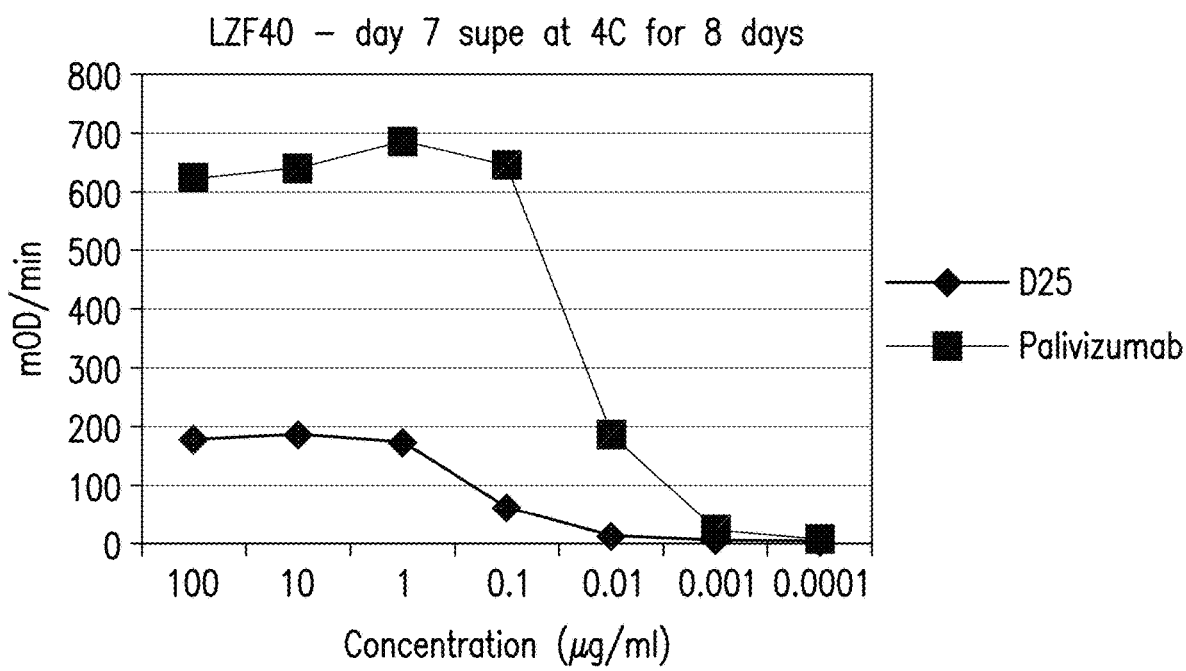
Figure 2A:
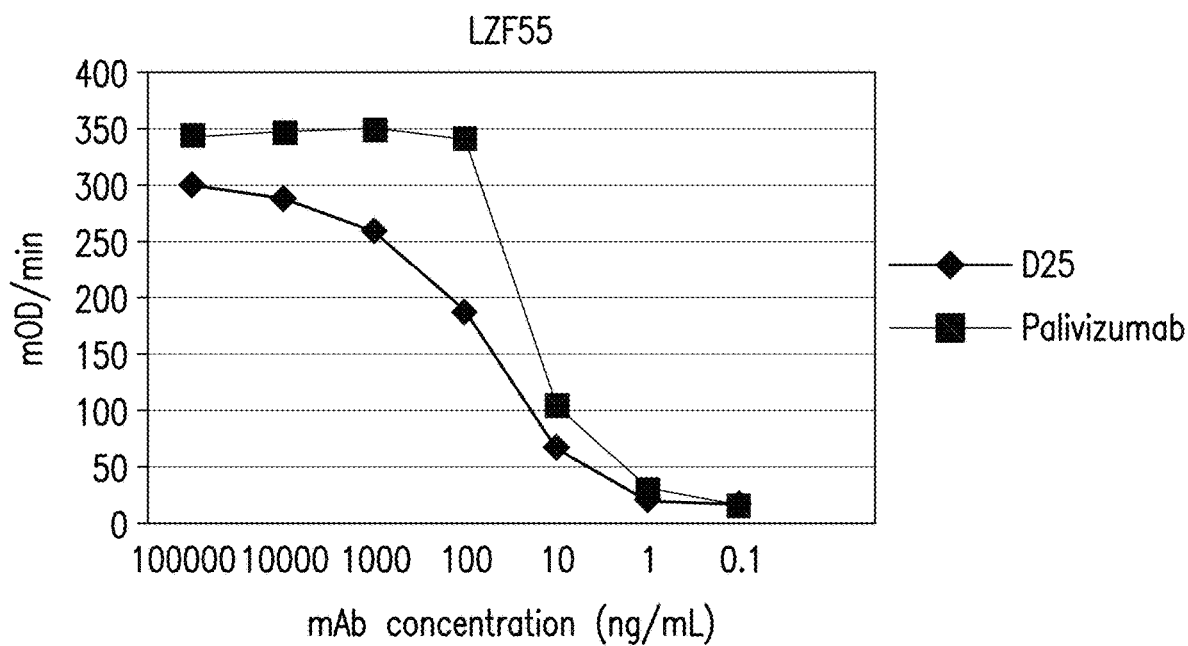
FIGS. 2A-2F show binding of freshly harvested day 3 post-transfection cell culture supernatants (supe) of LZF55 (F55), LZF 56 (F56) and LZF57 (F57) (DS-Cav1 with 10, 12 or 14 a.a. linker, respectively.
Figure 2B:
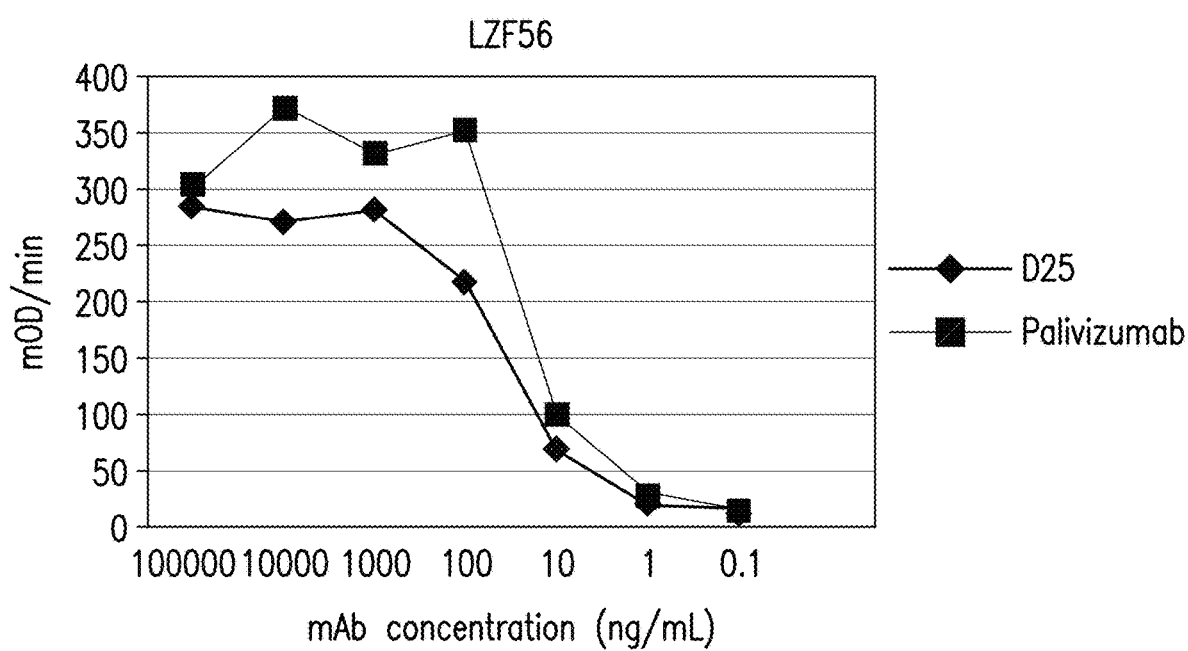
Figure 2C:
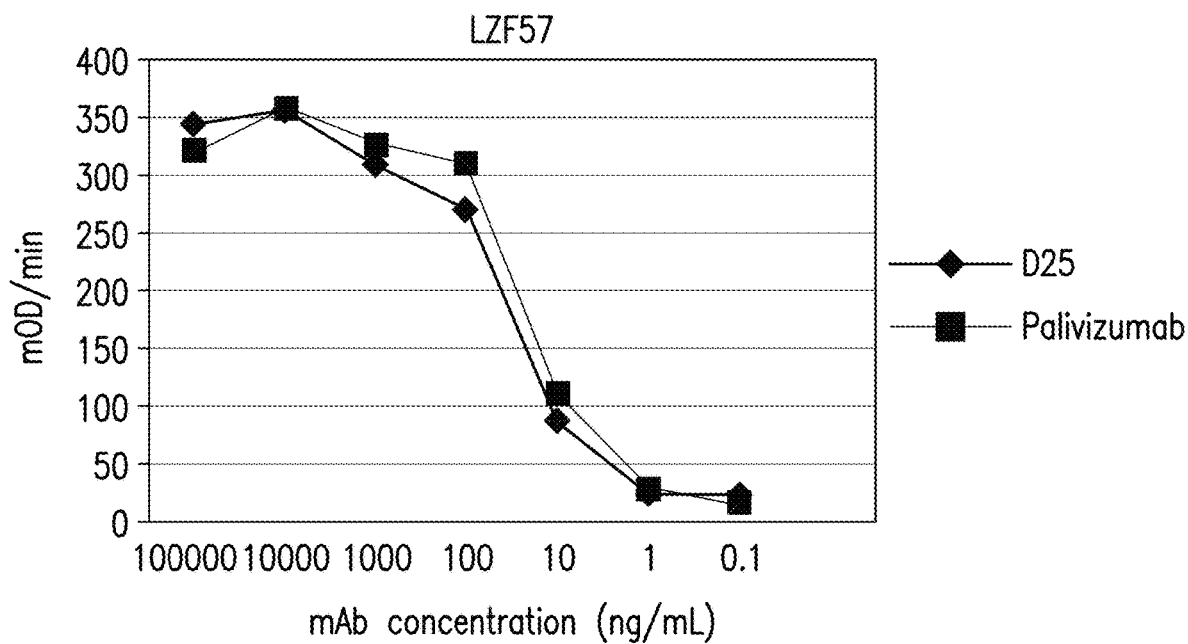
Figure 2D:
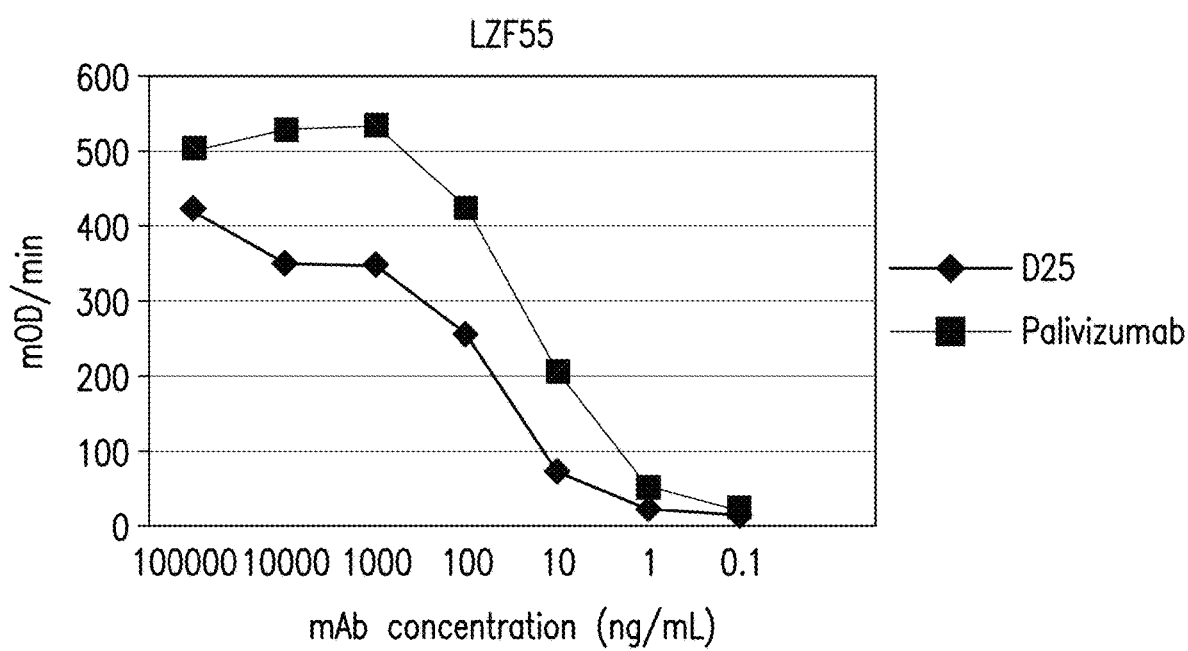
Figure 2E:
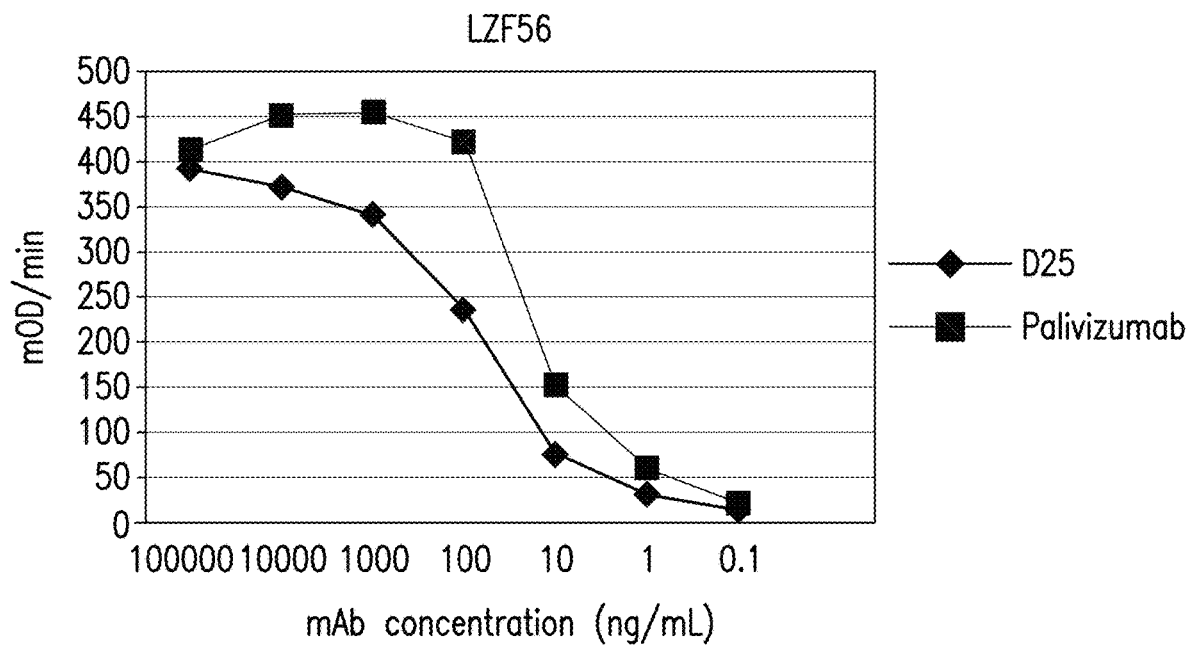
Figure 2F:
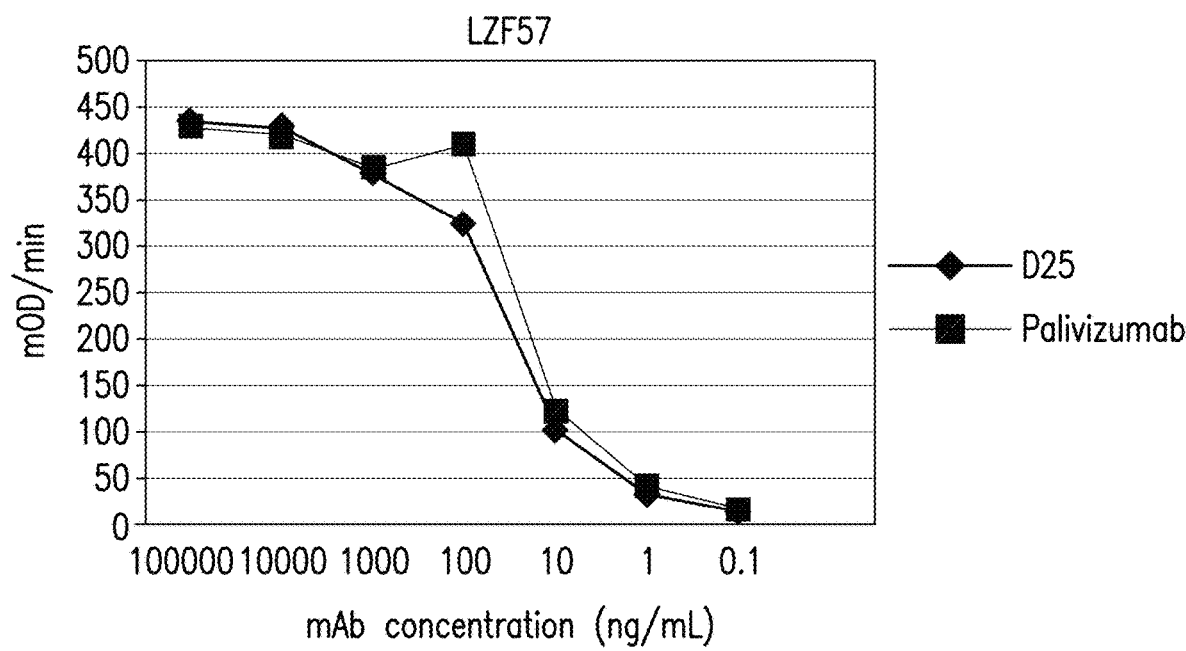

FIGS. 1A and 1B show binding of freshly harvested day 7 post-transfection cell culture supernatants of construct 40a (DS-Cav1 with an 8 a.a. linker) (FIG. 1A) or those stored at 4° C. for 8 days (FIG. 1B) to D25 and Synagis® (palivizumab) monoclonal antibodies. The LZF40a mutant exhibited low prefusion-specific mAb D25 binding. Binding to palivizumab (which reacts to both prefusion and postfusion F) was high, suggesting that the mutant was expressed well. FIGS. 2A and 2B show binding of freshly harvested day 3 post-transfection cell culture supernatants of LZF55a, LZF56a, and LZF57a (DS-Cav1 with 10, 12 or 14 amino acid linker, respectively; FIGS. 2A, 2B, 2C, respectively) or those stored at 4° C. for 7 days (FIGS. 2D, 2E, and 2F, respectively) to D25 and palivizumab. All of the three mutants expressed well, based on the reactivity to palivizumab. Among these mutants, LZF57a (DS-Cav1 with a 14 amino acid linker) exhibited the highest prefusion-specific mAb D25 binding and retained D25 binding after 7 days of storage at 4° C.

Figure 3:
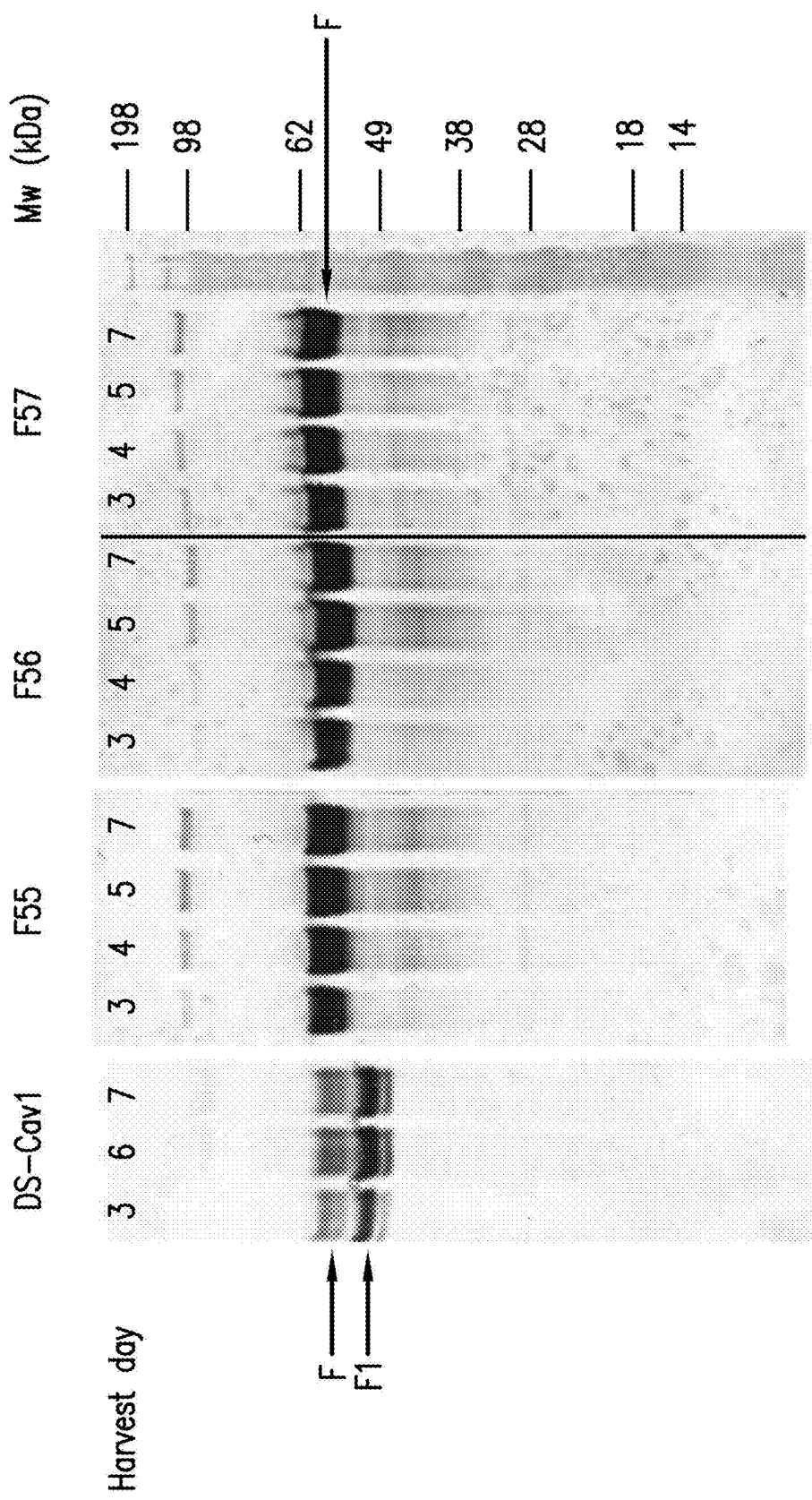
FIG. 3 shows the results of a western blot with anti-RSV F sera for single chain RSV mutants LZF55, LZF56 and LZF57 compared to DS-Cav1.

In addition to ELISA, cell culture supernatants harvested at different post-transfection time points were analyzed on a western blot with anti-RSV F sera. Supernatants were treated with SDS loading buffer with reducing agent (Life Technologies), applied to gel electrophoresis and then electro-transferred onto nitrocellulose membranes (Life Technologies). The membranes were blocked overnight at 4° C. in blotting grade blocker (BioRad) made in 1×TBST (Tris Buffered saline+tween). The membranes were incubated with polyclonal guinea pig sera against ectodomain of wildtype RSV F protein (Sino Biological) followed by an AP-conjugated goat anti-guinea pig IgG secondary antibody (Santa Cruz Biotechnology). Single chain RSV mutants LZF55a, LZF56a, and LZF57a showed significantly improved expression levels compared to the original DS-Cav1 (FIG. 3). DS-Cav1 appeared as two bands on the gel: an upper band represents the uncleaved F protein, and a lower band represents the furin cleaved F$_1$ fragment. The single chain RSV mutants LZF55, LZF56, and LZF57 appeared as a single predominant band on the gel, representing uncleaved F.

Example 2: Additional Stabilizing Mutations

Figure 4A:
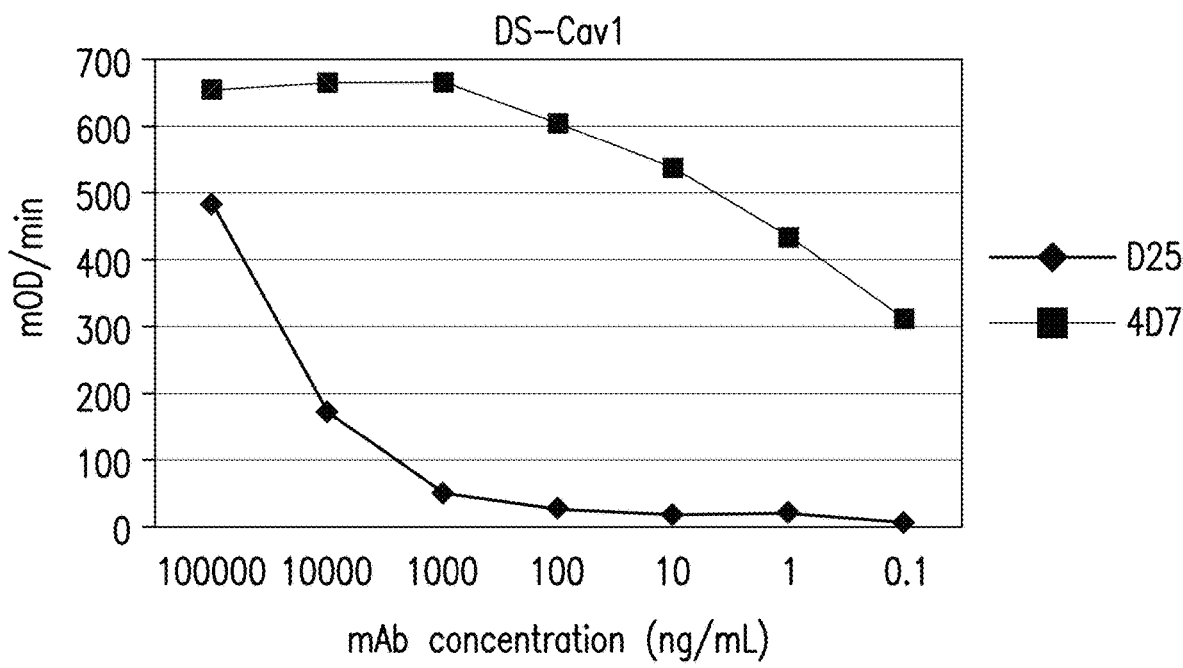
FIGS. 4A-4C show binding of freshly harvested cell culture supernatants of DS-Cav1 (FIG. 4A), LZF57 (FIG. 4B) or LZF111 (FIG. 4C) to D25 and 4D7 monoclonal antibodies as determined by ELISA.
Figure 4B:
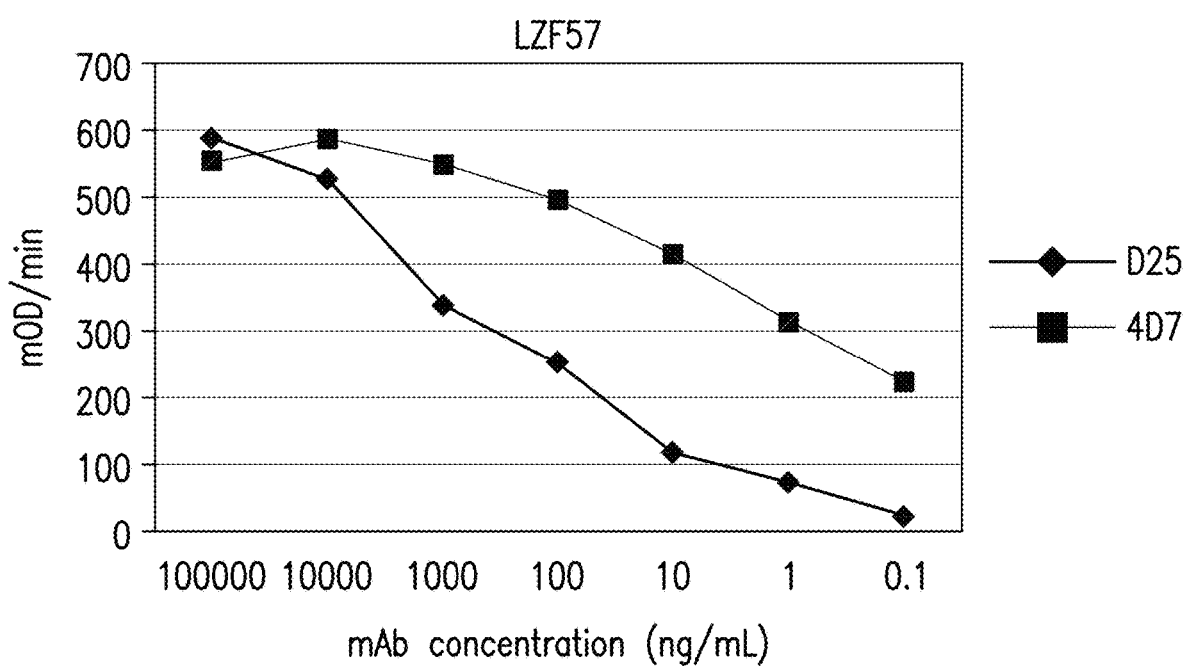
Figure 4C:
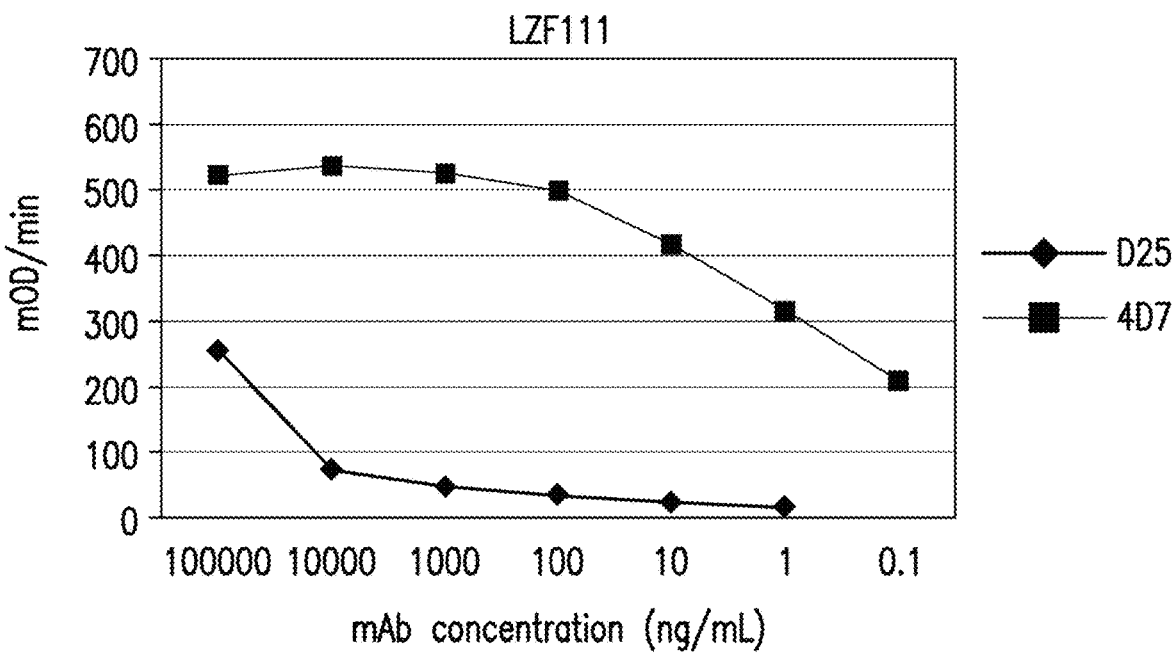
Figure 4D:
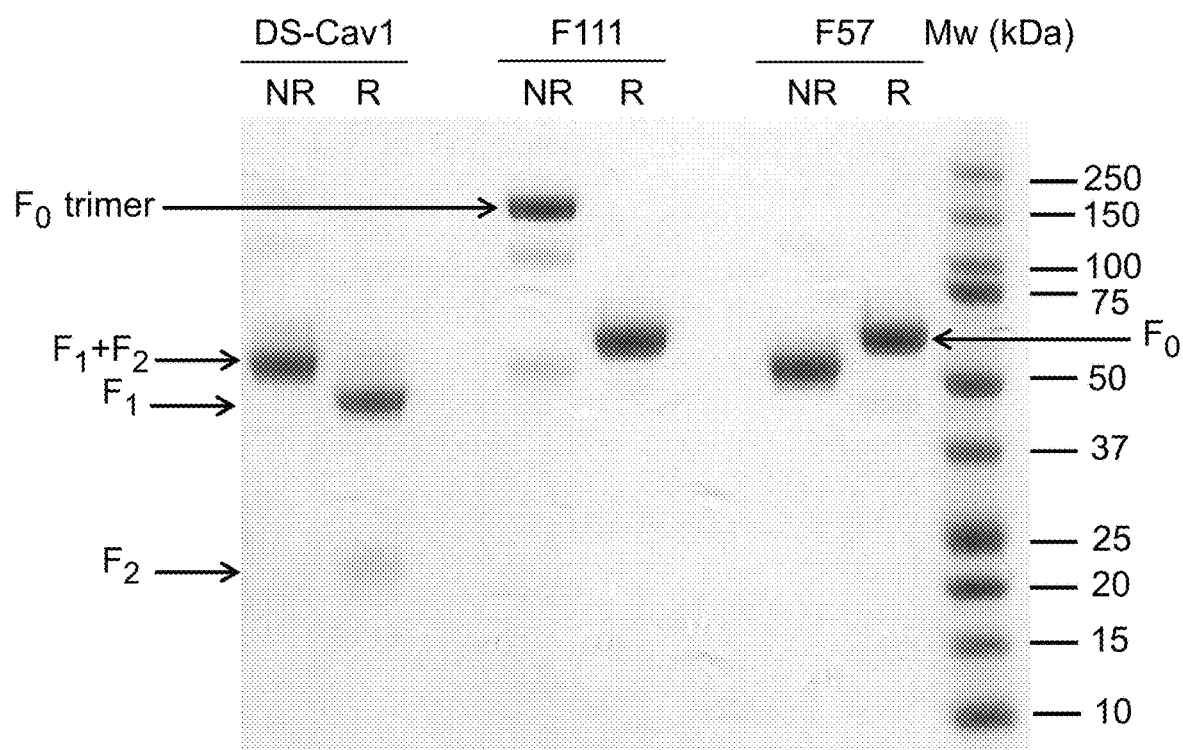
FIG. 4D shows purified DS-Cav1, F57 and F111 analyzed by SDS-PAGE under reducing (R) or non-reducing (NR) conditions.
Figure 10:
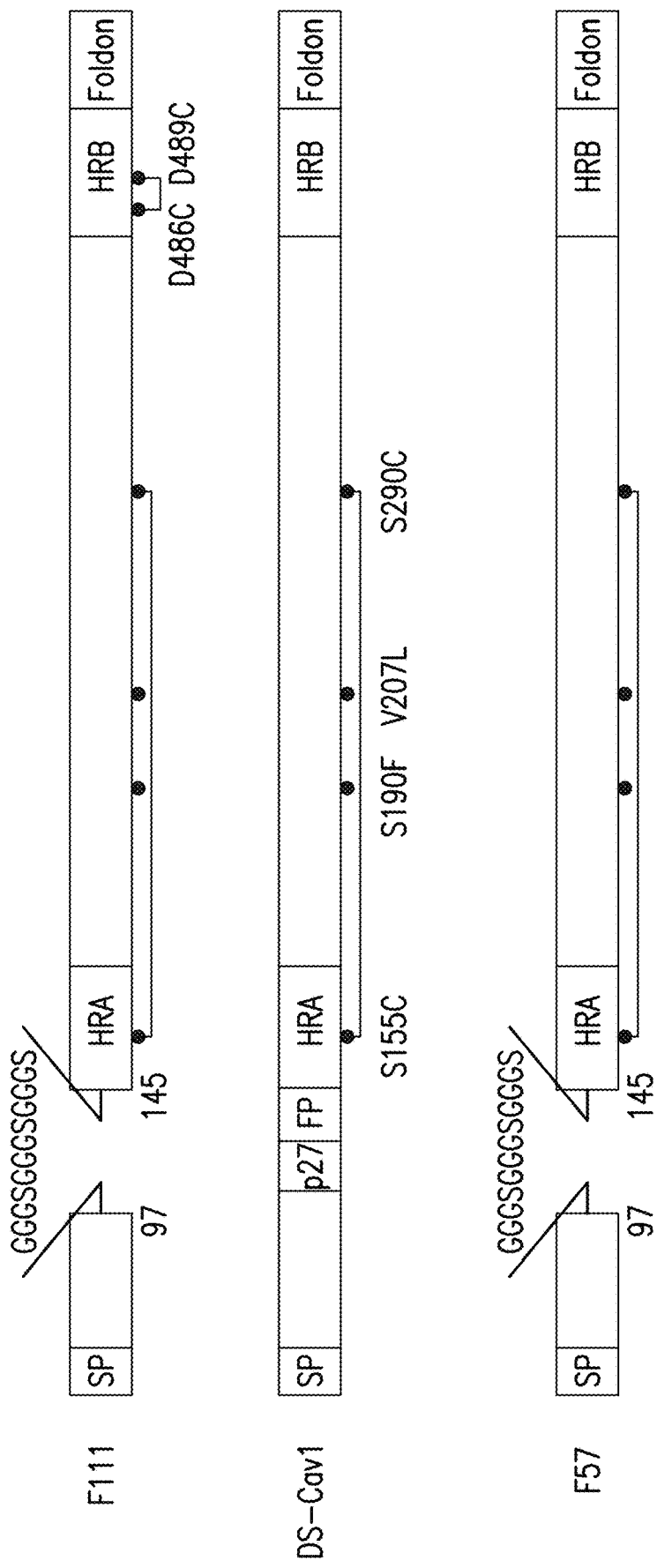
FIG. 10 sets forth a schematic diagram of LZF111 (top), DS-Cav1 (middle) and LZF57 (bottom).

Monoclonal antibody, 4D7, which reacts to antigenic site I on the RSV postfusion F protein and can be used to assess the stability of the prefusion F structure (Flynn et al. 2016). Freshly harvested cell culture supernatants of DS-Cav1 or construct LZF57a were assessed by ELISA for D25 and 4D7 binding (FIG. 4C). Although construct LZF57a retained D25 binding, indicating its prefusion conformation, it appeared to exhibit increased 4D7 binding compared to the original DS-Cav1 construct, suggesting that there might be subtle conformational change when the single chain linker was introduced. To further stabilize the LZF57a single chain RSV mutant construct, structure-based design was performed to generate variants with disulfide bond mutations; cavity filling mutations; and/or postfusion-destabilization mutations. Especially, model of a disulfide mutant D486C/D489C based on crystal structure of the prefusion F protein suggested that an inter-molecular disulfide bond within 3.8 Å might help to further stabilize the prefusion conformation (data not shown). Selected mutations were combined with the LZF57a mutations, and evaluated with prefusion specific mAb D25 and 4D7 as described above. Mutant LZF 111a (which corresponds to LZF57a with D486C/D489C mutation) exhibited decreased 4D7 binding compared to construct LZF57a, suggesting that it might adopt a more prefusion-like conformation (FIGS. 4B, 4C, and 4D). FIG. 10 sets forth the schematic of the LZF111 and LZF57 constructs.

To further characterize the LZF111 mutant, RSV F proteins (DS-Cav1 and LZF111a) were purified from culture supernatants with a modified method adopted from previously described (McLellan 2013). Briefly, his tagged proteins were purified using Ni-Sepharose chromatography (GE Healthcare). Tags were removed by overnight digestion with thrombin. Digestion was performed during dialysis to reduce imidazole concentration. To remove co-eluting contaminants and uncleaved F protein, samples were subjected to a second Ni-Sepharose chromatography step. F proteins were further purified by gel filtration chromatography (Superdex 200, GE Healthcare) and were stored in a buffer of 50 mM HEPES pH 7.5, 300 mM NaCl·SDS-PAGE analysis was performed under reducing and non-reducing conditions to assess the disulfide bond formations (FIG. 4D). In brief, purified protein samples were treated with SDS loading buffer with or without reducing agent (Life Technologies), heated at 95° C. for 2-3 minutes, and applied to NuPAGE (Invitrogen) gel electrophoresis. Gels were stained with Gel Code Blue staining solution (Pierce) and distained with water. Under reducing conditions, DS-Cav1 appeared as two bands on the gel, representing the cleaved F$_1$ and F$_2$ fragments, as expected. Under non-reducing conditions, DS-Cav1 appeared primarily as a band near 50 kDa, representing one cleaved F$_1$ fragment and one F$_2$ fragment held together by native disulfide bonds. As expected, single chain RSV mutant LZF57 appeared primarily as an uncleaved monomeric F$_0$ band on the gel, under either condition. The change in mobility for LZF57 under reducing and non-reducing conditions is most likely caused by a loss of compactness under reducing conditions, leading to an increased apparent molecular weight. Single chain RSV mutant LZF111 also appeared primarily as an uncleaved monomeric F0 band on the gel, under reducing conditions. Under non-reducing conditions, although there are two subdominant lower bands at 50 kDa and 100 kDa consistent with monomeric and dimeric forms, the dominant band for LZF111 is shifted up near 150 kDa, consistent with the molecular weight of a trimer. As the D486C/D489C mutations were the only difference between the LZF57 and LZF111 constructs, this data suggested that the designed inter-molecular disulfide bond indeed forms in the majority of LZF111 molecules.

Example 3: LZF111 Stability Studies

Figure 5A:
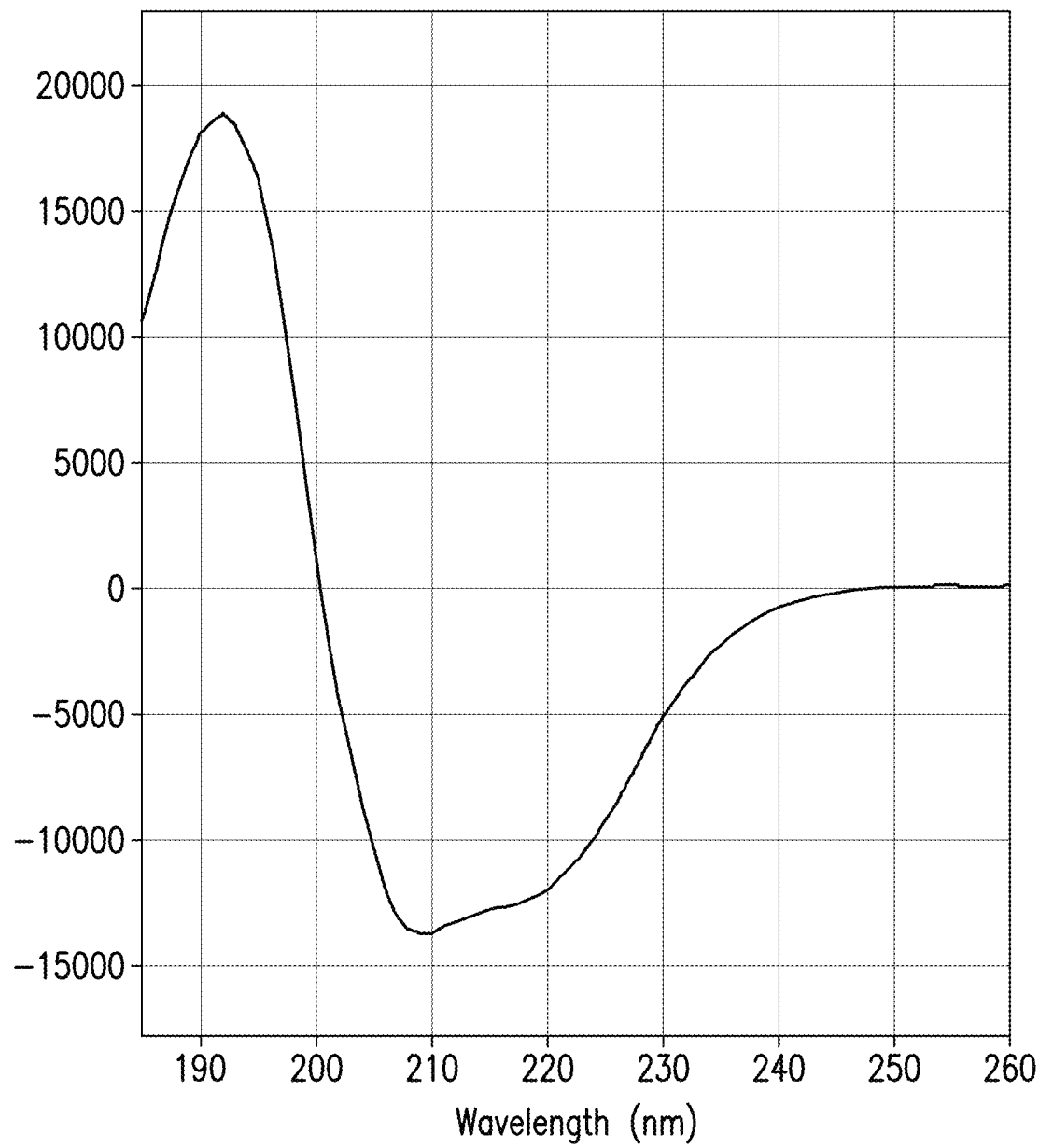
FIGS. 5A and 5B show the CD spectra of LZF111 and DS-Cav1, respectively.
Figure 5B:
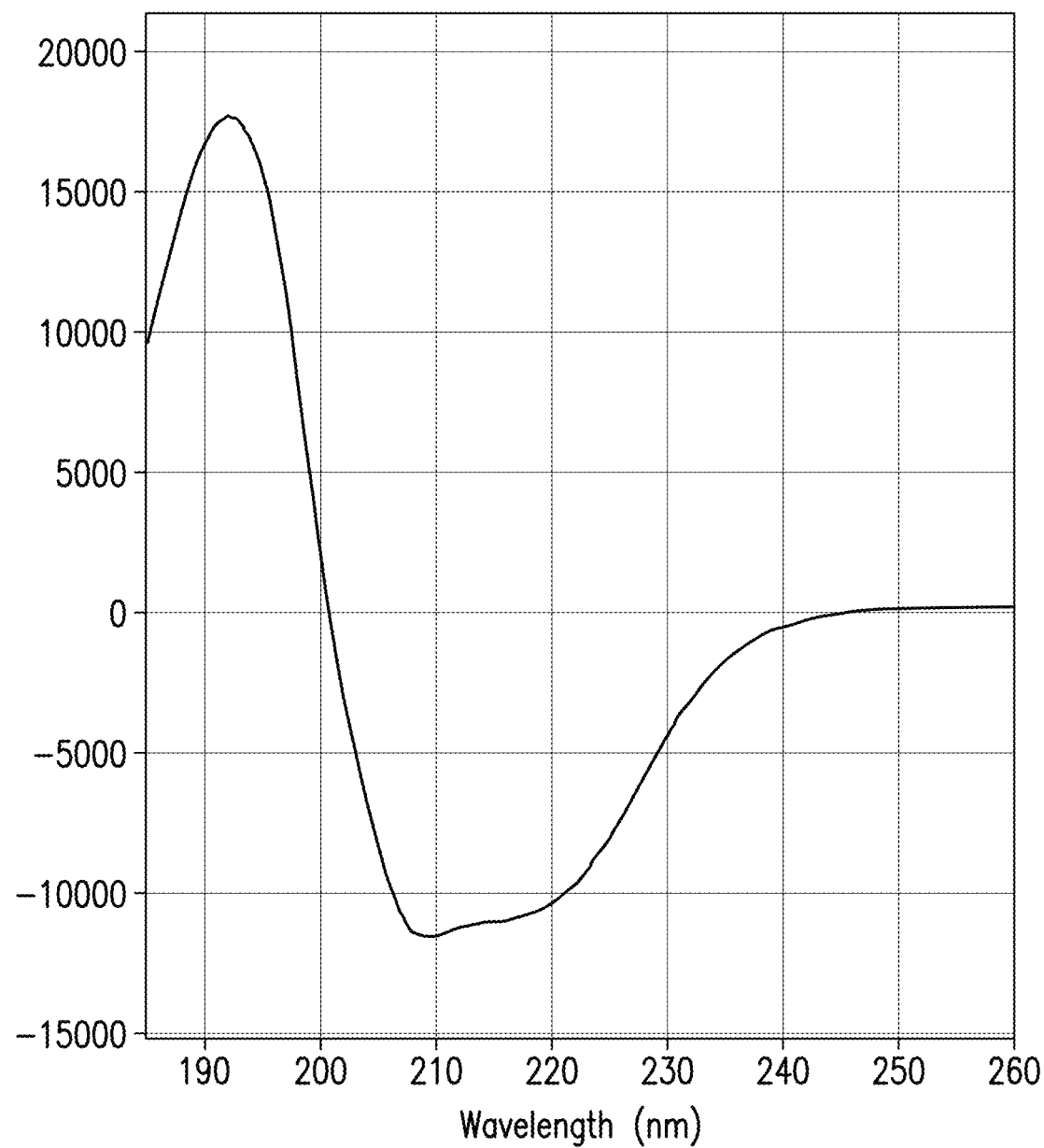
Figure 6:
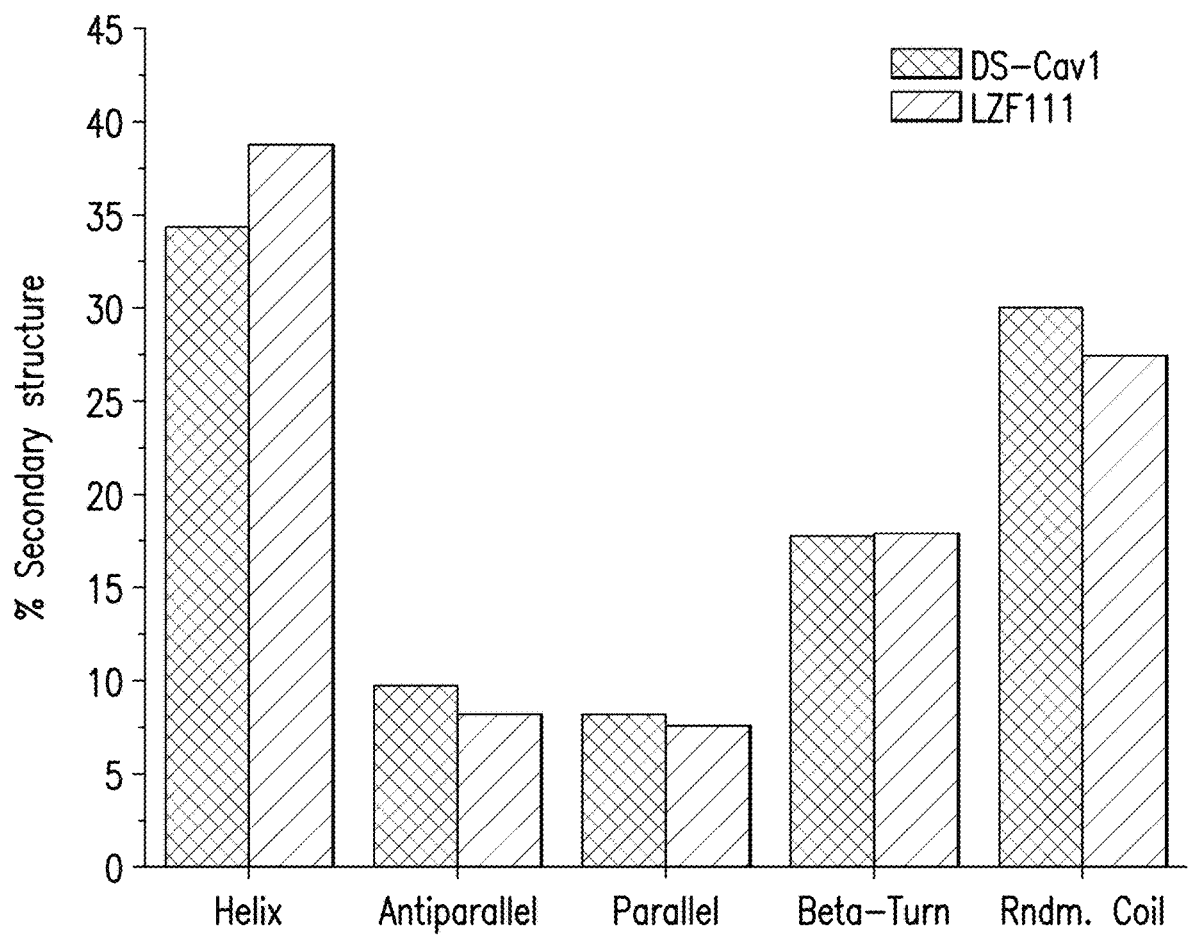
FIG. 6 shows secondary structure analysis by reconstruction of the CD spectra (185 nm to 260 nm) of DS-Cav1 and LZF111 using a neural network that was trained on CD spectra of proteins with resolved 3D structure.

To analyze the secondary structures of purified RSV F proteins, circular dichroism ("CD") spectra were acquired on a Chirascan spectrometer (Applied Photophysics LtD, UK). Samples were analyzed after buffer exchange into 10 mM $Na_2HPO_4$ using Zeba spin columns (Pierce) and subsequent 1:2 dilution into 10 mM $Na_2HPO_4$ yielding a final protein concentration of 3.9 µM and 4.4 µM for DsCav-1 and LZF111, respectively. CD spectra were recorded in undiluted using a quartz cuvette with 0.5 mm path length. The temperature control was set to 20° C. The bandwidth was set to 1 nm. Data points between 185 nm and 260 nm were acquired in 1 nm intervals with 5 s sampling time per time point. Sample and buffer spectra were acquired after 10 minutes of temperature equilibration applying three technical replicates, respectively. Average buffer spectra were subtracted from sample spectra. Resulting data points were smoothed with the Savitzky-Golay algorithm (polynomial order 2, two data points to left and right) using the Origin Pro 7.5 SR7 software package (Origin Lab Corporation). The CD spectra of DS-Cav1 and LZF 111 were almost identical (FIGS. 5A and 5B). Secondary structures were further analyzed by reconstruction of the CD spectra (185 nm to 260 nm) using a neural network that was trained on CD spectra of proteins with resolved 3D structure (software CDNN: Circular Dichroism Neuronal Network) (FIG. 6), indicating that the modifications of LZF111 did not lead to significant changes in secondary structures of the prefusion F protein.

Figure 7:
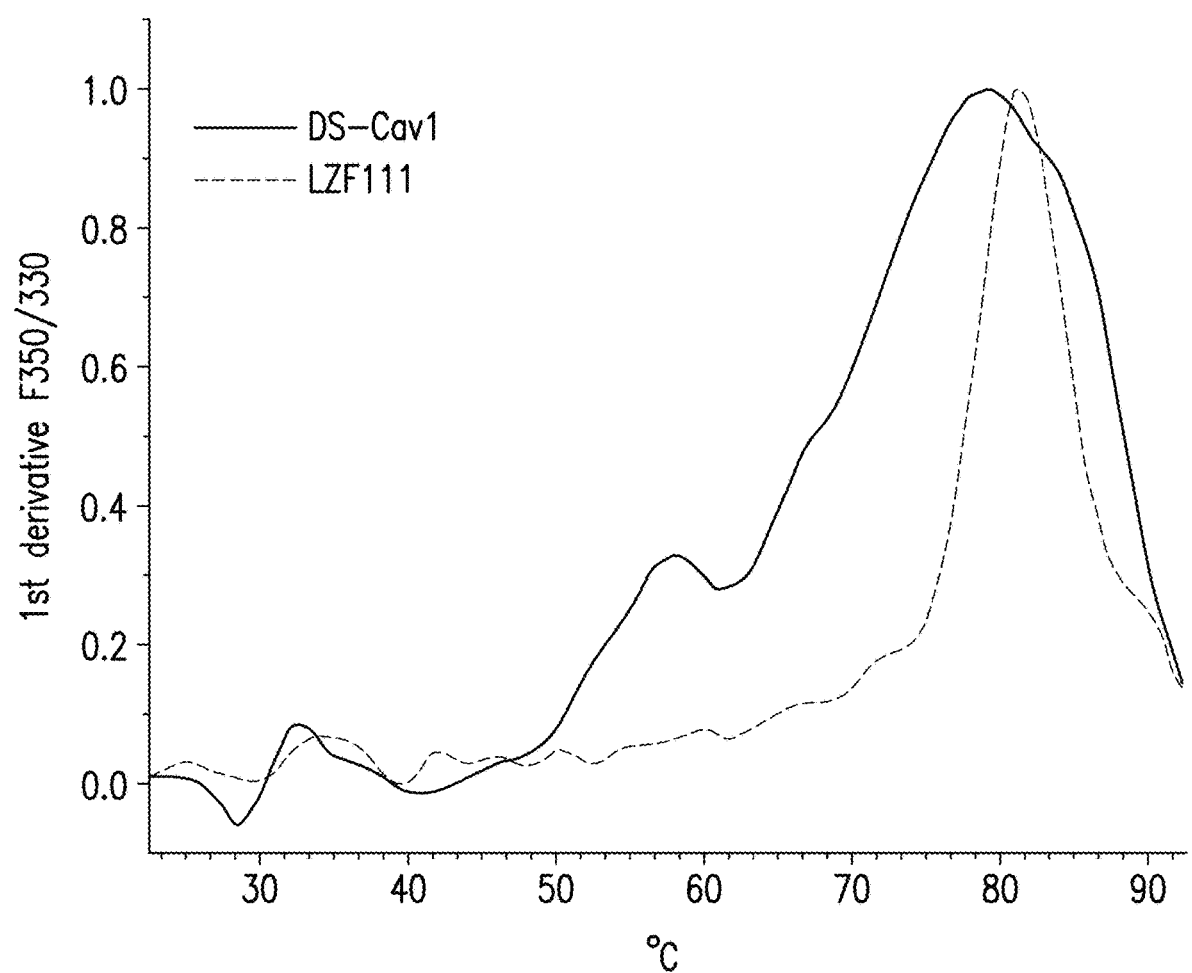
FIG. 7 shows the heat stability of purified LZF111 and DS-Cav1 analyzed by Differential Scanning Fluorimetry (DSF).

Differential scanning fluorimetry (DSF) analyses were performed with DS-Cav1 and LZF111 proteins to evaluate their stability. Solutions of DS-Cav1 protein (0.27-35 µM) in 50 mM HEPES, 300 mM NaCl at pH 7.5 were prepared by serial dilution. The fluorescence signal of each 85 µL protein sample in a micro quartz cuvette with an optical path length of 3 mm×3 mm (Thermo Fisher) was detected using a Cary Eclipse fluorimeter equipped with a Cary temperature controller (Agilent Technologies, CA). The intrinsic protein fluorescence was recorded at 330 nm and 350 nm. The excitation wavelength was set to 280 nm with a slit width of 10 nm. The emission slit width was set to 2.5 nm. The photo multiplier voltage was adjusted before each measurement to values between 500V and 800V to maximize the fluorescence signal. Thermal unfolding experiments were performed using a temperature ramp of 1° C./min from 20° C. to 95° C. in 0.5° C. increments. The sample was equilibrated at the starting temperature for 1 min and fluorescence signals were averaged for each data point for 1.5 s. A multi-cell holder allowed analysis of up to 4 samples simultaneously. Raw data was exported for further processing with Origin Pro®7.5 SR7 to obtain melting curves of fluorescence intensity as a function of temperature. The melting curves were smoothed (polynomial order=1, number of points=12), and peak centers of the first derivative of the ratio between 350 nm and 330 nm were used as melting temperatures (Tm). Data was normalized by the highest signal intensity in order to aid the comparison of different protein samples or protein concentrations. DS-Cav1 has two transition midpoints (60.85±1.98° C. and 80.7±0.93° C.), which were presented as the mean obtained from all protein concentrations analyzed for the same sample type (Flynn et al. 2016) (FIG. 7). For LZF111, the Tm presented (~81° C.) was obtained from a single concentration of 15 µM (FIG. 7). The absence of the lower Tm at ~60.85° C. and the narrower peak for the higher Tm at ~81° C. suggested that LZF111 has improved stability compared to DS-Cav1.

Figure 8A:
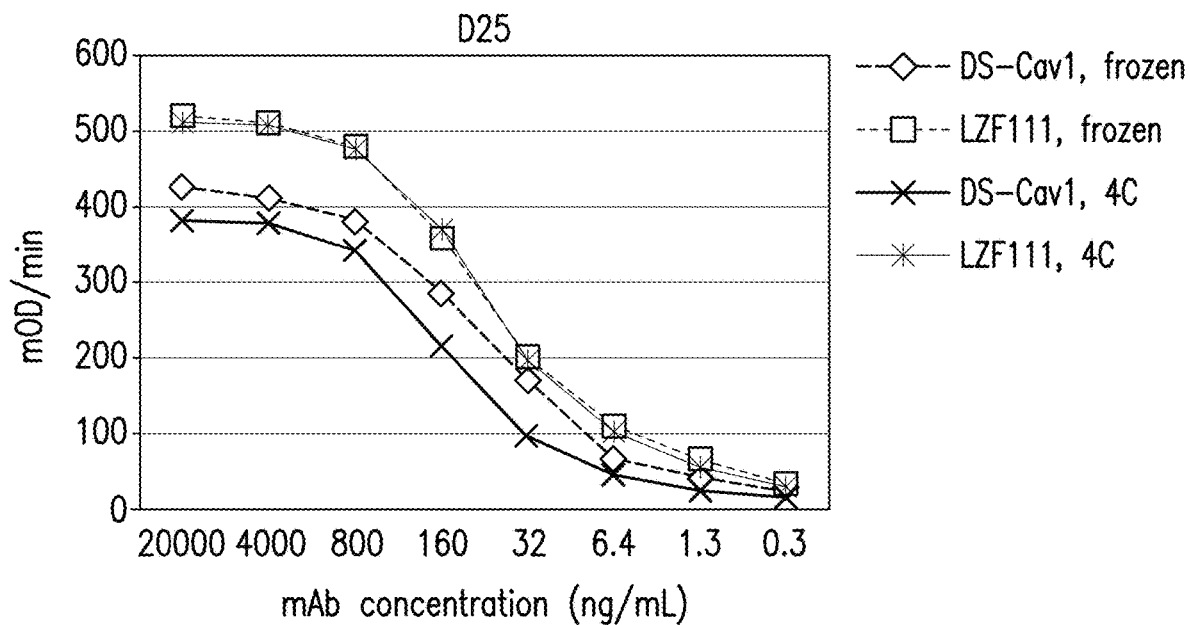
FIGS. 8A-8E show the long-term stability of purified DS-Cav1 protein or LZF111 stored frozen or at 4° C. for 1 (FIGS. 8A-8C), 2 (FIG. 8D), or 3 (FIG. 8E) months, as evaluated by binding to D25, 4D7 and Synagis® (palivizumab) in an ELISA binding assay.
Figure 8B:
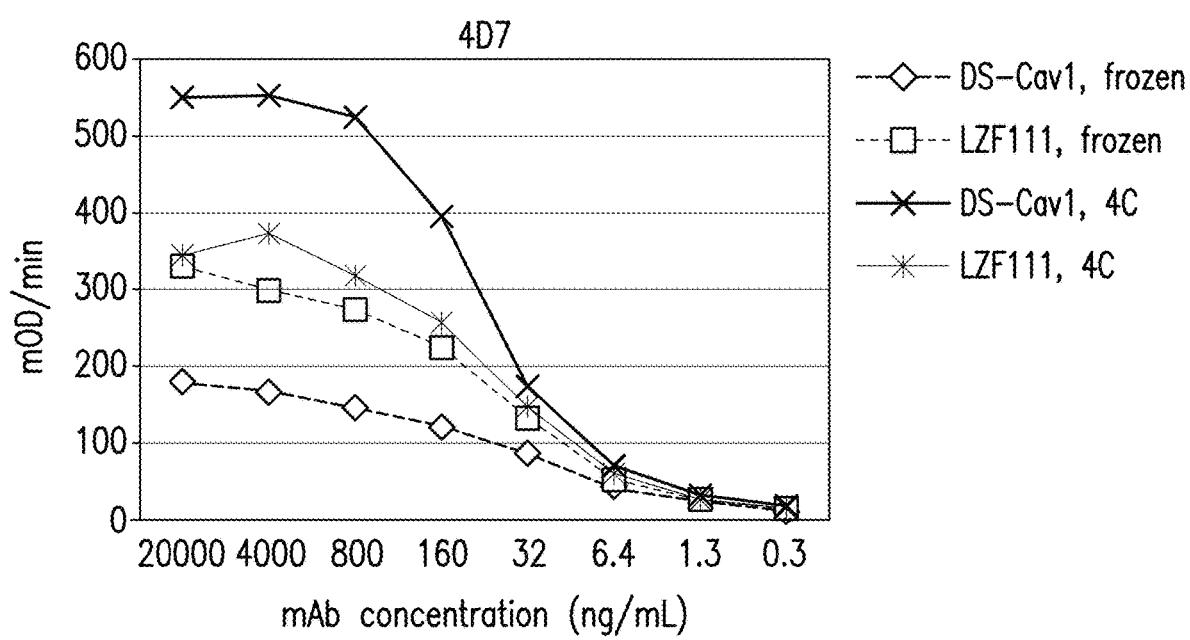
Figure 8C:
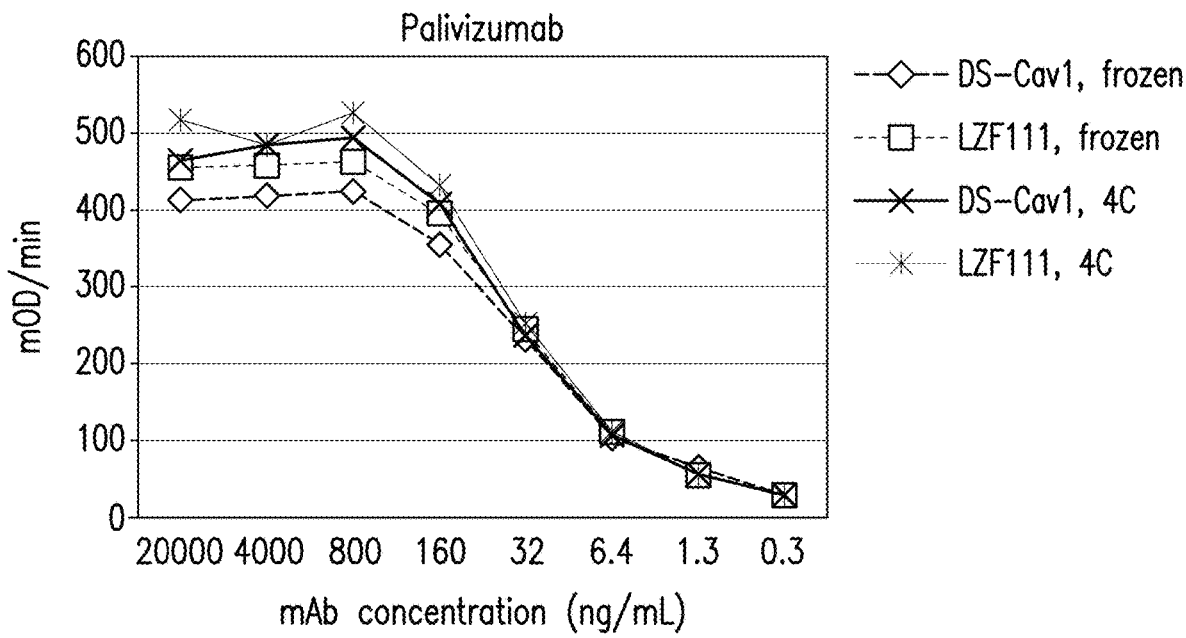
Figure 8D:
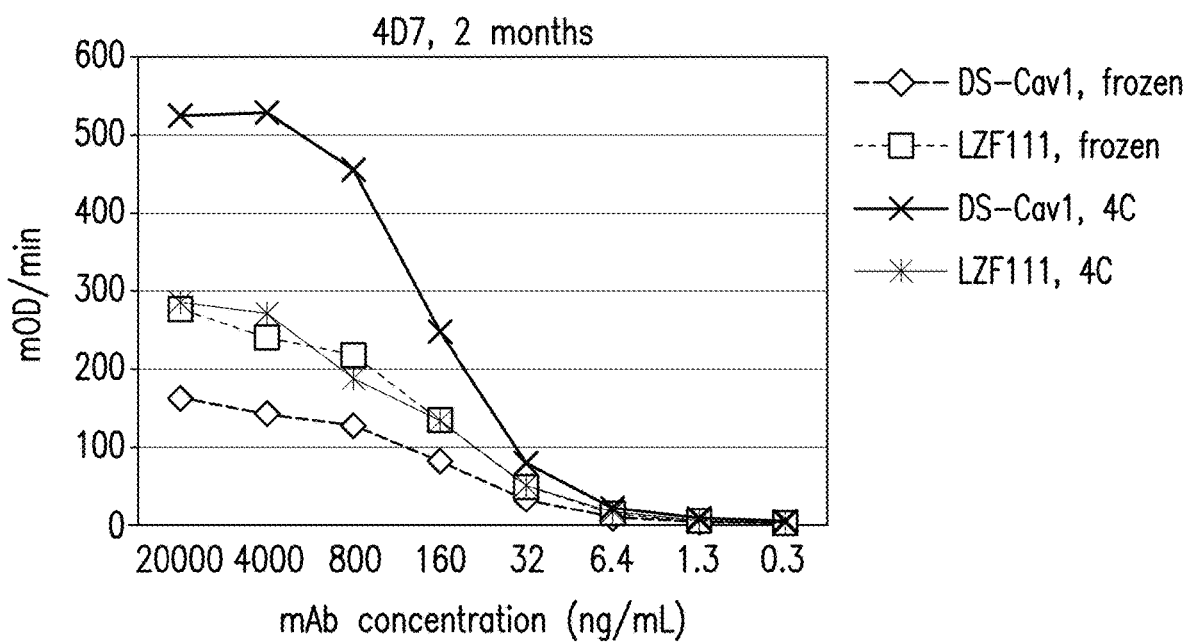
Figure 8E:
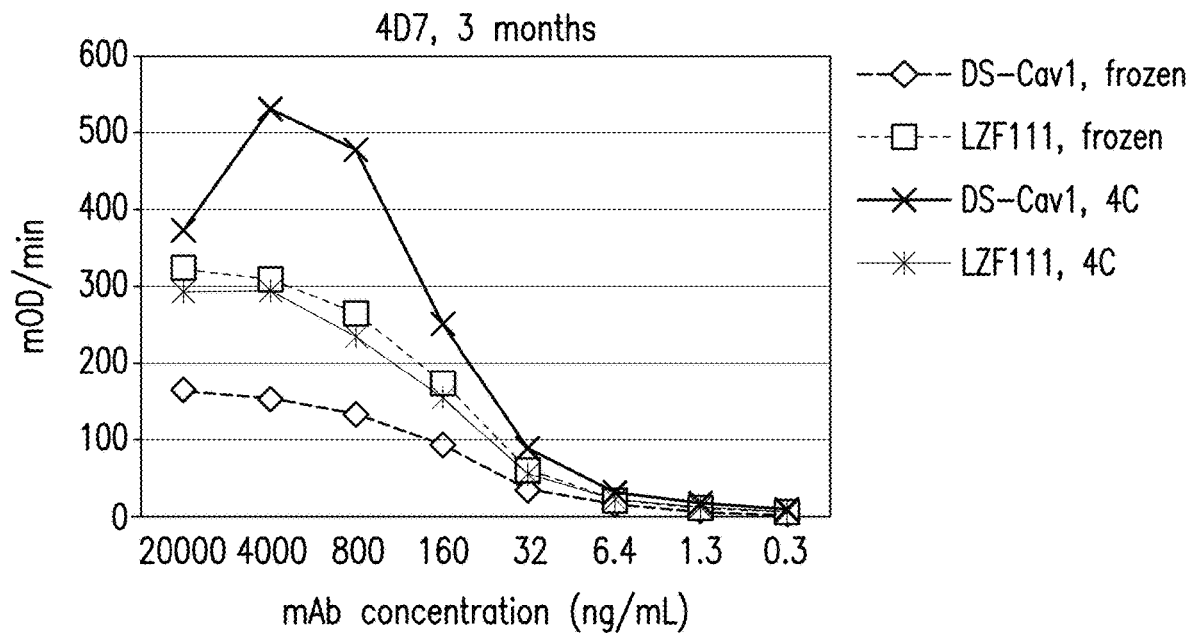

Long-term stability at 4° C. or higher is a desirable attribute for a subunit vaccine antigen. To assess the long-term stability of DS-Cav1, we have previously used antibody binding assays with D25 and 4D7, as well as biophysical analyses. Our data demonstrated that upon long-term storage at 4° C., DS-Cav1 undergoes a conformational change, adopting alternate structures that gain the ability to bind 4D7 (Flynn et al. 2016). To evaluate the long-term stability of LZF111, purified DS-Cav1 protein or construct LZF111 was stored frozen or at 4° C. for 1, 2, or 3 months, and evaluated with D25, 4D7 and palivizumab in an ELISA binding assay. Briefly, purified proteins were diluted to 1 µg/mL with PBS and coated on 96-well ELISA plate (NUNC) overnight at 4° C. Unbound sites were blocked by addition of 2% (v/v) bovine serum albumin (BSA) in PBS and incubation for 1 hour at room temperature. Plates were washed with PBS containing 0.05% (v/v) Tween® 20 (polysorbate 20) (PBS-T) and incubated with serial dilutions of antibodies (D25 or palivizumab) at room temperature for 1 hour. Plates were washed again with PBS-T and incubated for 1 hour at room temperature with goat anti-human (for D25 and palivizumab) or anti-mouse (for 4D7) IgG HRP-conjugated secondary antibody (Thermo Fisher) diluted 1:2,000. Following an additional wash with PBS-T and brief rinse with $ddH_2O$, Super AquaBlue ELISA substrate (eBiosience) was added, and the plate was immediately read at 405 nm for 5 min. mOD/min was calculated for each well. FIGS. 8A, 8B and 8C show that after 1 month storage at 4° C., while D25 and palivizumab relativities were maintained for both constructs, a significant increase in 4D7 binding was detected with DS-Cav1, but not with the improved LZF111. Furthermore, no increased 4D7 binding was observed with LZF111 after 2 and 3 months storage at 4° C. (FIGS. 8D and 8E), suggesting that long term stability of LZF111 is superior to DS-Cav1.

Example 4: Immunogenicity Studies

Figure 9A:
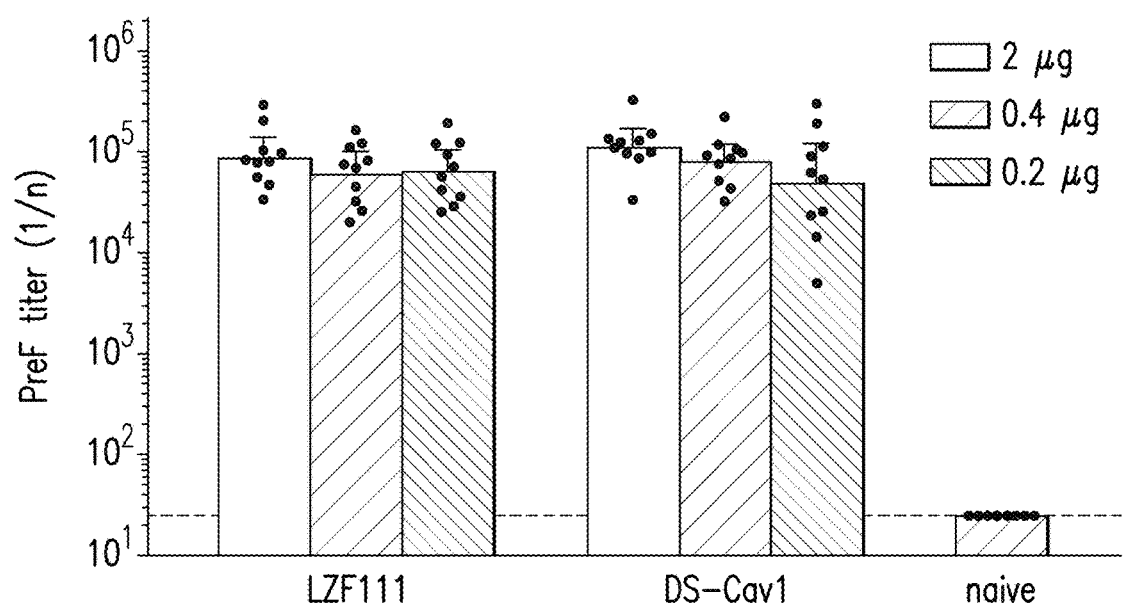
FIGS. 9A and 9B show ED10 ELISA titers of PD2 mice sera against prefusion F protein (FIG. 9A) and serum neutralization titers of PD2 mice sera against RSV Long strain (FIG. 9B). Horizontal dashed line indicates limit of detection. Data shows that LZF111 induced similar levels of neutralizing antibodies as compared to DS-Cav1 across different doses.

A mouse immunogenicity study was designed to compare the immunogenicity of DS-Cav1 and LZF111 subunit vaccines. Animals tested were female BALB/c mice obtained from Charles River Laboratories. 10 mice per group were immunized twice with three different doses (2 µg, 0.4 µg and 0.2 µg) of either purified DS-Cav1 or LZF 111a proteins with aluminum adjuvants at weeks 0 and 3. Bleeds were collected 2 weeks after each immunization and sera were analyzed. To assess binding antibody titers against prefusion F protein, immulon12HB microtiter plates (NUNC) were coated with 2 µg/mL purified recombinant RSV F protein DS-Cav1, and incubated at 4° C. overnight. The plates were then washed and blocked for 1 hour with PBS-T containing 3% non-fat milk (blocking buffer) at room temperature. Test samples were serially diluted 4-fold in blocking buffer (starting at 1:50 dilution), transferred to the RSV F coated plates, and incubated for 2 hours at room temperature. Following three washes with PBS-T, HRP conjugated anti-mouse IgG secondary antibody (Invitrogen) diluted 1:3,000 in blocking buffer was added to the plates and incubated for an additional 1 hour. Plates were washed again and developed with SuperBlu Turbo TMB (Virolabs) in the dark. The reaction was stopped after 5 minutes and absorbance was read at 450 nm on a VersaMax ELISA microplate reader (Molecular Devices). ED10 ELISA titers, which indicated the effective dilution of the serum sample that gives 10% of the maximum signal, were determined by four parameter curve fit in GraphPad Prism 7 software. FIG. 9A shows the ED10 ELISA titers against prefusion F protein of post dose 2 sera. The bottom horizontal dashed line indicates limit of detection. Data showed that LZF111 induced similar anti-prefusion F antibody levels compared to DS-Cav1 across different doses.

Figure 9B:
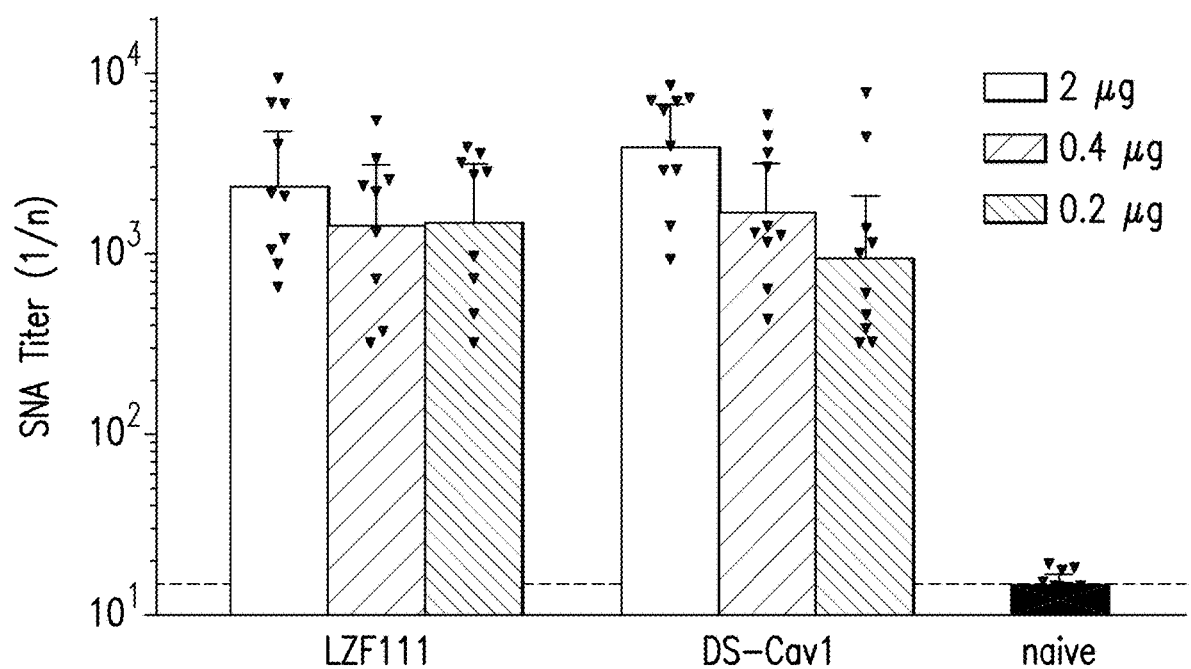

Neutralization assay was also performed on mouse sera that were treated at 56° C. for 30 min to inactivate complement prior to testing. Two-fold serial dilutions of serum samples were prepared in EMEM containing 2% FBS starting at 1:4 dilution. Diluted serum was added in duplicate to 96-well plates and mixed with RSV Long strain (100 pfu/mL) in 100 μl total volume. The mixture of virus and serum samples was incubated for 1 hour at 37° C. with 5% $CO_2$. Following incubation, Hep-2 cells at a concentration of $1.5 \times 10^4$ cells per well were added. The plates were incubated for 3 days at 37° C. with 5% $CO_2$. The cells were then washed and fixed with 80% acetone for 15 minutes. RSV infected cells were then immunostained. Briefly, RSV F- and N-specific monoclonal antibodies were added to the test plates with fixed cells and incubated for 1 hour at room temperature. After washing, biotinylated goat anti-mouse IgG was added and incubated for 1 hour. The plates were washed again and developed by a dual channel near infrared detection (NID) system. Infrared dye-Streptavidin to detect RSV specific signal and two cell stains for assay normalization were added to the 96-well plates and incubated for 1 hour in the dark. Plates were washed, dried in the dark for 20 minutes, and read on the Licor Aerius 1 Automated Imaging System utilizing a 700 channel laser for cell normalization and an 800 channel laser for detection of RSV specific signal. The 800/700 ratios were calculated and serum neutralizing titers (IC50) were determined by four parameter curve fit in GraphPad Prism 7 software. Serum neutralization titers of PD2 sera against RSV Long strain were shown in FIG. 9B. The bottom horizontal dashed line indicates limit of detection. Data showed that LZF111 induced similar levels of neutralizing antibodies compared to DS-Cav1 across different doses.

Example 5: Cotton Rat Immunogenicity Study

In this example, assays were carried out to test the immunogenicity and efficacy of mRNA/LNP vaccines in the cotton rat RSV challenge model. More specifically, female *Sigmodon hispidus* cotton rats were used and immunizations began at 6-7 weeks of age. The mRNA vaccines used were generated and formulated in lipid nanoparticles. The mRNA vaccines evaluated in this study included:
  MRK-04 membrane-bound DS-Cav1 (stabilized prefusion F protein)
  MRK-04_nopolyA_3 mut membrane-bound DS-Cav1 (stabilized prefusion F protein)
  mVRC-1 (v2) membrane-bound single chain sc9 mDS-Cav1, A149C, Y458C (stabilized prefusion F protein)
  mLZF-111 membrane-bound single chain mDS-Cav1, D486C, D489C (stabilized prefusion F protein)

Groups of 8 cotton rats were immunized intramuscularly with 100 μL of vaccine, delivered with 50 μL injections into each quadriceps. The groups were vaccinated with the following vaccines:

| Group | Vaccine | Conc (μg/ml) | Dose (μg) |
|---|---|---|---|
| 1 | None | NA | NA |
| 2 | MRK-04, I.M. | 250 | 25 |
| 3 | MRK-04_nopolyA_3mut, I.M. | 250 | 25 |
| 4 | MRK-04_nopolyA_3mut, I.M. | 50 | 5 |
| 5 | MRK-04_nopolyA_3mut, I.M. | 10 | 1 |
| 6 | mVRC-1 (v2), I.M. | 250 | 25 |
| 7 | mVRC-1 (v2), I.M. | 50 | 5 |
| 8 | mVRC-1 (v2), I.M. | 10 | 1 |
| 9 | mLZF-111, I.M. | 250 | 25 |
| 10 | mLZF-111, I.M. | 50 | 5 |
| 11 | mLZF-111, I.M. | 10 | 1 |

The animals were immunized on day 0 and day 28 of the experiment. On days 28 and 56, blood was drawn from each animal and used for serological assays. On day 56, the cotton rats were challenged intranasally with $1 \times 10^{5.5}$ PFU RSV A2. Four days post inoculation, animals were sacrificed by $CO_2$ inhalation and lung (left lobes) and nasal turbinates were removed and homogenized in 10 volumes of Hanks Balanced Salt Solution (Lonza) containing SPG on wet ice. The samples were clarified by centrifugation at 2000 rpm for 10 minutes, aliquoted, flash frozen, and immediately stored frozen at −70° C.

RSV Neutralization Assay:

Cotton rat sera from each animal was evaluated for neutralization of RSV-A (Long strain) using the following procedures:
  1. All sera samples were heat inactivated by placing in dry bath incubator set at 56° C. for 30 minutes. Samples and control sera were then diluted 1:3 in virus diluent (2% FBS in EMEM) and duplicate samples were added to an assay plate and serially diluted.
  2. RSV-Long stock virus was removed from the freezer and quickly thawed in 37° C. water bath. Viruses were diluted to 2000 pfu/mL in virus diluent
  3. 50 μL of diluted virus was added to each well of the 96-well plate, with the exception of one column of cells, which used as a "no-virus" control
  4. HEp-2 cells were trypsinized, washed, resuspended at $1.5 \times 10^5$ cells/ml in virus diluent, and 100 mL of the suspended cells were added to each well of the 96-well plate. The plates were then incubated for 72 hours at 37° C., 5% $CO_2$.
  5. Following the 72-hour incubation, the cells were washed with PBS, and fixed using 80% acetone dissolved in PBS for 10-20 minutes at 16-24° C. The fixative was removed and the plates were allowed to air-dry.
  6. Plates were then washed thoroughly with PBS+0.05% Tween. The detections monoclonal antibodies, 143-F3-1B8 and 34C9 were diluted to 2.5 □g/mL in assay diluent (1% BSA-PBS-0.1% Tween), and 50 μL of the diluted antibodies were added to each well of the 96-well plate. The plates were then incubated in a humid chamber at 16-24° C. for 60-75 minutes on rocker
  7. Following the incubation, the plates were thoroughly washed.

Figure 11:
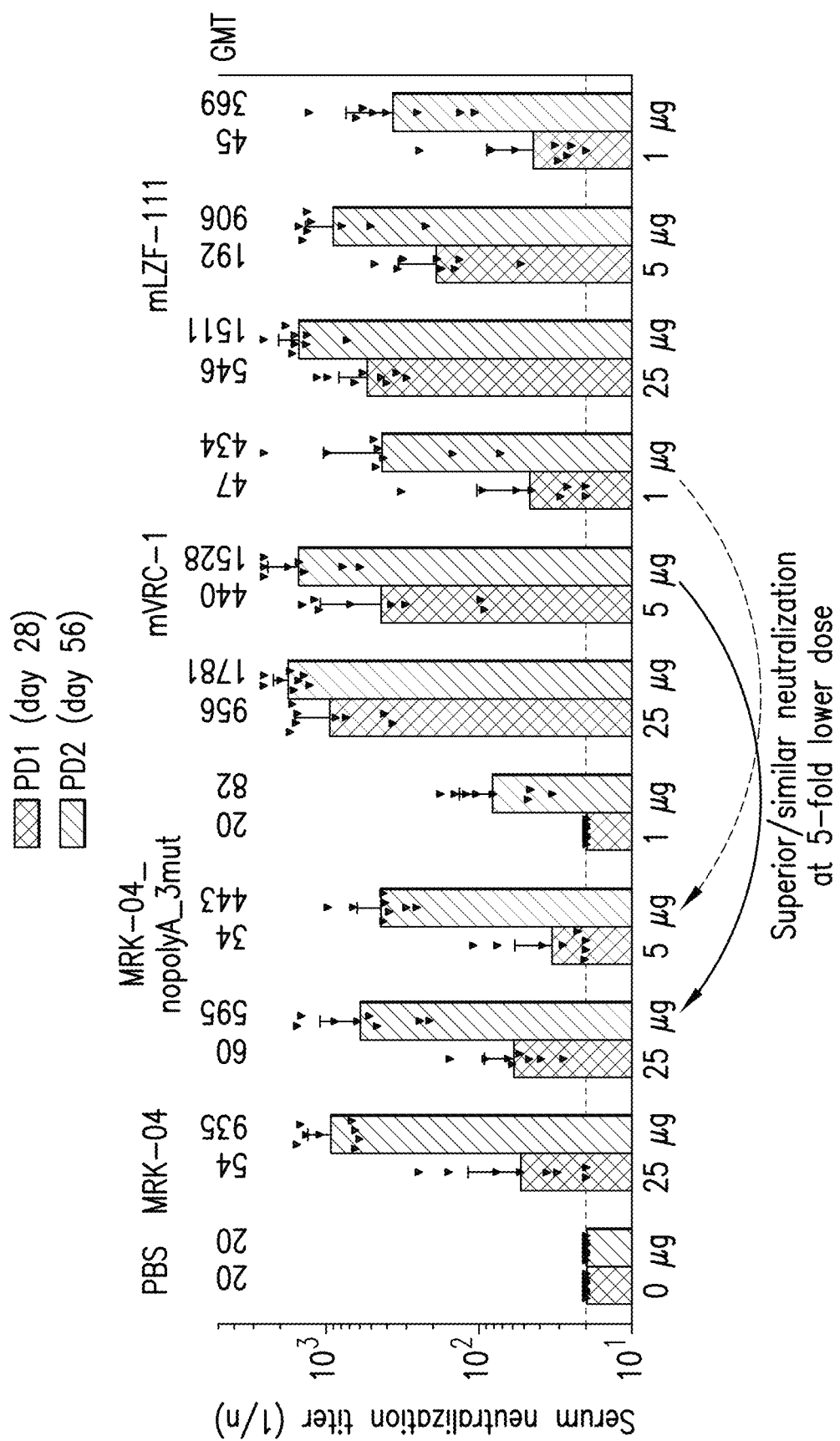
FIG. 11 sets forth serum neutralizing antibody titers ($NT_{50}$ Individual and GMT with 95% Confidence Intervals) to RSV A induced in Cotton Rats by mRNA Vaccines and Control Formulas.

8. Biotinylated horse anti-mouse IgG was diluted 1:200 in assay diluent and added to each well of the 96-well plate. Plates were incubated as above and washed.
9. A cocktail of IRDye 800CW Streptavidin (1:1000 final dilution), Sapphire 700 (1:1000 dilution) and 5 mM DRAQ5 solution (1:10,000 dilution) was prepared in assay diluent and 50 mL of the cocktail was added to each well of the 96-well plate. Plates were incubated as above in the dark, washed, and allowed to air dry.
10. Plates were then read using an Aerius Imager. Serum neutralizing titers were then calculated using a 4 parameter curve fit in Graphpad Prism.
    The titers determined post dose 1 (day 28) and post dose 2 (day 56) are shown in FIG.
11. It was found that the neutralizing titers were elicited in a dose dependent manner for all mRNA vaccines. All mRNA vaccines resulted in increased titers after a second dose regardless of the dose evaluated. Both mVRC-1 (v2) and mLZF111 induced higher titers then MRK-04 and MRK-04_nopolyA_3 mut demonstrating superior or similar serum neutralizing titers at a 5-fold lower dose.

Competition alphaLISA

The immune response to specific epitopes on RSV F-protein for neutralizing antibodies was characterized. The antigenic site II is the binding site for palivizumab, a monoclonal antibody developed for the prevention of lower respiratory infection with RSV in at risk infants and toddlers. Antigenic site ø is a binding site for more potent neutralizing antibodies that are elicited by natural infection with RSV. Additionally, we have generated an antibody (4D7) that targets site I, an epitope not presented in the prefusion conformation. Therefore, in contrast to D25, elicitation of 4D7-competing antibodies would suggest the in vivo generation of postF-like proteins. A competition alphaLISA was developed to characterize the antigenic site ø, antigenic site I and antigenic site II response to the various mRNA-based vaccines.

To measure competing antibody titers, 10 ul of samples serially diluted in HiBlock buffer (PerkinElmer) are placed in a 384 well alphaLISA plate. Diluted samples are mixed with 5 μl of AlphaLISA acceptor beads (100 ug/ml) that has been previously conjugated to a prefusion-stabilized RSV F protein (DS-Cav1) or a postfusion RSV F protein (RSV F wt). After 30 min incubation at room temperature, 10 ul of biotinylated D25, palivizumab, or 4D7 antibody diluted in Hiblock buffer is added to every well. After additional 30 min incubation, 25 ul of streptavidin-donor beads (20 μg/ml) in HiBlock buffer is added to each well and incubated for 30 min in the dark. Plate is then read on an EnVision_Alpha Reader (615 nm detection).

Figure 12:
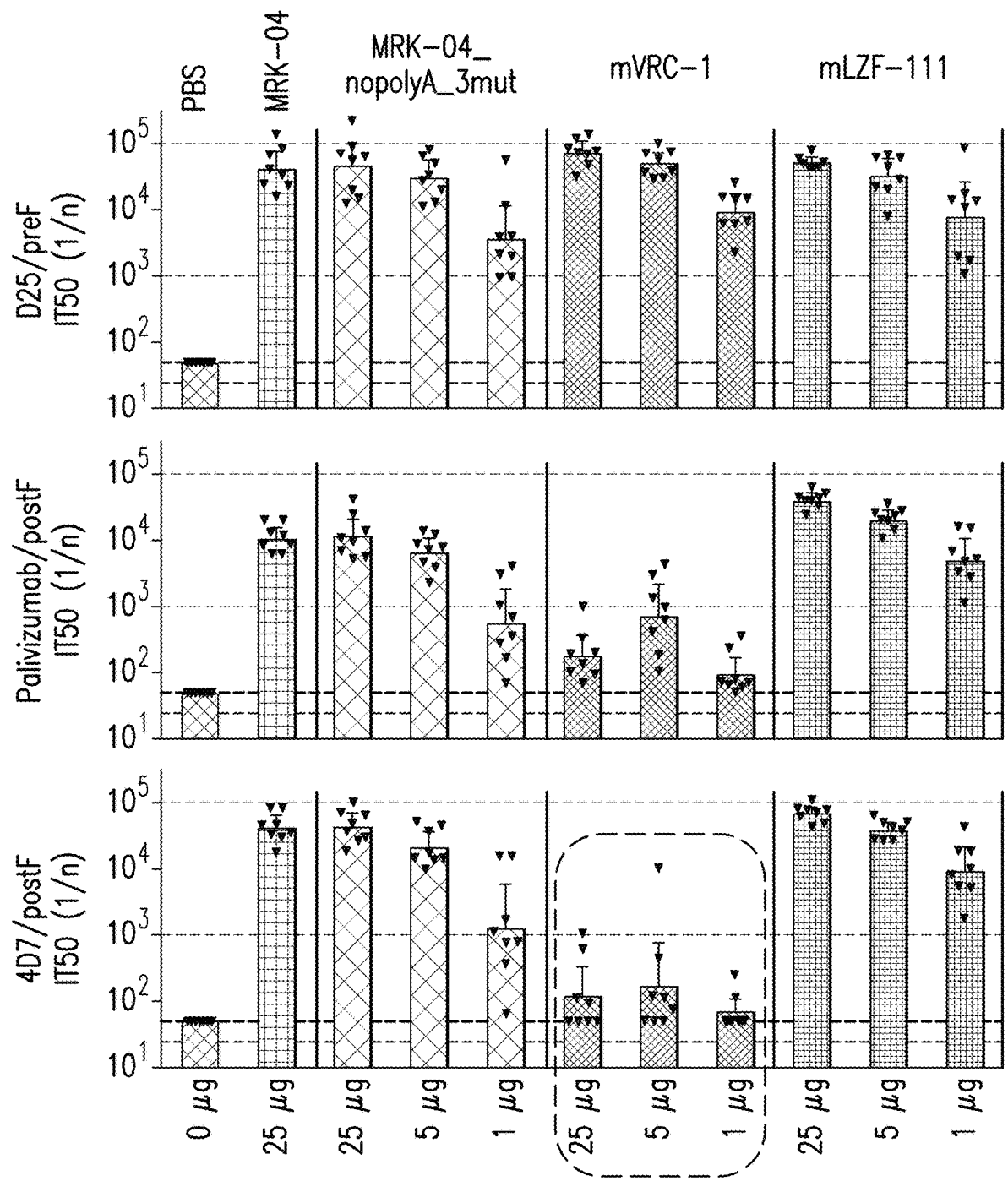
FIG. 12 sets forth serum antibody competition ELISA titers ($IT_{50}$ Individual and GMT with 95% Confidence intervals) against D25 (site ø), palivizumab (site II), and 4D7 (site I) measured at Day 56 (4 weeks PD2).

The palivizumab, D25, and 4D7 competing antibody titers measured on Day 56 (4 weeks PD2) are presented in FIG. 12. The competition data revealed that mVRC-1 (v2) induced lower levels of 4D7-postfusion F competing antibodies, while D25-prefusion titers and palivizumab titers are not affected. This different competition profile correlates with mVRC-1 (v2) mRNA expressing a more prefusion stabilized protein than MRK-04_nopolyA_3 mut and mLZF-111.

C. Cotton Rat Challenge Results

Procedures for measuring RSV titers in the cotton rat lung and nose homogenates are described below. Lung and nose homogenates were clarified by centrifugation and diluted 1:10 and 1:100 in EMEM. Confluent HEp-2 monolayers were infected in duplicates with 50 μl per well starting with undiluted (neat) samples followed by diluted homogenates in 24-well plates. After one hour incubation at 37° C. in a 5% $CO_2$ incubator, wells were overlaid with 0.75% methylcellulose medium and plates restored into the 37° C. incubator. After 4 days of incubation the overlay was removed and the cells were fixed with 0.1% crystal violet stain for one hour, then rinsed, and air-dried. Plaques were counted and virus titers were expressed as plaque forming units per gram of tissue.

Figure 13:
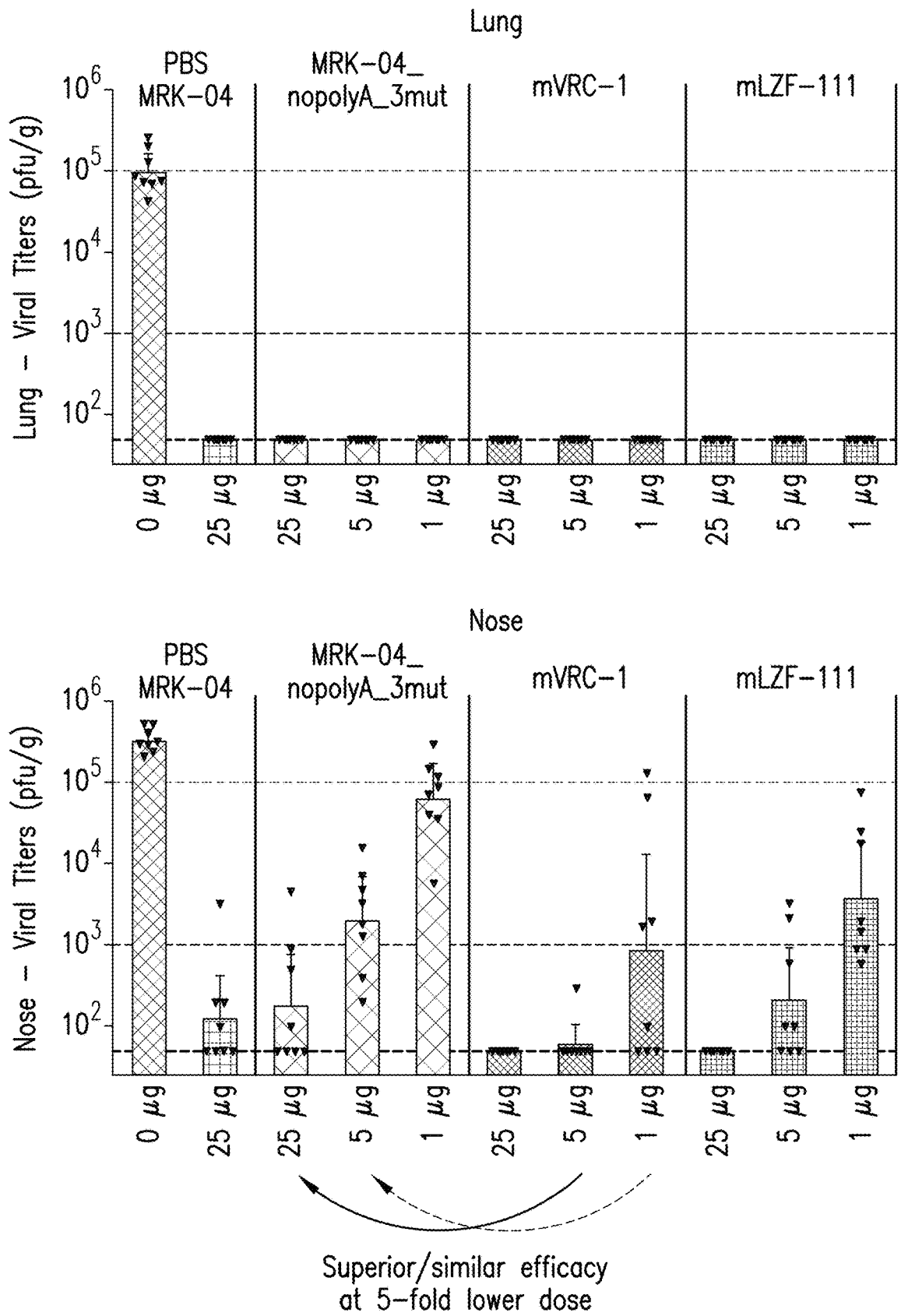
FIG. 13 sets forth RSV content in Lung and Nose after challenge of Cotton rats with RSV A.

To assess vaccine-mediated protection, viral titers were measured in lung and nose 5 days after challenge. All mRNA vaccines achieved total protection in the lung, but mVRC-1 (v2) and mLZF111 showed improved protection in the nose, demonstrating superior or similar efficacy to MRK-04 and MRK-04_nopolyA_3 mut, at a 5-fold lower dose (FIG. 13).

Example 6: African Green Monkey Immunogenicity and Efficacy

In this example, assays were carried out to test the immunogenicity and efficacy of mRNA/LNP vaccines in the African Green Monkey RSV challenge model.

More specifically, male and female adult African Green Monkeys with body weights ranging from 1.6 to 2.65 kg, which were confirmed to be RSV-negative by neutralizing antibody titer, were used. The mRNA vaccines used were generated and formulated in lipid nanoparticles. The mRNA vaccines evaluated in this study included:
  MRK-04_nopolyA_3 mut membrane-bound DS-Cav1 (stabilized prefusion F protein)
  mVRC-1 (v2) membrane-bound single chain sc9 mDS-Cav1, A149C, Y458C (stabilized prefusion F protein)
  mLZF-111 membrane-bound single chain mDS-Cav1, D486C, D489C (stabilized prefusion F protein)

Groups of 4 African Green Monkeys were immunized intramuscularly with 500 μL of vaccine into one deltoid. The groups were vaccinated with the following vaccines as out in Table 1.

TABLE 1

Vaccine Formulations Tested for Immunogenicity in African Green Monkeys

| Group | Vaccine | Conc (μg/ml) | Dose (μg) |
| --- | --- | --- | --- |
| 1 | MRK-04_nopolyA_3mut, I.M. | 50 | 25 |
| 2 | MRK-04_nopolyA_3mut, I.M. | 10 | 5 |
| 3 | mVRC-1 (v2) | 50 | 25 |
| 4 | mVRC-1 (v2) | 10 | 5 |
| 5 | mLZF-111 | 50 | 25 |
| 6 | mLZF-111 | 10 | 5 |
| 7 | RSV A2 5.51og10pfu, I.N. | NA | NA |
| 8 | None | NA | NA |

The animals were immunized on day 0, day 28, and day 56 of the experiment. On days 0, 14, 28, 42, 56, and 70, blood was drawn from each animal and used for serological assays. On day 70, the African Green Monkeys were challenged intranasally with $1 \times 10^{5.5}$ PFU RSV A2. Nasopharyngeal swabs were collected on days 1-14 post challenge, and lung lavage samples were collected on days 3, 5, 7, 9, 12 and 14 post challenge to test for viral replication.

Figure 14:
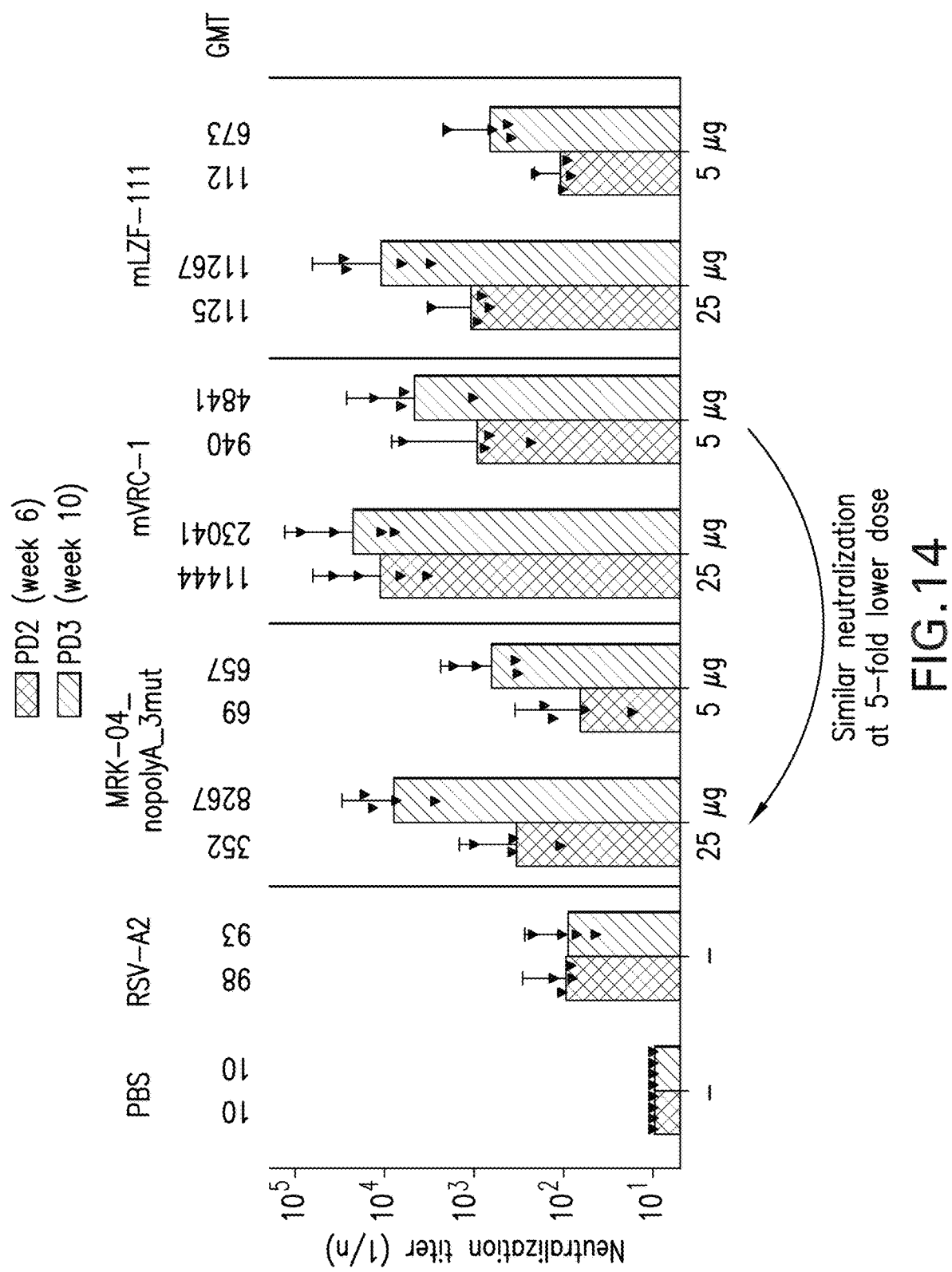
FIG. 14 sets forth serum neutralizing antibody titers ($NT_{50}$ Individual and GMT with 95% Confidence Intervals) to RSV A induced in African Green Monkeys by mRNA vaccines and control formulations.

A. RSV Neutralization Assay:

Monkey sera from each animal were evaluated for neutralization of RSV-A (Long strain) as described above. The $NT_{50}$ titers determined post dose 1 and post dose 2 are shown in FIG. 14. Titers were seen to increase after each dose all groups receiving mRNA vaccines. The GMTs obtained with mRNA vaccines at week 10 (2 weeks post-dose 3) were 1 to 2 orders of magnitude higher than in the animals that received RSV A2 depending on the dose and mRNA being tested. Serum samples from mVRC-1 (v2) immunized animals exhibited the highest neutralization titers, demonstrating a five-fold higher potency relative to MRK-04_nopolyA_3 mut.

B. Competition ELISA

Competition ELISA titers were determined for palivizumab, D25 and 4D7 to characterize the antigenic site ø, antigenic site I and antigenic site II response to the various mRNA-based vaccines as described above.

Figure 15:
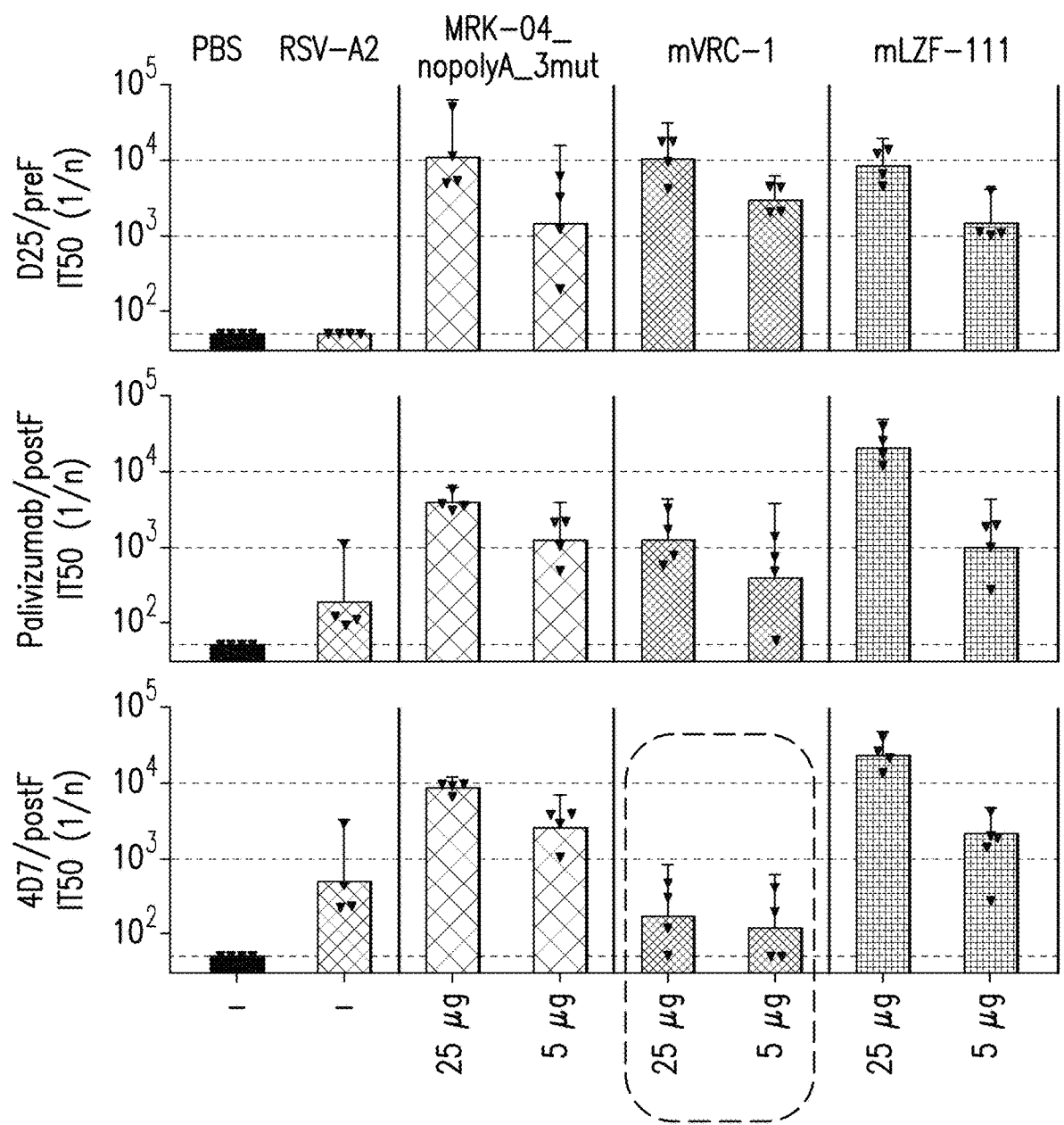
FIG. 15 sets forth serum antibody competition ELISA titers ($IT_{50}$ Individual and GMT with 95% Confidence intervals) against D25 (site ø), palivizumab (site II), and 4D7 (site I) measured at week 10 (2 weeks PD3).

The palivizumab, D25 and 4D7 competing antibody titers measured at week 10 (2 weeks PD3) are presented in FIG. 15. The competition data revealed that mVRC-1 (v2) induced lower levels of 4D7-postfusion F competing antibodies, while D25-prefusion titers and palivizumab titers are not affected. This different competition profile correlates with mVRC-1 (v2) mRNA expressing a more prefusion stabilized protein then MRK-04_nopolyA_3 mut and mLZF-111.

C. African Green Monkey Challenge Results

As mentioned above, in order to evaluate vaccine efficacy African Green Monkeys were challenged intranasally with $1 \times 10^{5.5}$ PFU RSV A2 on day 70 post vaccination and nasopharyngeal swabs and lung lavage samples were collected post challenge to test for the presence of virus.

Figure 16A:
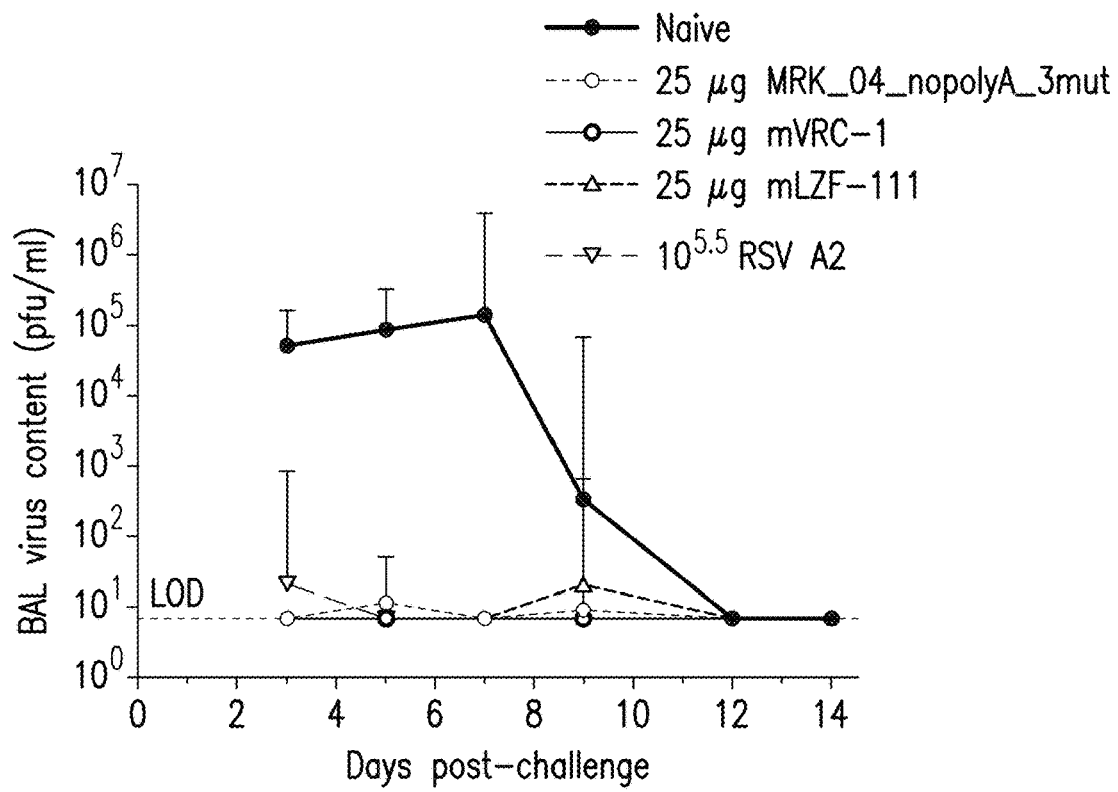
FIGS. 16A-16C sets forth RSV content in bronchoalveolar (BAL) fluid after challenge of AGMs.
Figure 16B:
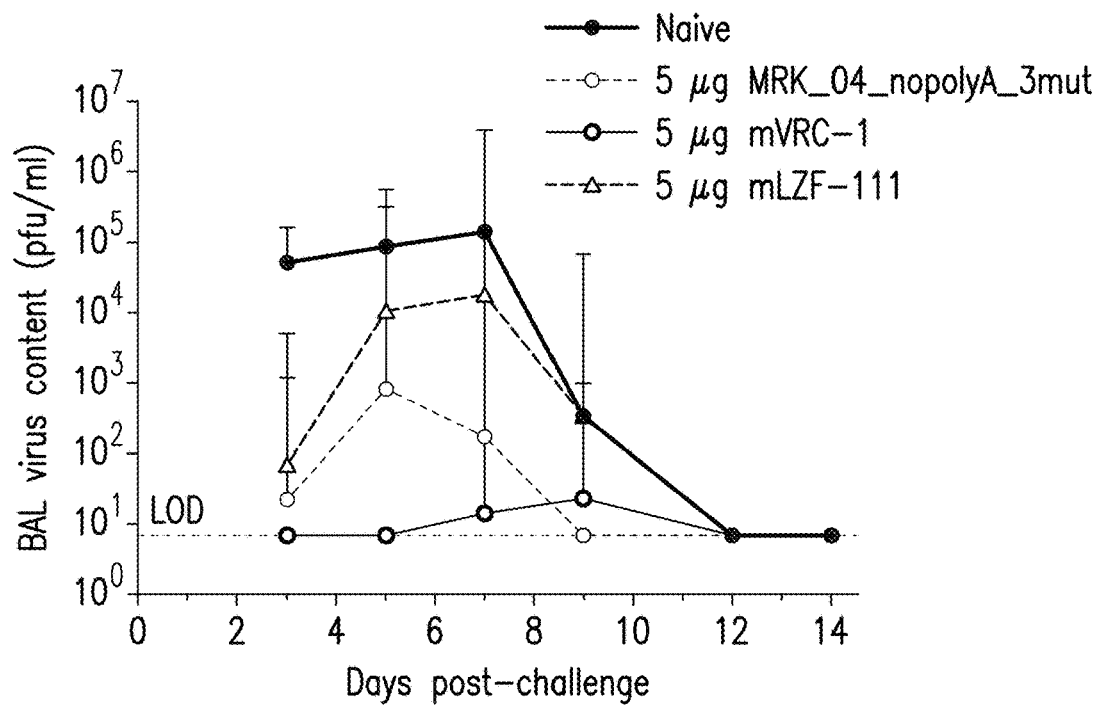
Figure 16C:
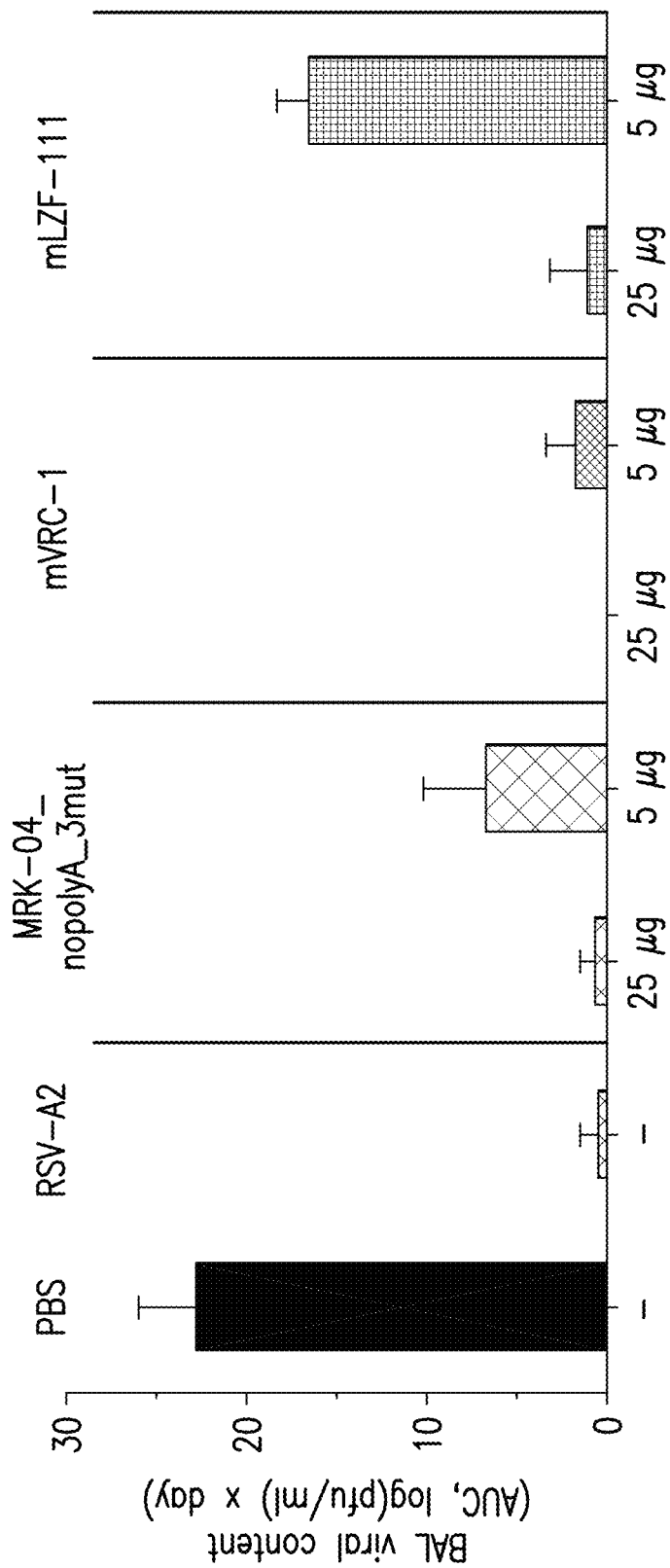

In order to measure RSV titers in the African Green Monkey lung lavage samples a viral plaque assay procedure for measuring viral titers was followed as outlined below. Briefly, samples were diluted and added in duplicate to 24-well plates containing confluent HEp-2 cell monolayers. The plates were incubated at 37° C. for one hour. Following the one-hour incubation, sample inoculum was aspirated and 1 ml of overlay containing 0.75% methylcellulose was added. The plates were incubated at 37° C. for 5 days. Following the 5-day incubation, the cells were fixed and stained with crystal violet/glutaraldehyde solution. Plaques were counted and titers were expressed as pfu/ml. Analysis of viral content in bronchoalveolar lavage (BAL) fluid (FIGS. 16A-16C) revealed that only mVRC-1 (v2) (25 μg) conferred total protection in the lung, and it afforded the best protection at a lower dose (5 μg).

In order to measure RSV titers in the African Green Monkey nasopharyngeal swabs an RSV RT-qPCR assay to detect RSV A was carried out as follows:

1) Equipment and Materials:
  A. Equipment
    1. Stratagene Mx3005P Real Time PCR system and MxPro Software
    2. Jouan GR422 centrifuge or equivalent
    3. Jouan Plate carriers or equivalent
  B. Reagents
    1. Quantitect® Probe Rt-PCR kit (1000) catalog #204445
    2. Water, Molecular Biology Grade DNAase-free and Protease free, 5 Prime, catalog #2900136
    3. TE buffer, 10 mM Tris 1 mM EDTA pH 8.0, Fisher Bioreagents, catalog #BP2473-100
    4. Viral primers: RSV A Forward and Reverse primers, Sigma custom, HPLC purified. Primer stocks are reconstituted to 100 uM in Molecular grade water and stored at −20° C.
    5. RSV dual labeled probe, Sigma custom, HPLC purified. Probe stocks are reconstituted to 100 uM in TE buffer and stored at −20° C. protected from light.
    6. RSV A standard were generated in-house and stored at −20° C. Standards for the assay were generated by designing primer pairs to the N gene of RSV A. The product length for the RSV A standard is 885 bp. QIAGEN OneStep RT-PCR was used to generate this standard.

| Primers | Sequences |
|---|---|
| RSV A F N gene | 5' CTC AAT TTC CTC ACT TCT CCA GTG T (SEQ ID NO: 46) |
| RSV A R N gene | 5' CTT GAT TCC TCG GTG TAC CTC TGT (SEQ ID NO: 47) |
| RSV A FAM N gene | 5'FAM-TCC CAT TAT GCC TAG GCC AGC AGC A (BHQI) (SEQ ID NO: 48) |

7. Promega, Maxwell® 16 Viral Total Nucleic Acid Purification Kit (Product #AS1150
  C. Supplies
    1. Stratagene Optical cap 8× strip, catalog #401425
    2. Stratagene Mx3000P 96 well plates, skirted, catalog #401334
    3. ART filtered pipet tips
2) RT-PCR Reactions and Set Up
  A. Preparation of Complete Master Mix
    1. Prepare complete Master Mix following the set up below for a final reaction volume of 50 μL. The following table is volume per well. Final primer concentration is 300 nM and final probe concentration is 200 nM.

| Reagent | μL |
|---|---|
| 2× Master Mix | 25 |
| RSV A F 100 uM | 0.2 |
| RSV A R 100 uM | 0.2 |
| RSV A FAM 100 uM | 0.1 |
| RT enzyme mix | 0.5 |
| Water | 19 |

2. Add 45 μL of complete master mix to each well. Cover plate with plate cover and wrap in aluminum foil to protect from light.
  B. Preparation of Standard curve
    1. Remove standard from −20° C.
    2. Dilute standards to final concentrations of 1e6 copy/5 μL to 1 copy/5 μL using 10-fold dilutions.
  C. Sample preparation
    1. Nasopharyngeal swab and lung lavage samples are prepared for the RT-PCR reaction using the Maxwell® 16 Viral Total Nucleic Acid Purification Kit (Promega, product #AS1150)
    2. 200 μL of sample is extracted following the manufactures protocol and eluted into 50 μL to be used in PCR reactions.
  D. Additions of samples
    1. Add 5 μL of extracted samples to appropriate wells. After addition of samples, carefully cap sample wells before adding standard curves.
    2. Add 5 μL of diluted standard to appropriate wells and cap.
    3. Add 5 μL of molecular grade water to No Template Control (NTC) wells.
    4. Wrap plates in aluminum foil and transfer plates to centrifuge.

5. Spin plates for 2 mins at 100 rpm to pull down any samples or master mix that may be on the sides of well.
6. Wrap plates in aluminum foil and transfer to Stratagene instrument.

E. Thermo cycler: Stratagene MX 3005P

1. Place plates in Stratagene Mx3005P and set thermal profile conditions to:

| Step | Time | Temperature |
|---|---|---|
| Reverse Transcription | 30 min | 50 |
| PCR initial activation step | 15 min | 95 |
| 2-step cycling: | | |
| Denaturation | 16 sec | 94 |
| Combined annealing/extension | 60 sec | 62 |
| Number of cycles | 40 | |

2. Analyze results using the Stratagene Mx3005p software

Figure 17A:
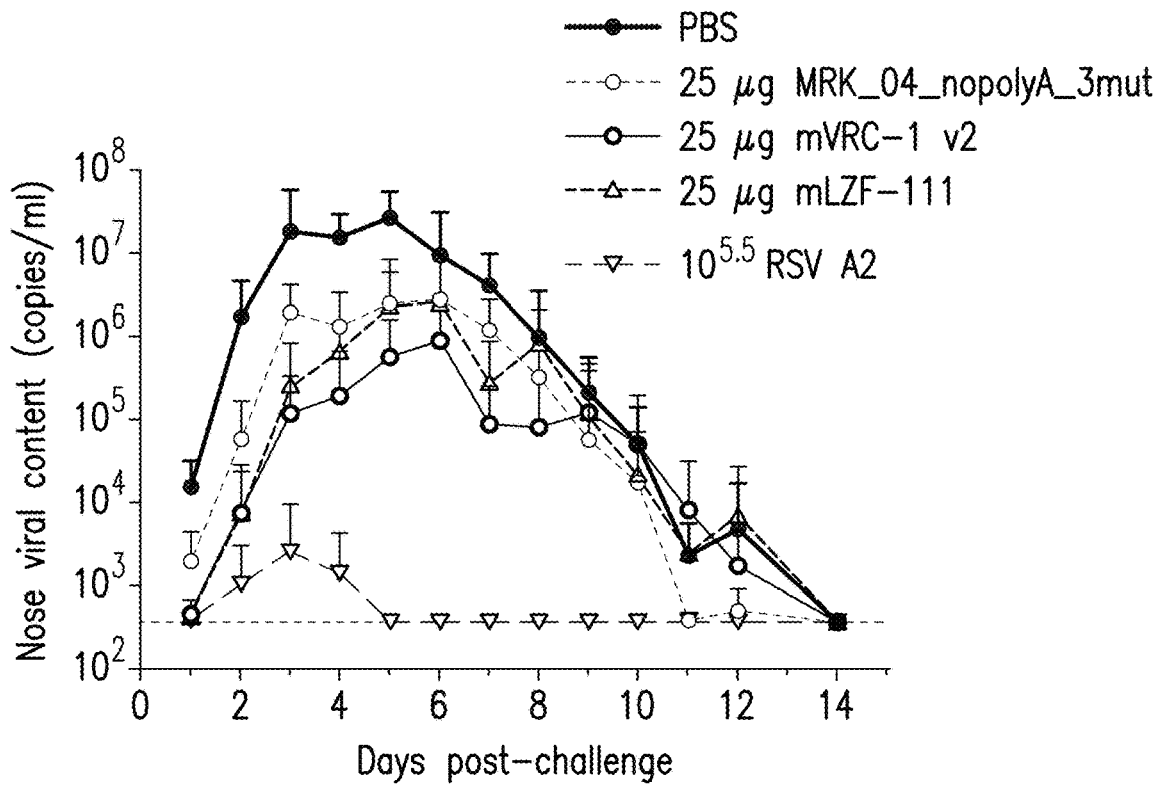
FIGS. 17A-17C sets forth the RSV content in nose swabs after challenge of AGMs.
Figure 17B:
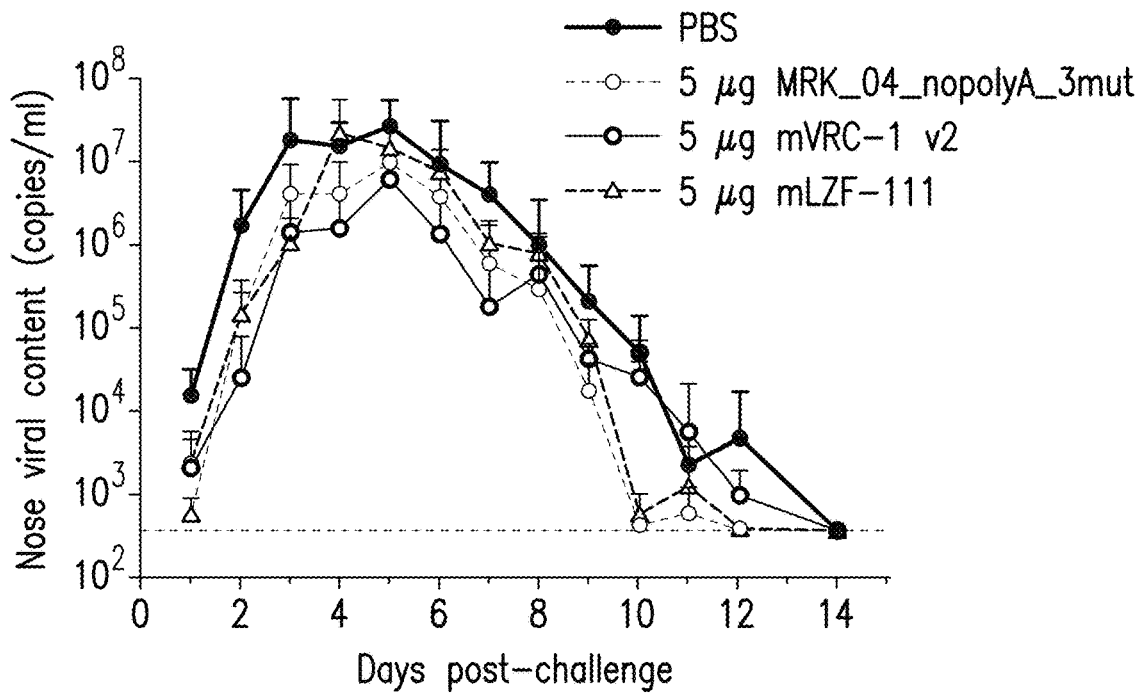
Figure 17C:
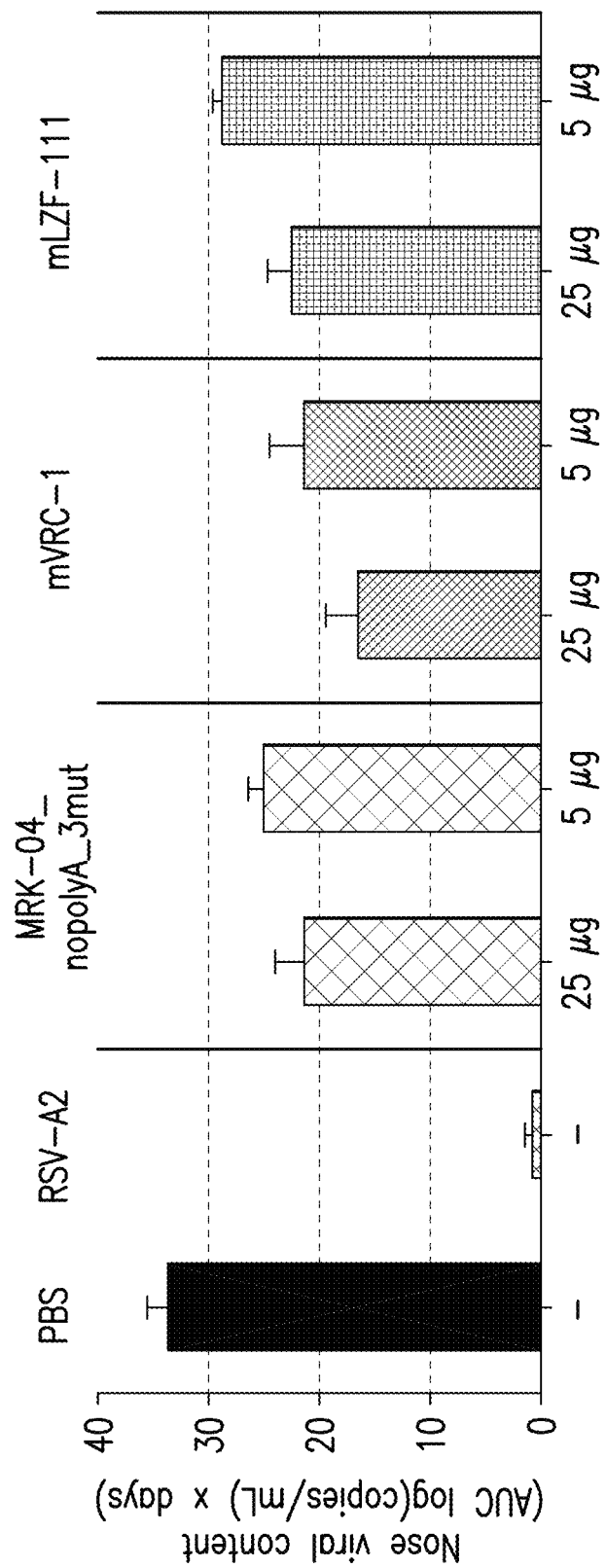

The mean RNA copy number detected in the nose samples are presented in FIGS. 17A-17C. The protective effect of all mRNA-based vaccines was less apparent in the nose, but again mVRC-1 (v2) demonstrated a 5-fold higher efficacy over MRK-04_nopolyA_3 mut.

Example 6: Immunogenicity in RSV-Experienced African Green Monkeys

The immunogenicity of mRNA vaccines formulated in LNP was tested in RSV-experienced African Green Monkeys.

Healthy adult, African Green Monkeys of either sex (n=4 or 5/group), with body weights ranging from 2.85 to 4.65 kg, that were confirmed to be RSV seropositive by ELISA and neutralizing antibody titers, were selected for the study. The pool of animals selected for this study had been experimentally infected with RSV in previous studies and were distributed across study groups based on their pre study RSV neutralization titers so that all groups would have similar group GMTs at study start. RSV experienced animals provide a model of immune memory recall response to vaccination that may reflect the responses that can be anticipated in seropositive human adults, with the caveat that the antibody response in AGMs following RSV exposure is more biased towards postfusion F protein epitopes than the human immune repertoire.

A single vaccine dose was administered to each animal at week 0 by the intramuscular (IM) route. A control group receiving only PBS was also included in the study design. Vaccines were administered as described in Table 2. After vaccination, the animals were observed daily for any changes at the inoculation site or other changes in activity or feeding habits that might indicate an adverse reaction to the vaccine but none were noted. Serum samples were collected for assessment of RSV neutralizing antibody titers, as well as palivizumab (site II), D25 (site ø) and 4D7 (site I) competing antibody titers.

TABLE 2

Vaccine Formulations Tested for Immunogenicity in RSV Seropositive African Green Monkeys

| Group | Vaccine | Conc (µg/ml) | Dose (µg) |
|---|---|---|---|
| 1 | MRK-04_nopolyA_3mut, I.M. | 10 | 5 |
| 2 | mVRC-1 (v2), I.M. | 10 | 5 |
| 3 | mVRC-1 (v2), I.M | 2 | 1 |
| 4 | mLZF-111 | 10 | 5 |
| 5 | mLZF-111 | 2 | 1 |
| 6 | None (PBS) | NA | NA |

Figure 18:
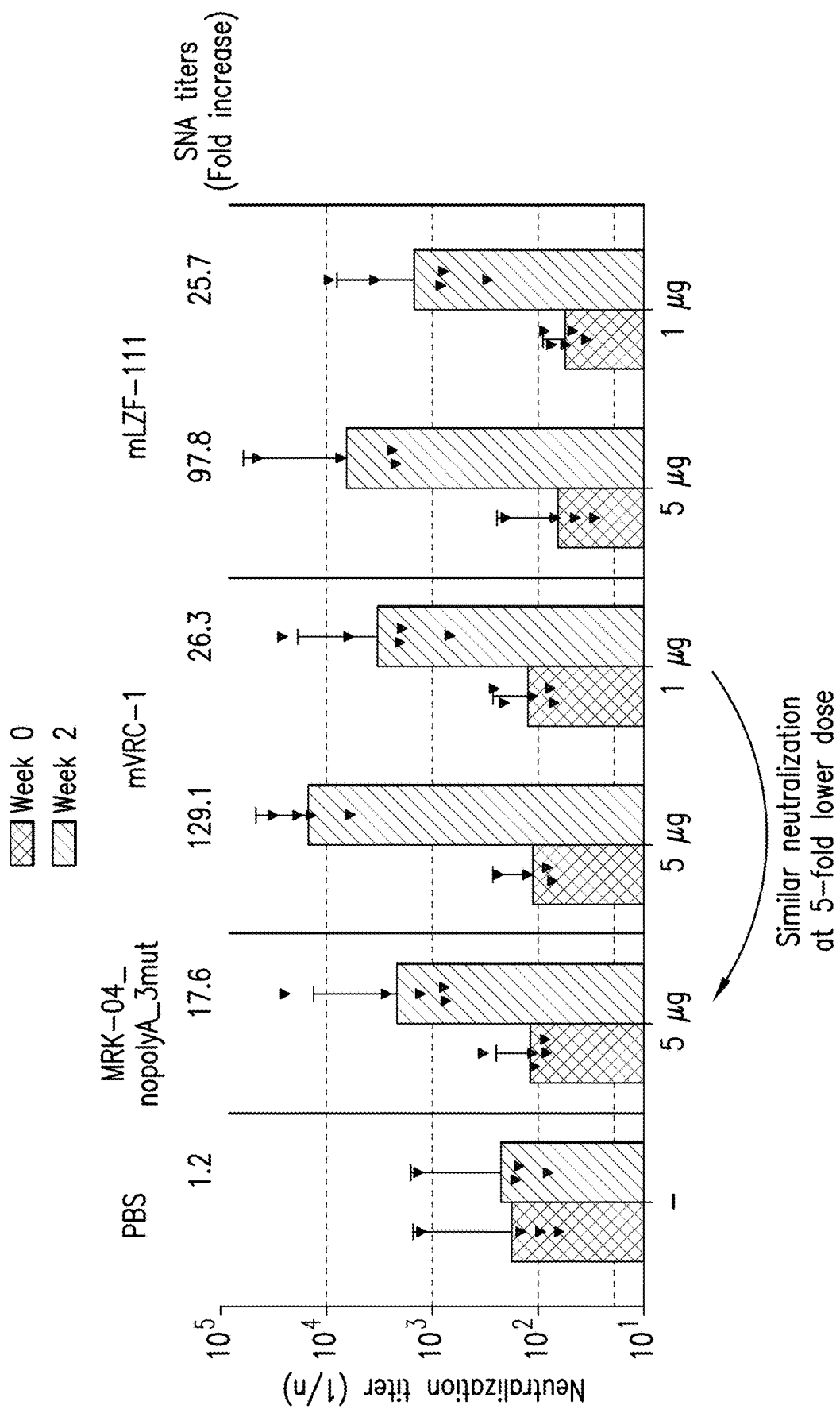
FIG. 18 sets forth serum neutralizing antibody titers ($NT_{50}$ Individual and GMT with 95% Confidence Intervals) to RSV A Experienced African Green Monkeys by mRNA vaccines and control formulations.

Individual animal $NT_{50}$ titers were measured in serum samples collected at baseline and 2 weeks post vaccination using methods described above and the results are shown in FIG. 18. All vaccines were found to be highly immunogenic as demonstrated by the increase in levels of serum antibodies binding RSV F proteins (both prefusion and postfusion RSV F, data not shown) and increases in serum neutralizing antibody levels. mVRC-1 (v2) induced the highest boost in neutralizing titers (>100 fold at the highest dose), and exhibited similar potency at a 5-fold lower dose relative to MRK-04_nopolyA_3 mut. Similarly, mLZF-111 also demonstrated increased potency relative to MRK-04_nopolyA_3 mut. No increase in titers was observed in the PBS control group.

Figure 19:
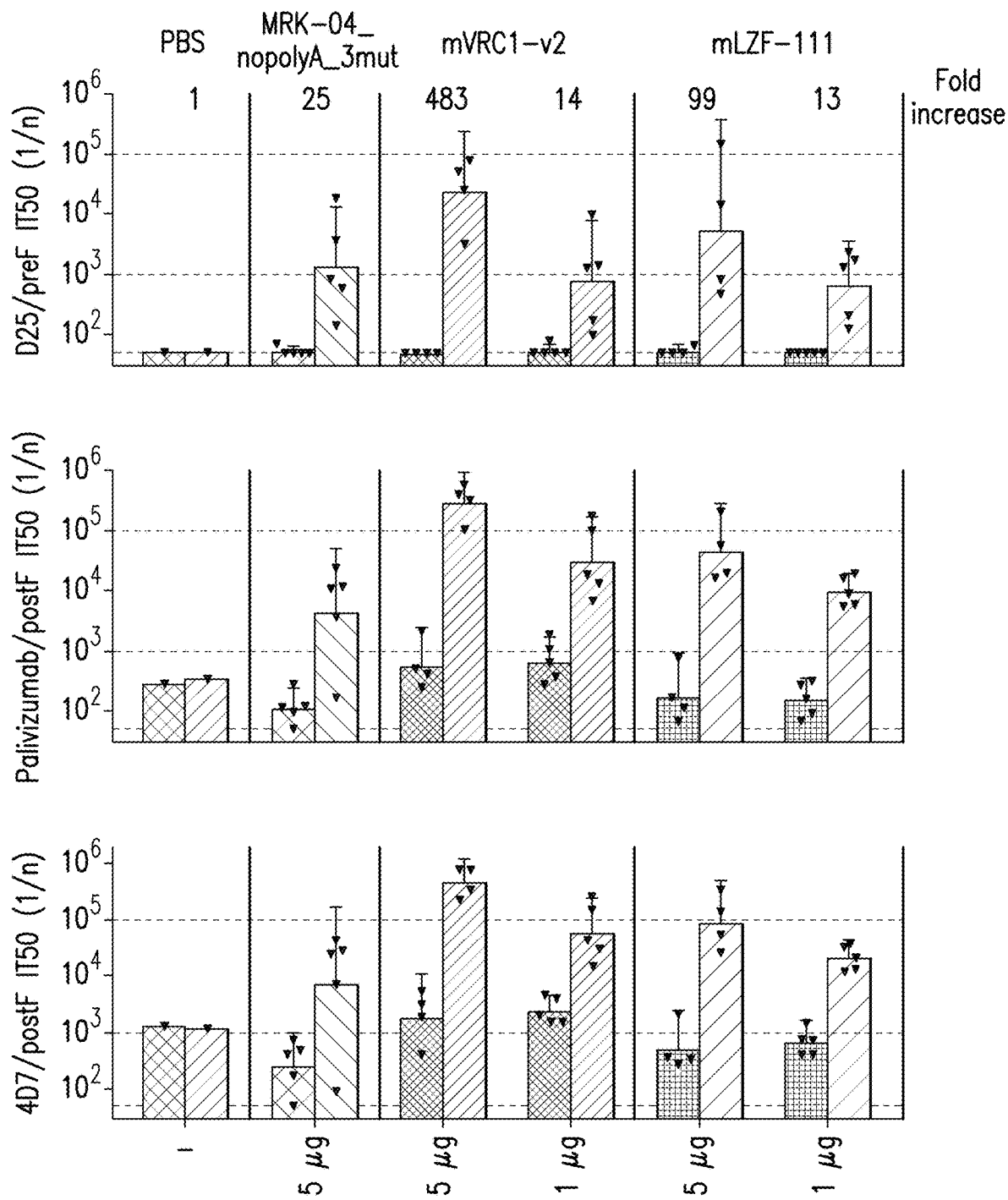
FIG. 19 sets forth serum antibody competition ELISA titers ($IT_{50}$ Individual and GMT with 95% Confidence intervals) against D25 (site ø), palivizumab (site II), and 4D7 (site I) measured at week 10 (2 weeks PD3).

To evaluate the quality of the boosted responses in the vaccinated animals, palivizumab (site II), D25 (site ø) and 4D7 (site I) competing antibody titers were determined in serum collected at 2 weeks post vaccination (FIG. 19). As described above, antigenic site II is a neutralization epitope found on both the prefusion and the postfusion conformation of the F protein, site ø is a prefusion specific neutralization epitope and 4D7 is a postfusion specific epitope. Due to the baseline immune bias to the postfusion conformation, RSV-experienced AGMs do not have detectable D25-competing antibody titers prior to immunization. However, all three mRNA antigens induced high D25 competing antibodies titers, demonstrating that AGMs do mount an antigenic site ø immune response after RSV infection that can be boosted by immunization. The boost in D25 competing antibody titers following mVRC-1 (v2) immunization were the highest (>450 fold), and demonstrating again similar potency at a 5-fold lower dose than the MRK-04_nopolyA_3 mut. In contrast to naïve animals (cotton rats and AGMs) we observed a high boost of 4D7/post-F specific antibodies in RSV-experienced AGMs in the mVRC-1 (v2) group, demonstrating that the baseline antibody pool can determine the outcome of the epitope-specific antibody profile after immunization. Since the B cell memory pool from natural RSV infection in humans is thought to be strongly biased towards the prefusion conformation, we speculate mVRC-1 (v2) immunization in humans will boost preferentially antibodies against these epitopes, known to have more potent neutralizing activity, leading to increased efficacy over MRK-04_nopolyA_3 mut.

TABLE 3

Sequence of amino acid linkers, TEV cleavage site, Thrombin Cleavage Site and Strep Tag

| Name | Sequence | SEQ ID NO: |
|---|---|---|
| 8 amino acid linker | GGGSGGGS | 1 |
| 10 amino acid linker | GGGSGGGSGG | 2 |
| 12 amino acid linker | GGGSGGGSGGGS | 3 |

TABLE 3-continued

Sequence of amino acid linkers, TEV cleavage site, Thrombin Cleavage Site and Strep Tag

| Name | Sequence | SEQ ID NO: |
|---|---|---|
| 14 amino acid linker | GGGSGGGSGGGSGS | 4 |
| Amino acid linker | GGGS | 49 |
| TEV Cleavage Site | ENLYFQS | 5 |
| Strep Tag | WSHPQFEK | 6 |
| Thrombin Cleavage Site | LVPRGS | 7 |
| Foldon | SAIGGYIPEAPRDGQAYVRKDGEWVLLSTFL | 8 |
| Signal Sequence | MELLILKANAITTILTAVTFCFASG | 9 |

TABLE 4

Antigenic Polypeptide Sequences

| Name | Sequence | SEQ ID NO: |
|---|---|---|
| RSV F protein reference sequence | MELLILKANAITTILTAVTFCFASGQNITEEFYQSTCSAVSKGYLSALRTGWYTSVITIELSNIKENKCNGTDAKVKLIKQELDKYKNAVTELQLLMQSTPPTNNRARRELPRFMNYTLNNAKKTNVTLSKKRKRRFLGFLLGVGSAIASGVAVSKVLHLEGEVNKIKSALLSTNKAVVSLSNGVSVLTSKVLDLKNYIDKQLLPIVNKQSCSISNIETVIEFQQKNNRLLEITREFSVNAGVTTPVSTYMLTNSELLSLINDMPITNDQKKLMSNNVQIVRQQSYSIMSIIKEEVLAYVVQLPLYGVIDTPCWKLHTSPLCTTNTKEGSNICLTRTDRGWYCDNAGSVSFFPQAETCKVQSNRVFCDTMNSLTLPSEINLCNVDIFNPKYDCKIMTSKTDVSSSVITSLGAIVSCYGKTKCTASNKNRGIIKTFSNGCDYVSNKGMDTVSVGNTLYYVNKQEGKSLYVKGEPIINFYDPLVFPSDEFDASISQVNEKINQSLAFIRKSDELLHNVAGKSTTNIMITTIIVIIVILLSLIAVGLLLYCKARSTPVTLSKDQLSGINNIAFSN | 10 |
| RSV F WT Reference Sequence with a foldon domain (bold) replacing amino acids 514-574 of RSV F WT | MELLILKANAITTILTAVTFCFASGQNITEEFYQSTCSAVSKGYLSALRTGWYTSVITIELSNIKENKCNGTDAKVKLIKQELDKYKNAVTELQLLMQSTPATNNRARRELPRFMNYTLNNAKKTNVTLSKKRKRRFLGFLLGVGSAIASGVAVSKVLHLEGEVNKIKSALLSTNKAVVSLSNGVSVLTSKVLDLKNYIDKQLLPIVNKQSCSISNIETVIEFQQKNNRLLEITREFSVNAGVTTPVSTYMLTNSELLSLINDMPITNDQKKLMSNNVQIVRQQSYSIMSIIKEEVLAYVVQLPLYGVIDTPCWKLHTSPLCTTNTKEGSNICLTRTDRGWYCDNAGSVSFFPQAETCKVQSNRVFCDTMNSLTLPSEVNLCNVDIFNPKYDCKIMTSKTDVSSSVITSLGAIVSCYGKTKCTASNKNRGIIKTFSNGCDYVSNKGVDTVSVGNTLYYVNKQEGKSLYVKGEPIINFYDPLVFPSDEFDASISQVNEKINQSLAFIRKSDELLHNVAGKSTTNIMITTGYIPEAPRDGQAYVRKDGEWVLLSTFL | 11 |
| RSV F WT ectodomain sequence (The sequence contains Foldon in bold, followed by a TEV cleavage site, a strep tag, a linker (underlined), a strep tag, another linker (underlined) and a His tag (italicized)) | MELLILKANAITTILTAVTFCFASGQNITEEFYQSTCSAVSKGYLSALRTGWYTSVITIELSNIKENKCNGTDAKVKLIKQELDKYKNAVTELQLLMQSTPATNNRARRELPRFMNYTLNNAKKTNVTLSKKRKRRFLGFLLGVGSAIASGVAVSKVLHLEGEVNKIKSALLSTNKAVVSLSNGVSVLTSKVLDLKNYIDKQLLPIVNKQSCSISNIETVIEFQQKNNRLLEITREFSVNAGVTTPVSTYMLTNSELLSLINDMPITNDQKKLMSNNVQIVRQQSYSIMSIIKEEVLAYVVQLPLYGVIDTPCWKLHTSPLCTTNTKEGSNICLTRTDRGWYCDNAGSVSFFPQAETCKVQSNRVFCDTMNSLTLPSEVNLCNVDIFNPKYDCKIMTSKTDVSSSVITSLGAIVS | 12 |

TABLE 4-continued

Antigenic Polypeptide Sequences

| Name | Sequence | SEQ ID NO: |
|---|---|---|
| | CYGKTKCTASNKNRGIIKTFSNGCDYVSN KGVDTVSVGNTLYYVNKQEGKSLYVKGE PIINFYDPLVFPSDEFDASISQVNEKINQSL AFIRKSDELLHNVNAGKSTTNIMITTGYIP EAPRDGQAYVRKDGEWVLLSTFLENLY FQSWSHPQFEKGGGSGGGSGGGSWSHPQ FEKGSGSGS*HHHHHHHH* | |
| DS-Cav1 peptide sequence (foldon sequence in bold) | MELLILKANAITTILTAVTFCFASGQNITEE FYQSTCSAVSKGYLSALRTGWYTSVITIEL SNIKENKCNGTDAKVKLIKQELDKYKNA VTELQLLMQSTPATNNRARRELPRFMNYT LNNAKKTNVTLSKKRKRRFLGFLLGVGSA IASGVAVCKVLHLEGEVNKIKSALLSTNK AVVSLSNGVSVLTFKVLDLKNYIDKQLLPI LNKQSCSISNIETVIEFQQKNNRLLEITREF SVNAGVTTPVSTYMLTNSELLSLINDMPIT NDQKKLMSNNVQIVRQQSYSIMCIIKEEV LAYVVQLPLYGVIDTPCWKLHTSPLCTTN TKEGSNICLTRTDRGWYCDNAGSVSFFPQ AETCKVQSNRVFCDTMNSLTLPSEVNLCN VDIFNPKYDCKIMTSKTDVSSSVITSLGAIV SCYGKTKCTASNKNRGIIKTFSNGCDYVS NKGVDTVSVGNTLYYVNKQEGKSLYVKG EPIINFYDPLVFPSDEFDASISQVNEKINQSL AFIRKSDELLSAIGGYIPEAPRDGQAYVR KDGEWVLLSTFL | 13 |
| LZF 40: Sequence contains an 8 amino acid linker (bold and underlined), DS-Cav1 substitutions (S155C, S290C, S190F and V207L) and a c-terminal foldon (bold). | MELLILKANAITTILTAVTFCFASGQNITEE FYQSTCSAVSKGYLSALRTGWYTSVITIEL SNIKENKCNGTDAKVKLIKQELDKYKNA VTELQLLM<u>GGGSGGGS</u>AIASGVAVCKVL HLEGEVNKIKSALLSTNKAVVSLSNGVSV LTFKVLDLKNYIDKQLLPILNKQSCSISNIE TVIEFQQKNNRLLEITREFSVNAGVTTPVS TYMLTNSELLSLINDMPITNDQKKLMSNN VQIVRQQSYSIMCIIKEEVLAYVVQLPLYG VIDTPCWKLHTSPLCTTNTKEGSNICLTRT DRGWYCDNAGSVSFFPQAETCKVQSNRV FCDTMNSLTLPSEVNLCNVDIFNPKYDCKI MTSKTDVSSSVITSLGAIVSCYGKTKCTAS NKNRGIIKTFSNGCDYVSNKGVDTVSVGN TLYYVNKQEGKSLYVKGEPIINFYDPLVFP SDEFDASISQVNEKINQSLAFIRKSDELLSA IGGYIPEAPRDGQAYVRKDGEWVLLST FL | 14 |
| LZF 40(a): Sequence contains an 8 amino acid linker (bold and underlined), DS-Cav1 substitutions (S155C, S290C, S190F and V207L), a c-terminal foldon (bold), a GG linker (underlined), a thrombin cleavage site, a His tag, a SA linker (underlined) and a strep tag. | MELLILKANAITTILTAVTFCFASGQNITEE FYQSTCSAVSKGYLSALRTGWYTSVITIEL SNIKENKCNGTDAKVKLIKQELDKYKNA VTELQLLM<u>GGGSGGGS</u>AIASGVAVCKVL HLEGEVNKIKSALLSTNKAVVSLSNGVSV LTFKVLDLKNYIDKQLLPILNKQSCSISNIE TVIEFQQKNNRLLEITREFSVNAGVTTPVS TYMLTNSELLSLINDMPITNDQKKLMSNN VQIVRQQSYSIMCIIKEEVLAYVVQLPLYG VIDTPCWKLHTSPLCTTNTKEGSNICLTRT DRGWYCDNAGSVSFFPQAETCKVQSNRV FCDTMNSLTLPSEVNLCNVDIFNPKYDCKI MTSKTDVSSSVITSLGAIVSCYGKTKCTAS NKNRGIIKTFSNGCDYVSNKGVDTVSVGN TLYYVNKQEGKSLYVKGEPIINFYDPLVFP SDEFDASISQVNEKINQSLAFIRKSDELLSA IGGYIPEAPRDGQAYVRKDGEWVLLST FL<u>GG</u>LVPRGSHHHHHH<u>SA</u>WSHPQFEK | 15 |
| LZF 55: Sequence contains a 10 amino acid linker (bold and underlined), DS-Cav1 substitutions (S155C, S290C, S190F and V207L) and a c-terminal foldon (bold). | MELLILKANAITTILTAVTFCFASGQNITEE FYQSTCSAVSKGYLSALRTGWYTSVITIEL SNIKENKCNGTDAKVKLIKQELDKYKNA VTELQLLM<u>GGGSGGGSGG</u>AIASGVAVCK VLHLEGEVNKIKSALLSTNKAVVSLSNGV SVLTFKVLDLKNYIDKQLLPILNKQSCSIS NIETVIEFQQKNNRLLEITREFSVNAGVTTP VSTYMLTNSELLSLINDMPITNDQKKLMS NNVQIVRQQSYSIMCIIKEEVLAYVVQLPL | 16 |

TABLE 4-continued

Antigenic Polypeptide Sequences

| Name | Sequence | SEQ ID NO: |
|---|---|---|
| | YGVIDTPCWKLHTSPLCTTNTKEGSNICLT RTDRGWYCDNAGSVSFFPQAETCKVQSN RVFCDTMNSLTLPSEVNLCNVDIFNPKYD CKIMTSKTDVSSSVITSLGAIVSCYGKTKC TASNKNRGIIKTFSNGCDYVSNKGVDTVS VGNTLYYVNKQEGKSLYVKGEPIINFYDP LVFPSDEFDASISQVNEKINQSLAFIRKSDE LLSAIGGYIPEAPRDGQAYVRKDGEWV LLSTFL | |
| LZF 55a: Sequence contains a 10 amino acid linker (bold and underlined), DS-Cav1 substitutions (S155C, S290C, S190F and V207L), a c-terminal foldon (bold), a GG linker (underlined), a thrombin cleavage site, a His tag, a SA linker (underlined) and a strep tag. | MELLILKANAITTILTAVTFCFASGQNITEE FYQSTCSAVSKGYLSALRTGWYTSVITIEL SNIKENKCNGTDAKVKLIKQELDKYKNA VTELQLLMGGGSGGGSGGAIASGVAVCK VLHLEGEVNKIKSALLSTNKAVVSLSNGV SVLTFKVLDLKNYIDKQLLPILNKQSCSIS NIETVIEFQQKNNRLLEITREFSVNAGVTTP VSTYMLTNSELLSLINDMPITNDQKKLMS NNVQIVRQQSYSIMCIIKEEVLAYVVQLPL YGVIDTPCWKLHTSPLCTTNTKEGSNICLT RTDRGWYCDNAGSVSFFPQAETCKVQSN RVFCDTMNSLTLPSEVNLCNVDIFNPKYD CKIMTSKTDVSSSVITSLGAIVSCYGKTKC TASNKNRGIIKTFSNGCDYVSNKGVDTVS VGNTLYYVNKQEGKSLYVKGEPIINFYDP LVFPSDEFDASISQVNEKINQSLAFIRKSDE LL SAIGGYIPEAPRDGQAYVRKDGEWV LLSTFLGGLVPRGSHHHHHSAWSHPQF EK | 17 |
| LZF 56: Sequence contains a 12 amino acid linker (bold and underlined), DS-Cav1 substitutions (S155C, S290C, S190F and V207L), and a c-terminal foldon (bold). | MELLILKANAITTILTAVTFCFASGQNITEE FYQSTCSAVSKGYLSALRTGWYTSVITIEL SNIKENKCNGTDAKVKLIKQELDKYKNA VTELQLLMGGGSGGGSGGGSAIASGVAV CKVLHLEGEVNKIKSALLSTNKAVVSLSN GVSVLTFKVLDLKNYIDKQLLPILNKQSCS ISNIETVIEFQQKNNRLLEITREFSVNAGVT TPVSTYMLTNSELLSLINDMPITNDQKKL MSNNVQIVRQQSYSIMCIIKEEVLAYVVQ LPLYGVIDTPCWKLHTSPLCTTNTKEGSNI CLTRTDRGWYCDNAGSVSFFPQAETCKV QSNRVFCDTMNSLTLPSEVNLCNVDIFNP KYDCKIMTSKTDVSSSVITSLGAIVSCYGK TKCTASNKNRGIIKTFSNGCDYVSNKGVD TVSVGNTLYYVNKQEGKSLYVKGEPIINF YDPLVFPSDEFDASISQVNEKINQSLAFIRK SDELLSAIGGYIPEAPRDGQAYVRKDGE WVLLSTFL | 18 |
| LZF 56a Sequence contains a 12 amino acid linker (bold and underlined), DS-Cav1 substitutions (S155C, S290C, S190F and V207L), a c-terminal foldon (bold), a GG linker (underlined), a thrombin cleavage site, a His tag, a SA linker (underlined) and a strep tag. | MELLILKANAITTILTAVTFCFASGQNITEE FYQSTCSAVSKGYLSALRTGWYTSVITIEL SNIKENKCNGTDAKVKLIKQELDKYKNAV TELQLLMGGGSGGGSGGGSGSAIASGVAV CKVLHLEGEVNKIKSALLSTNKAVVSLSN GVSVLTFKVLDLKNYIDKQLLPILNKQSCS ISNIETVIEFQQKNNRLLEITREFSVNAGV TTPVSTYMLTNSELLSLINDMPITNDQKKL MSNNVQIVRQQSYSIMCIIKEEVLAYVVQ LPLYGVIDTPCWKLHTSPLCTTNTKEGSNI CLTRTDRGWYCDNAGSVSFFPQAETCKV QSNRVFCDTMNSLTLPSEVNLCNVDIFNP KYDCKIMTSKTDVSSSVITSLGAIVSCYGK TKCTASNKNRGIIKTFSNGCDYVSNKGVD TVSVGNTLYYVNKQEGKSLYVKGEPIINF YDPLVFPSDEFDASISQVNEKINQSLAFIRK SDELLSAIGGYIPEAPRDGQAYVRKDGE WVLLSTFLGGLVPRGSHHHHHSAWSHP QFEK | 19 |
| LZF 57: Sequence contains a 14 amino acid linker (bold and underlined), DS-Cav1 substitutions (S155C, S290C, S190F | MELLILKANAITTILTAVTFCFASGQNITEE FYQSTCSAVSKGYLSALRTGWYTSVITIEL SNIKENKCNGTDAKVKLIKQELDKYKNA VTELQLLMGGGSGGGSGGGSGSSAIASGV AVCKVLHLEGEVNKIKSALLSTNKAVVSL SNGVSVLTFKVLDLKNYIDKQLLPILNKQS | 20 |

TABLE 4-continued

Antigenic Polypeptide Sequences

| Name | Sequence | SEQ ID NO: |
|---|---|---|
| and V207L), and a c-terminal foldon (bold). | CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPSDEFDASISQVNEKINQSLAFIR KSDELLSAIGGYIPEAPRDGQAYVRKDG EWVLLSTFL | |
| LZF 57a:<br>Sequence contains a 14 amino acid linker (bold and underlined), DS-Cav1 substitutions (S155C, S290C, S190F and V207L), a c-terminal foldon (bold), a GG linker (underlined), a thrombin cleavage site, a His tag, a SA linker (underlined) and a strep tag. | MELLILKANAITTILTAVTFCFASGQNITEE FYQSTCSAVSKGYLSALRTGWYTSVITIEL SNIKENKCNGTDAKVKLIKQELDKYKNA VTELQLLMGGGSGGGSGGGSGSAIASGV AVCKVLHLEGEVNKIKSALLSTNKAVVSL SNGVSVLTFKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPSDEFDASISQVNEKINQSLAFIR KSDELLSAIGGYIPEAPRDGQAYVRKDG EWVLLSTFLGGLVPRGSHHHHHHS<u>A</u>WSH PQFEK | 21 |
| LZF 109<br>Sequence contains a 14 amino acid linker (bold and underlined), DS-Cav1 substitutions (S155C, S290C, S190F and V207L), additional mutations S180C and S186C (bold, italicized and underlined) and a c-terminal foldon (bold) | MELLILKANAITTILTAVTFCFASGQNITEE FYQSTCSAVSKGYLSALRTGWYTSVITIEL SNIKENKCNGTDAKVKLIKQELDKYKNA VTELQLLMGGGSGGGSGGGSGSAIASGV AVCKVLHLEGEVNKIKSALLSTNKAVV*C*L SNGV*C*VLTFKVLDLKNYIDKQLLPILNKQ SCSISNIETVIEFQQKNNRLLEITREFSVNA GVTTPVSTYMLTNSELLSLINDMPITNDQK KLMSNNVQIVRQQSYSIMCIIKEEVLAYV VQLPLYGVIDTPCWKLHTSPLCTTNTKEG SNICLTRTDRGWYCDNAGSVSFFPQAETC KVQSNRVFCDTMNSLTLPSEVNLCNVDIF NPKYDCKIMTSKTDVSSSVITSLGAIVSCY GKTKCTASNKNRGIIKTFSNGCDYVSNKG VDTVSVGNTLYYVNKQEGKSLYVKGEPII NFYDPLVFPSDEFDASISQVNEKINQSLAFI RKSDELLSAIGGYIPEAPRDGQAYVRKD GEWVLLSTFL | 22 |
| LZF 109a<br>Sequence contains a 14 amino acid linker (bold and underlined), DS-Cav1 substitutions (S155C, S290C, S190F and V207L), additional mutations S180C and S186C (bold, italicized and underlined) and a c-terminal foldon (bold), a GG linker (underlined), a thrombin cleavage site, a His tag, a SA linker (underlined) and a strep tag. | MELLILKANAITTILTAVTFCFASGQNITEE FYQSTCSAVSKGYLSALRTGWYTSVITIEL SNIKENKCNGTDAKVKLIKQELDKYKNA VTELQLLMGGGSGGGSGGGSGSAIASGV AVCKVLHLEGEVNKIKSALLSTNKAVV*C*L SNGV*C*VLTFKVLDLKNYIDKQLLPILNKQ SCSISNIETVIEFQQKNNRLLEITREFSVNA GVTTPVSTYMLTNSELLSLINDMPITNDQK KLMSNNVQIVRQQSYSIMCIIKEEVLAYV VQLPLYGVIDTPCWKLHTSPLCTTNTKEG SNICLTRTDRGWYCDNAGSVSFFPQAETC KVQSNRVFCDTMNSLTLPSEVNLCNVDIF NPKYDCKIMTSKTDVSSSVITSLGAIVSCY GKTKCTASNKNRGIIKTFSNGCDYVSNKG VDTVSVGNTLYYVNKQEGKSLYVKGEPII NFYDPLVFPSDEFDASISQVNEKINQSLAFI RKSDELLSAIGGYIPEAPRDGQAYVRKD GEWVLLSTFLGGLVPRGSHHHHHHS<u>A</u>W SHPQFEK | 23 |

TABLE 4-continued

Antigenic Polypeptide Sequences

| Name | Sequence | SEQ ID NO: |
|---|---|---|
| LZF 110<br>Sequence contains a 14 amino acid linker (bold and underlined), DS-Cav1 substitutions (S155C, S290C, S190F and V207L), additional mutations D486C and A490C (bold, italicized and underlined) and a c-terminal foldon (bold) | MELLILKANAITTILTAVTFCFASGQNITEE FYQSTCSAVSKGYLSALRTGWYTSVITIEL SNIKENKCNGTDAKVKLIKQELDKYKNA VTELQLLMGGGSGGGSGGGSGSAIASGV AVCKVLHLEGEVNKIKSALLSTNKAVVSL SNGVSVLTFKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPS_C_EFD_C_SISQVNEKINQSLAFIR KSDELLSAIGGYIPEAPRDGQAYVRKDG EWVLLSTFL | 24 |
| LZF 110a<br>Sequence contains a 14 amino acid linker (bold and underlined), DS-Cav1 substitutions (S155C, S290C, S190F and V207L), additional mutations D486C and A490C (bold, italicized and underlined), a c-terminal foldon (bold), a GG linker (underlined), a thrombin cleavage site, a His tag, a SA linker (underlined) and a strep tag. | MELLILKANAITTILTAVTFCFASGQNITEE FYQSTCSAVSKGYLSALRTGWYTSVITIEL SNIKENKCNGTDAKVKLIKQELDKYKNA VTELQLLMGGGSGGGSGGGSGSAIASGV AVCKVLHLEGEVNKIKSALLSTNKAVVSL SNGVSVLTFKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPSCEFDCSISQVNEKINQSLAFIR KSDELLSAIGGYIPEAPRDGQAYVRKDG EWVLLSTFLGGLVPRGSHHHHHHSAWSH PQFEK | 25 |
| LZF 111<br>Sequence contains a 14 amino acid linker (bold and underlined), DS-Cav1 substitutions (S155C, S290C, S190F and V207L), additional mutations D486C and D489C (bold, italicized and underlined) and a c-terminal foldon (bold) | MELLILKANAITTILTAVTFCFASGQNITE FEYQSTCSAVSKGYLSALRTGWYTSVITIE LSNIKENKCNGTDAKVKLIKQELDKYKNA VTELQLLMGGGSGGGSGGGSGSAIASGV AVCKVLHLEGEVNKIKSALLSTNKAVVSL SNGVSVLTFKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPS_C_EF_C_ASISQVNEKINQSLAFIR KSDELLSAIGGYIPEAPRDGQAYVRKDG EWVLLSTFL | 26 |
| LZF 111a<br>Sequence contains a 14 amino acid linker (bold and underlined), DS-Cav1 substitutions (S155C, S290C, S190F and V207L), additional mutations D486C and D489C (bold, italicized and underlined), a c-terminal foldon (bold), a GG linker | MELLILKANAITTILTAVTFCFASGQNITEE FYQSTCSAVSKGYLSALRTGWYTSVITIEL SNIKENKCNGTDAKVKLIKQELDKYKNA VTELQLLMGGGSGGGSGGGSGSAIASGV AVCKVLHLEGEVNKIKSALLSTNKAVVSL SNGVSVLTFKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN | 27 |

TABLE 4-continued

Antigenic Polypeptide Sequences

| Name | Sequence | SEQ ID NO: |
|---|---|---|
| (underlined), a thrombin cleavage site, a His tag, a SA linker (underlined) and a strep tag. | PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPCECASISQVNEKINQSLAFIR KSDELLSAIGGYIPEAPRDGQAYVRKDG EWVLLSTFLGGLVPRGSHHHHHHSAWSH PQFEK | |
| LZF 112<br>Sequence contains a 14 amino acid linker (bold and underlined), DS-Cav1 substitutions (S155C, S290C, S190F and V207L), additional mutations L512C and L513C (bold, italicized and underlined) and a c-terminal foldon (bold) | MELLILKANAITTILTAVTFCFASGQNITEE FYQSTCSAVSKGYLSALRTGWYTSVITIEL SNIKENKCNGTDAKVKLIKQELDKYKNA VTELQLLMGGSGGGSGGGSGSAIASGV AVCKVLHLEGEVNKIKSALLSTNKAVVSL SNGVSVLTFKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPSDEFDASISQVNEKINQSLAFIR KSDECC SAIGGYIPEAPRDGQAYVRKDG EWVLLSTFL | 28 |
| LZF 112a<br>Sequence contains a 14 amino acid linker (bold and underlined), DS-Cav1 substitutions (S155C, S290C, S190F and V207L), additional mutations L512C and L513C (bold, italicized and underlined), a c-terminal foldon (bold), a GG linker (underlined), a thrombin cleavage site, a His tag, a SA linker (underlined) and a strep tag. | MELLILKANAITTILTAVTFCFASGQNITEE FYQSTCSAVSKGYLSALRTGWYTSVITIEL SNIKENKCNGTDAKVKLIKQELDKYKNA VTELQLLMGGSGGGSGGGSGSAIASGV AVCKVLHLEGEVNKIKSALLSTNKAVVSL SNGVSVLTFKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPSDEFDASISQVNEKINQSLAFIR KSDECC SAIGGYIPEAPRDGQAYVRKDG EWVLLSTFLGGLVPRGSHHHHHHSAWSH PQFEK | 29 |
| LZF 113<br>Sequence contains a 14 amino acid linker (bold and underlined), DS-Cav1 substitutions (S155C, S290C, S190F and V207L), additional mutation F505C (bold, italicized and underlined) and a c-terminal foldon (bold). | MELLILKANAITTILTAVTFCFASGQNITEE FYQSTCSAVSKGYLSALRTGWYTSVITIEL SNIKENKCNGTDAKVKLIKQELDKYKNA VTELQLLMGGSGGGSGGGSGSAIASGV AVCKVLHLEGEVNKIKSALLSTNKAVVSL SNGVSVLTFKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPSDEFDASISQVNEKINQSLACIR KSDELLSAIGGYIPEAPRDGQAYVRKDG EWVLLSTFL | 30 |
| LZF 113a<br>Sequence contains a 14 amino acid linker (bold and underlined), DS-Cav1 substitutions (S155C, S290C, S190F and V207L), additional mutation F505C (bold, italicized and | MELLILKANAITTILTAVTFCFASGQNITEE FYQSTCSAVSKGYLSALRTGWYTSVITIEL SNIKENKCNGTDAKVKLIKQELDKYKNA VTELQLLMGGSGGGSGGGSGSAIASGV AVCKVLHLEGEVNKIKSALLSTNKAVVSL SNGVSVLTFKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV | 31 |

TABLE 4-continued

Antigenic Polypeptide Sequences

| Name | Sequence | SEQ ID NO: |
|---|---|---|
| underlined), a c-terminal foldon (bold), a GG linker (underlined), a thrombin cleavage site, a His tag, a SA linker (underlined) and a strep tag. | QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPSDEFDASISQVNEKINQSL_C_IR KSDELLSAIGGYIPEAPRDGQAYVRKDG EWVLLSTFLGGLVPRGSHHHHHHSAWSH PQFEK | |
| LZF 123<br>Sequence contains DS-Cav1 substitutions (S155C, S290C, S190F and V207L) and additional substitutions S180C and S186C (bold, italicized and underlined) and a c-terminal foldon (bold). | MELLILKANAITTILTAVTFCFASGQNITEE FYQSTCSAVSKGYLSALRTGWYTSVITIEL SNIKENKCNGTDAKVKLIKQELDKYKNA VTELQLLMQSTPATNNRARRELPRFMNYT LNNAKKTNVTLSKKRKRRFLGFLLGVGSA IASGVAVCKVLHLEGEVNKIKSALLSTNK AV_C_LSNG_C_VLTFKVLDLKNYIDKQLLP ILNKQSCSISNIETVIEFQQKNNRLLEITREF SVNAGVTTPVSTYMLTNSELLSLINDMPIT NDQKKLMSNNVQIVRQQSYSIMCIIKEEV LAYVVQLPLYGVIDTPCWKLHTSPLCTTN TKEGSNICLTRTDRGWYCDNAGSVSFFPQ AETCKVQSNRVFCDTMNSLTLPSEVNLCN VDIFNPKYDCKIMTSKTDVSSSVITSLGAIV SCYGKTKCTASNKNRGIIKTFSNGCDYVS NKGVDTVSVGNTLYYVNKQEGKSLYVKG EPIINFYDPLVFPSDEFDASISQVNEKINQSL AFIRKSDELLSAIGGYIPEAPRDGQAYVR KDGEWVLLSTFL | 32 |
| LZF 123a<br>Sequence contains DS-Cav1 substitutions (S155C, S290C, S190F and V207L) and additional substitutions S180C and S186C (bold, italicized and underlined), a c-terminal foldon (bold), a GG linker (underlined), a thrombin cleavage site, a His tag, a SA linker (underlined) and a strep tag. | MELLILKANAITTILTAVTFCFASGQNITEE FYQSTCSAVSKGYLSALRTGWYTSVITIEL SNIKENKCNGTDAKVKLIKQELDKYKNA VTELQLLMQSTPATNNRARRELPRFMNYT LNNAKKTNVTLSKKRKRRFLGFLLGVGSA IASGVAVCKVLHLEGEVNKIKSALLSTNK AV_C_LSNG_C_VLTFKVLDLKNYIDKQLLP ILNKQSCSISNIETVIEFQQKNNRLLEITREF SVNAGVTTPVSTYMLTNSELLSLINDMPIT NDQKKLMSNNVQIVRQQSYSIMCIIKEEV LAYVVQLPLYGVIDTPCWKLHTSPLCTTN TKEGSNICLTRTDRGWYCDNAGSVSFFPQ AETCKVQSNRVFCDTMNSLTLPSEVNLCN VDIFNPKYDCKIMTSKTDVSSSVITSLGAIV SCYGKTKCTASNKNRGIIKTFSNGCDYVS NKGVDTVSVGNTLYYVNKQEGKSLYVKG EPIINFYDPLVFPSDEFDASISQVNEKINQSL AFIRKSDELLSAIGGYIPEAPRDGQAYVR KDGEWVLLSTFLGGLVPRGSHHHHHHS AWSHPQFEK | 33 |
| LZF124<br>Sequence contains DS-Cav1 substitutions (S155C, S290C, S190F and V207L) and additional substitutions D486C and A490C (bold, italicized and underlined) and a c-terminal foldon (bold). | MELLILKANAITTILTAVTFCFASGQNITEE FYQSTCSAVSKGYLSALRTGWYTSVITIEL SNIKENKCNGTDAKVKLIKQELDKYKNA VTELQLLMQSTPATNNRARRELPRFMNYT LNNAKKTNVTLSKKRKRRFLGFLLGVGSA IASGVAVCKVLHLEGEVNKIKSALLSTNK AVVSLSNGVSVLTFKVLDLKNYIDKQLLPI LNKQSCSISNIETVIEFQQKNNRLLEITREF SVNAGVTTPVSTYMLTNSELLSLINDMPIT NDQKKLMSNNVQIVRQQSYSIMCIIKEEV LAYVVQLPLYGVIDTPCWKLHTSPLCTTN TKEGSNICLTRTDRGWYCDNAGSVSFFPQ AETCKVQSNRVFCDTMNSLTLPSEVNLCN VDIFNPKYDCKIMTSKTDVSSSVITSLGAIV SCYGKTKCTASNKNRGIIKTFSNGCDYVS NKGVDTVSVGNTLYYVNKQEGKSLYVKG EPIINFYDPLVFP_C_EF_C_SISQVNEKINQSL AFIRKSDELLSAIGGYIPEAPRDGQAYVR KDGEWVLLSTFL | 34 |
| LZF 124 a<br>Sequence contains DS-Cav1 substitutions | MELLILKANAITTILTAVTFCFASGQNITEE FYQSTCSAVSKGYLSALRTGWYTSVITIEL SNIKENKCNGTDAKVKLIKQELDKYKNA | 35 |

TABLE 4-continued

Antigenic Polypeptide Sequences

| Name | Sequence | SEQ ID NO: |
|---|---|---|
| (S155C, S290C, S190F and V207L), additional substitutions D486C and A490C (bold, italicized and underlined) and a c-terminal foldon (bold), a GG linker (underlined), a thrombin cleavage site, a His tag, a SA linker (underlined) and a strep tag. | VTELQLLMQSTPATNNRARRELPRFMNYT LNNAKKTNVTLSKKRKRRFLGFLLGVGSA IASGVAVCKVLHLEGEVNKIKSALLSTNK AVVSLSNGVSVLTFKVLDLKNYIDKQLLPI LNKQSCSISNIETVIEFQQKNNRLLEITREF SVNAGVTTPVSTYMLTNSELLSLINDMPIT NDQKKLMSNNVQIVRQQSYSIMCIIKEEV LAYVVQLPLYGVIDTPCWKLHTSPLCTTN TKEGSNICLTRTDRGWYCDNAGSVSFFPQ AETCKVQSNRVFCDTMNSLTLPSEVNLCN VDIFNPKYDCKIMTSKTDVSSSVITSLGAIV SCYGKTKCTASNKNRGIIKTFSNGCDYVS NKGVDTVSVGNTLYYVNKQEGKSLYVKG EPIINFYDPLVFPS*C* EFI*C* SISQVNEKINQSL AFIRKSDELLSAIGGYIPEAPRDGQAYVR KDGEWVLLSTFLGGLVPRGSHHHHHHS AWSHPQFEK | |
| LZF 125 Sequence contains DS-Cav1 substitutions (S155C, S290C, S190F and V207L) and additional substitutions D486C and D489C (bold, italicized and underlined) and a c-terminal foldon (bold). | MELLILKANAITTILTAVTFCFASGQNITEE FYQSTCSAVSKGYLSALRTGWYTSVITIEL SNIKENKCNGTDAKVKLIKQELDKYKNA VTELQLLMQSTPATNNRARRELPRFMNYT LNNAKKTNVTLSKKRKRRFLGFLLGVGSA IASGVAVCKVLHLEGEVNKIKSALLSTNK AVVSLSNGVSVLTFKVLDLKNYIDKQLLPI LNKQSCSISNIETVIEFQQKNNRLLEITREF SVNAGVTTPVSTYMLTNSELLSLINDMPIT NDQKKLMSNNVQIVRQQSYSIMCIIKEEV LAYVVQLPLYGVIDTPCWKLHTSPLCTTN TKEGSNICLTRTDRGWYCDNAGSVSFFPQ AETCKVQSNRVFCDTMNSLTLPSEVNLCN VDIFNPKYDCKIMTSKTDVSSSVITSLGAIV SCYGKTKCTASNKNRGIIKTFSNGCDYVS NKGVDTVSVGNTLYYVNKQEGKSLYVKG EPIINFYDPLVFPS*C* EI*C*ASISQVNEKINQSL AFIRKSDELLSAIGGYIPEAPRDGQAYVR KDGEWVLLSTFL | 36 |
| LZF 125 a Sequence contains DS-Cav1 substitutions (S155C, S290C, S190F and V207L), additional substitutions D486C and D489C (bold, italicized and underlined) and a c-terminal foldon (bold), a GG linker (underlined), a thrombin cleavage site, a His tag, a SA linker (underlined) and a strep tag. | MELLILKANAITTILTAVTFCFASGQNITEE FYQSTCSAVSKGYLSALRTGWYTSVITIEL SNIKENKCNGTDAKVKLIKQELDKYKNA VTELQLLMQSTPATNNRARRELPRFMNYT LNNAKKTNVTLSKKRKRRFLGFLLGVGSA IASGVAVCKVLHLEGEVNKIKSALLSTNK AVVSLSNGVSVLTFKVLDLKNYIDKQLLPI LNKQSCSISNIETVIEFQQKNNRLLEITREF SVNAGVTTPVSTYMLTNSELLSLINDMPIT NDQKKLMSNNVQIVRQQSYSIMCIIKEEV LAYVVQLPLYGVIDTPCWKLHTSPLCTTN TKEGSNICLTRTDRGWYCDNAGSVSFFPQ AETCKVQSNRVFCDTMNSLTLPSEVNLCN VDIFNPKYDCKIMTSKTDVSSSVITSLGAIV SCYGKTKCTASNKNRGIIKTFSNGCDYVS NKGVDTVSVGNTLYYVNKQEGKSLYVKG EPIINFYDPLVFPS*C* EI*C*ASISQVNEKINQSL AFIRKSDELLSAIGGYIPEAPRDGQAYVR KDGEWVLLSTFLGGLVPRGSHHHHHH SAWSHPQFEK | 37 |
| LZF 126 Sequence contains DS-Cav1 substitutions (S155C, S290C, S190F and V207L) and additional substitutions L512Cand L513 (bold, italicized and underlined) and a c-terminal foldon (bold). | MELLILKANAITTILTAVTFCFASGQNITEE FYQSTCSAVSKGYLSALRTGWYTSVITIEL SNIKENKCNGTDAKVKLIKQELDKYKNA VTELQLLMQSTPATNNRARRELPRFMNYT LNNAKKTNVTLSKKRKRRFLGFLLGVGSA IASGVAVCKVLHLEGEVNKIKSALLSTNK AVVSLSNGVSVLTFKVLDLKNYIDKQLLPI LNKQSCSISNIETVIEFQQKNNRLLEITREF SVNAGVTTPVSTYMLTNSELLSLINDMPIT NDQKKLMSNNVQIVRQQSYSIMCIIKEEV LAYVVQLPLYGVIDTPCWKLHTSPLCTTN | 38 |

TABLE 4-continued

Antigenic Polypeptide Sequences

| Name | Sequence | SEQ ID NO: |
|---|---|---|
| | TKEGSNICLTRTDRGWYCDNAGSVSFFPQ<br>AETCKVQSNRVFCDTMNSLTLPSEVNLCN<br>VDIFNPKYDCKIMTSKTDVSSSVITSLGAIV<br>SCYGKTKCTASNKNRGIIKTFSNGCDYVS<br>NKGVDTSVGNTLYYVNKQEGKSLYVKG<br>EPIINFYDPLVFPSDEFDASISQVNEKINQSL<br>AFIRKSDE_CC_ SAIGGYIPEAPRDGQAYVR<br>KDGEWVLLSTFL | |
| LZF 126a<br>Sequence contains DS-Cav1 substitutions (S155C, S290C, S190F and V207L), additional substitutions L512C and L513C (bold, italicized and underlined), a c-terminal foldon (bold), a GG linker (underlined), a thrombin cleavage site, a His tag, a SA linker (underlined) and a strep tag. | MELLILKANAITTILTAVTFCFASGQNITEE<br>FYQSTCSAVSKGYLSALRTGWYTSVITIEL<br>SNIKENKCNGTDAKVKLIKQELDKYKNA<br>VTELQLLMQSTPATNNRARRELPRFMNYT<br>LNNAKKTNVTLSKKRKRRFLGFLLGVGSA<br>IASGVAVCKVLHLEGEVNKIKSALLSTNK<br>AVVSLSNGVSVLTFKVLDLKNYIDKQLLPI<br>LNKQSCSISNIETVIEFQQKNNRLLEITREF<br>SVNAGVTTPVSTYMLTNSELLSLINDMPIT<br>NDQKKLMSNNVQIVRQQSYSIMCIIKEEV<br>LAYVVQLPLYGVIDTPCWKLHTSPLCTTN<br>TKEGSNICLTRTDRGWYCDNAGSVSFFPQ<br>AETCKVQSNRVFCDTMNSLTLPSEVNLCN<br>VDIFNPKYDCKIMTSKTDVSSSVITSLGAIV<br>SCYGKTKCTASNKNRGIIKTFSNGCDYVS<br>NKGVDTSVGNTLYYVNKQEGKSLYVKG<br>EPIINFYDPLVFPSDEFDASISQVNEKINQSL<br>AFIRKSDE_CC_ SAIGGYIPEAPRDGQAYVR<br>KDGEWVLLSTFLGGLVPRGSHHHHHH<br>SAWSHPQFEK | 39 |
| LZF 127<br>Sequence contains DS-Cav1 substitutions (S155C, S290C, S190F and V207L) and additional substitution F505C (bold, italicized and underlined) and a c-terminal foldon (bold). | MELLILKANAITTILTAVTFCFASGQNITEE<br>FYQSTCSAVSKGYLSALRTGWYTSVITIEL<br>SNIKENKCNGTDAKVKLIKQELDKYKNA<br>VTELQLLMQSTPATNNRARRELPRFMNYT<br>LNNAKKTNVTLSKKRKRRFLGFLLGVGSA<br>IASGVAVCKVLHLEGEVNKIKSALLSTNK<br>AVVSLSNGVSVLTFKVLDLKNYIDKQLLPI<br>LNKQSCSISNIETVIEFQQKNNRLLEITREF<br>SVNAGVTTPVSTYMLTNSELLSLINDMPIT<br>NDQKKLMSNNVQIVRQQSYSIMCIIKEEV<br>LAYVVQLPLYGVIDTPCWKLHTSPLCTTN<br>TKEGSNICLTRTDRGWYCDNAGSVSFFPQ<br>AETCKVQSNRVFCDTMNSLTLPSEVNLCN<br>VDIFNPKYDCKIMTSKTDVSSSVITSLGAIV<br>SCYGKTKCTASNKNRGIIKTFSNGCDYVS<br>NKGVDTSVGNTLYYVNKQEGKSLYVKG<br>EPIINFYDPLVFPSDEFDASISQVNEKINQSL<br>_C_IRKSDELLSAIGGYIPEAPRDGQAYVR<br>KDGEWVLLSTFL | 40 |
| LZF 127a<br>Sequence contains DS-Cav1 substitutions (S155C, S290C, S190F and V207L), additional substitution F505C (bold, italicized and underlined), a c-terminal foldon (bold), a linker (underlined), a thrombin cleavage site, a His tag, a linker (underlined) and a strep tag. | MELLILKANAITTILTAVTFCFASGQNITEE<br>FYQSTCSAVSKGYLSALRTGWYTSVITIEL<br>SNIKENKCNGTDAKVKLIKQELDKYKNA<br>VTELQLLMQSTPATNNRARRELPRFMNYT<br>LNNAKKTNVTLSKKRKRRFLGFLLGVGSA<br>IASGVAVCKVLHLEGEVNKIKSALLSTNK<br>AVVSLSNGVSVLTFKVLDLKNYIDKQLLPI<br>LNKQSCSISNIETVIEFQQKNNRLLEITREF<br>SVNAGVTTPVSTYMLTNSELLSLINDMPIT<br>NDQKKLMSNNVQIVRQQSYSIMCIIKEEV<br>LAYVVQLPLYGVIDTPCWKLHTSPLCTTN<br>TKEGSNICLTRTDRGWYCDNAGSVSFFPQ<br>AETCKVQSNRVFCDTMNSLTLPSEVNLCN<br>VDIFNPKYDCKIMTSKTDVSSSVITSLGAIV<br>SCYGKTKCTASNKNRGIIKTFSNGCDYVS<br>NKGVDTSVGNTLYYVNKQEGKSLYVKG<br>EPIINFYDPLVFPSDEFDASISQVNEKINQSL<br>_C_IRKSDELLSAIGGYIPEAPRDGQAYVR<br>KDGEWVLLSTFLGGLVPRGSHHHHHH<br>SAWSHPQFEK | 41 |
| LZF 128<br>Sequence contains DS-Cav1 substitutions | MELLILKANAITTILTAVTFCFASGQNITEE<br>FYQSTCSAVSKGYLSALRTGWYTSVITIEL<br>SNIKENKCNGTDAKVKLIKQELDKYKNA<br>VTELQLLMQSTPATNNRARRELPRFMNYT | 42 |

TABLE 4-continued

Antigenic Polypeptide Sequences

| Name | Sequence | SEQ ID NO: |
|---|---|---|
| (S155C, S290C, S190F and V207L) and additional deletion of HRB domain corresponding to amino acids 482-513 and a c-terminal foldon (bold). | LNNAKKTNVTLSKKRKRRFLGFLLGVGSA IASGVAVCKVLHLEGEVNKIKSALLSTNK AVVSLSNGVSVLTFKVLDLKNYIDKQLLPI LNKQSCSISNIETVIEFQQKNNRLLEITREF SVNAGVTTPVSTYMLTNSELLSLINDMPIT NDDQKKLMSNNVQIVRQQSYSIMCIIKEEV LAYVVQLPLYGVIDTPCWKLHTSPLCTTN TKEGSNICLTRTDRGWYCDNAGSVSFFPQ AETCKVQSNRVFCDTMNSLTLPSEVNLCN VDIFNPKYDCKIMTSKTDVSSSVITSLGAIV SCYGKTKCTASNKNRGIIKTFSNGCDYVS NKGVDTVSVGNTLYYVNKQEGKSLYVKG EPIINFYDPLSAIGGYIPEAPRDGQAYVRK DGEWVLLSTFL | |
| LZF 128 a Sequence contains DS-Cav1 substitutions (S155C, S290C, S190F and V207L), additional deletion of HRB domain corresponding to amino acids 482-513, a c-terminal foldon (bold), a linker (underlined), a thrombin cleavage site, a His tag, a linker (underlined) and a strep tag. | MELLILKANAITTILTAVTFCFASGQNITEE FYQSTCSAVSKGYLSALRTGWYTSVITIEL SNIKENKCNGTDAKVKLIKQELDKYKNA VTELQLLMQSTPATNNRARRELPRFMNYT LNNAKKTNVTLSKKRKRRFLGFLLGVGSA IASGVAVCKVLHLEGEVNKIKSALLSTNK AVVSLSNGVSVLTFKVLDLKNYIDKQLLPI LNKQSCSISNIETVIEFQQKNNRLLEITREF SVNAGVTTPVSTYMLTNSELLSLINDMPIT NDDQKKLMSNNVQIVRQQSYSIMCIIKEEV LAYVVQLPLYGVIDTPCWKLHTSPLCTTN TKEGSNICLTRTDRGWYCDNAGSVSFFPQ AETCKVQSNRVFCDTMNSLTLPSEVNLCN VDIFNPKYDCKIMTSKTDVSSSVITSLGAIV SCYGKTKCTASNKNRGIIKTFSNGCDYVS NKGVDTVSVGNTLYYVNKQEGKSLYVKG EPIINFYDPLSAIGGYIPEAPRDGQAYVRK DGEWVLLSTFLGGLVPRGSHHHHHH<u>SA</u> WSHPQFEK | 43 |
| LZF 129 | MELLILKANAITTILTAVTFCFASGQNITEE FYQSTCSAVSKGYLSALRTGWYTSVITIEL SNIKENKCNGTDAKVKLIKQELDKYKNA VTELQLLM<u>GGSGGGSGGGSGS</u>AIASGV AVCKVLHLEGEVNKIKSALLSTNKAVVSL SNGVSVLTFKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLSAIGGYIPEAPRDGQAYVRKDGE WVLLSTFL | 44 |
| LZF 129a | MELLILKANAITTILTAVTFCFASGQNITEE FYQSTCSAVSKGYLSALRTGWYTSVITIEL SNIKENKCNGTDAKVKLIKQELDKYKNA VTELQLLM<u>GGSGGGSGGGSGS</u>AIASGV AVCKVLHLEGEVNKIKSALLSTNKAVVSL SNGVSVLTFKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLSAIGGYIPEAPRDGQAYVRKDGE WVLLSTFLGGLVPRGSHHHHHH<u>SA</u>WSHP QFEK | 45 |

TABLE 4-continued

Antigenic Polypeptide Sequences

| Name | Sequence | SEQ ID NO: |
|---|---|---|
| Primers | Sequences | |
| RSV A F N gene | 5' CTC AAT TTC CTC ACT TCT CCA GTG T (SEQ ID NO: 46) | |
| RSV ARN gene | 5' CTT GAT TCC TCG GTG TAC CTC TGT (SEQ ID NO: 47) | |
| RSV A FAM N gene | 5'FAM-TCC CAT TAT GCC TAG GCC AGC AGC A (BHQI) (SEQ ID NO: 48) | |

Those skilled in the art will recognize, or be able to ascertain using no more than routine experimentation, many equivalents to the specific embodiments of the disclosure described herein. Such equivalents are intended to be encompassed by the following claims.

All references, including patent documents, disclosed herein are incorporated by reference in their entirety.

```
                    SEQUENCE LISTING

Sequence total quantity: 49
SEQ ID NO: 1           moltype = AA  length = 8
FEATURE                Location/Qualifiers
REGION                 1..8
                       note = Amino Acid Linker
source                 1..8
                       mol_type = protein
                       organism = synthetic construct
SEQUENCE: 1
GGGSGGGS                                                                  8

SEQ ID NO: 2           moltype = AA  length = 10
FEATURE                Location/Qualifiers
REGION                 1..10
                       note = Amino Acid Linker
source                 1..10
                       mol_type = protein
                       organism = synthetic construct
SEQUENCE: 2
GGGSGGGSGG                                                               10

SEQ ID NO: 3           moltype = AA  length = 12
FEATURE                Location/Qualifiers
REGION                 1..12
                       note = Amino Acid Linker
source                 1..12
                       mol_type = protein
                       organism = synthetic construct
SEQUENCE: 3
GGGSGGGSGG GS                                                            12

SEQ ID NO: 4           moltype = AA  length = 14
FEATURE                Location/Qualifiers
REGION                 1..14
                       note = Amino Acid Linker
source                 1..14
                       mol_type = protein
                       organism = synthetic construct
SEQUENCE: 4
GGGSGGGSGG GSGS                                                          14

SEQ ID NO: 5           moltype = AA  length = 7
FEATURE                Location/Qualifiers
REGION                 1..7
                       note = TEV Cleavage Site
source                 1..7
                       mol_type = protein
                       organism = synthetic construct
SEQUENCE: 5
ENLYFQS                                                                   7
```

```
SEQ ID NO: 6              moltype = AA   length = 8
FEATURE                   Location/Qualifiers
REGION                    1..8
                          note = Strep Tag
source                    1..8
                          mol_type = protein
                          organism = synthetic construct
SEQUENCE: 6
WSHPQFEK                                                                  8

SEQ ID NO: 7              moltype = AA   length = 6
FEATURE                   Location/Qualifiers
REGION                    1..6
                          note = Thrombin Cleavage Site
source                    1..6
                          mol_type = protein
                          organism = synthetic construct
SEQUENCE: 7
LVPRGS                                                                    6

SEQ ID NO: 8              moltype = AA   length = 31
FEATURE                   Location/Qualifiers
REGION                    1..31
                          note = Foldon
source                    1..31
                          mol_type = protein
                          organism = synthetic construct
SEQUENCE: 8
SAIGGYIPEA PRDGQAYVRK DGEWVLLSTF L                                       31

SEQ ID NO: 9              moltype = AA   length = 25
FEATURE                   Location/Qualifiers
REGION                    1..25
                          note = Signal Sequence
source                    1..25
                          mol_type = protein
                          organism = synthetic construct
SEQUENCE: 9
MELLILKANA ITTILTAVTF CFASG                                              25

SEQ ID NO: 10             moltype = AA   length = 574
FEATURE                   Location/Qualifiers
REGION                    1..574
                          note = RSV F reference sequence
source                    1..574
                          mol_type = protein
                          organism = synthetic construct
SEQUENCE: 10
MELLILKANA ITTILTAVTF CFASGQNITE EFYQSTCSAV SKGYLSALRT GWYTSVITIE        60
LSNIKENKCN GTDAKVKLIK QELDKYKNAV TELQLLMQST PPTNNRARRE LPRFMNYTLN       120
NAKKTNVTLS KKRKRRFLGF LLGVGSAIAS GVAVSKVLHL EGEVNKIKSA LLSTNKAVVS       180
LSNGVSVLTS KVLDLKNYID KQLLPIVNKQ SCSISNIETV IEFQQKNNRL LEITREFSVN       240
AGVTTPVSTY MLTNSELLSL INDMPITNDQ KKLMSNNVQI VRQQSYSIMS IIKEEVLAYV       300
VQLPLYGVID TPCWKLHTSP LCTTNTKEGS NICLTRTDRG WYCDNAGSVS FFPQAETCKV       360
QSNRVFCDTM NSLTLPSEIN LCNVDIFNPK YDCKIMTSKT DVSSSVITSL GAIVSCYGKT       420
KCTASNKNRG IIKTFSNGCD YVSNKGMDTV SVGNTLYYVN KQEGKSLYVK GEPIINFYDP       480
LVFPSDEFDA SISQVNEKIN QSLAFIRKSD ELLHNVNAGK STTNIMITTI IIVIIVILLS       540
LIAVGLLLYC KARSTPVTLS KDQLSGINNI AFSN                                   574

SEQ ID NO: 11             moltype = AA   length = 556
FEATURE                   Location/Qualifiers
REGION                    1..556
                          note = Peptide construct
source                    1..556
                          mol_type = protein
                          organism = synthetic construct
SEQUENCE: 11
MELLILKANA ITTILTAVTF CFASGQNITE EFYQSTCSAV SKGYLSALRT GWYTSVITIE        60
LSNIKENKCN GTDAKVKLIK QELDKYKNAV TELQLLMQST PATNNRARRE LPRFMNYTLN       120
NAKKTNVTLS KKRKRRFLGF LLGVGSAIAS GVAVSKVLHL EGEVNKIKSA LLSTNKAVVS       180
LSNGVSVLTS KVLDLKNYID KQLLPIVNKQ SCSISNIETV IEFQQKNNRL LEITREFSVN       240
AGVTTPVSTY MLTNSELLSL INDMPITNDQ KKLMSNNVQI VRQQSYSIMS IIKEEVLAYV       300
VQLPLYGVID TPCWKLHTSP LCTTNTKEGS NICLTRTDRG WYCDNAGSVS FFPQAETCKV       360
QSNRVFCDTM NSLTLPSEVN LCNVDIFNPK YDCKIMTSKT DVSSSVITSL GAIVSCYGKT       420
KCTASNKNRG IIKTFSNGCD YVSNKGVDTV SVGNTLYYVN KQEGKSLYVK GEPIINFYDP       480
LVFPSDEFDA SISQVNEKIN QSLAFIRKSD ELLHNVNAGK STTNIMITTG YIPEAPRDGQ       540
AYVRKDGEWV LLSTFL                                                       556
```

```
SEQ ID NO: 12              moltype = AA  length = 605
FEATURE                    Location/Qualifiers
REGION                     1..605
                           note = Peptide construct
source                     1..605
                           mol_type = protein
                           organism = synthetic construct
SEQUENCE: 12
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVSKVLHL EGEVNKIKSA LLSTNKAVVS   180
LSNGVSVLTS KVLDLKNYID KQLLPIVNKQ SCSISNIETV IEFQQKNNRL LEITREFSVN   240
AGVTTPVSTY MLTNSELLSL INDMPITNDQ KKLMSNNVQI VRQQSYSIMS IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHNVNAGK STTNIMITTG YIPEAPRDGQ   540
AYVRKDGEWV LLSTFLENLY FQSWSHPQFE KGGGSGGGGS GGSWSHPQFE KGSGSGSHHH   600
HHHHH                                                               605

SEQ ID NO: 13              moltype = AA  length = 544
FEATURE                    Location/Qualifiers
REGION                     1..544
                           note = Peptide construct
source                     1..544
                           mol_type = protein
                           organism = synthetic construct
SEQUENCE: 13
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLSAIGGYI PEAPRDGQAY VRKDGEWVLL   540
STFL                                                                544

SEQ ID NO: 14              moltype = AA  length = 503
FEATURE                    Location/Qualifiers
REGION                     1..503
                           note = Peptide Construct
source                     1..503
                           mol_type = protein
                           organism = synthetic construct
SEQUENCE: 14
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMGGG SGGGSAIASG VAVCKVLHLE   120
GEVNKIKSAL LSTNKAVVSL SNGVSVLTFK VLDLKNYIDK QLLPILNKQS CSISNIETVI   180
EFQQKNNRLL EITREFSVNA GVTTPVSTYM LTNSELLSLI NDMPITNDQK KLMSNNVQIV   240
RQQSYSIMCI IKEEVLAYVV QLPLYGVIDT PCWKLHTSPL CTTNTKEGSN ICLTRTDRGW   300
YCDNAGSVSF FPQAETCKVQ SNRVFCDTMN SLTLPSEVNL CNVDIFNPKY DCKIMTSKTD   360
VSSSVITSLG AIVSCYGKTK CTASNKNRGI IKTFSNGCDY VSNKGVDTVS VGNTLYYVNK   420
QEGKSLYVKG EPIINFYDPL VFPSDEFDAS ISQVNEKINQ SLAFIRKSDE LLSAIGGYIP   480
EAPRDGQAYV RKDGEWVLLS TFL                                           503

SEQ ID NO: 15              moltype = AA  length = 527
FEATURE                    Location/Qualifiers
REGION                     1..527
                           note = Peptide construct
source                     1..527
                           mol_type = protein
                           organism = synthetic construct
SEQUENCE: 15
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMGGG SGGGSAIASG VAVCKVLHLE   120
GEVNKIKSAL LSTNKAVVSL SNGVSVLTFK VLDLKNYIDK QLLPILNKQS CSISNIETVI   180
EFQQKNNRLL EITREFSVNA GVTTPVSTYM LTNSELLSLI NDMPITNDQK KLMSNNVQIV   240
RQQSYSIMCI IKEEVLAYVV QLPLYGVIDT PCWKLHTSPL CTTNTKEGSN ICLTRTDRGW   300
YCDNAGSVSF FPQAETCKVQ SNRVFCDTMN SLTLPSEVNL CNVDIFNPKY DCKIMTSKTD   360
VSSSVITSLG AIVSCYGKTK CTASNKNRGI IKTFSNGCDY VSNKGVDTVS VGNTLYYVNK   420
QEGKSLYVKG EPIINFYDPL VFPSDEFDAS ISQVNEKINQ SLAFIRKSDE LLSAIGGYIP   480
EAPRDGQAYV RKDGEWVLLS TFLGGLVPRG SHHHHHHSAW SHPQFEK                 527

SEQ ID NO: 16              moltype = AA  length = 505
FEATURE                    Location/Qualifiers
REGION                     1..505
                           note = Peptide construct
```

```
                        -continued source                   1..505
                         mol_type = protein
                         organism = synthetic construct
SEQUENCE: 16
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMGGG SGGGSGGAIA SGVAVCKVLH  120
LEGEVNKIKS ALLSTNKAVV SLSNGVSVLT FKVLDLKNYI DKQLLPILNK QSCSISNIET  180
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSLTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGKSLYV KGEPIINFYD PLVFPSDEFD ASISQVNEKI NQSLAFIRKS DELLSAIGGY  480
IPEAPRDGQA YVRKDGEWVL LSTFL                                       505

SEQ ID NO: 17            moltype = AA  length = 529
FEATURE                  Location/Qualifiers
REGION                   1..529
                         note = Peptide Construct
source                   1..529
                         mol_type = protein
                         organism = synthetic construct
SEQUENCE: 17
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMGGG SGGGSGGAIA SGVAVCKVLH  120
LEGEVNKIKS ALLSTNKAVV SLSNGVSVLT FKVLDLKNYI DKQLLPILNK QSCSISNIET  180
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSLTLPSEV NLCNVDIFNP KYDCKIMTSK  360
TDVSSSVITS LGAIVSCYGK TKCTASNKNR GIIKTFSNGC DYVSNKGVDT VSVGNTLYYV  420
NKQEGKSLYV KGEPIINFYD PLVFPSDEFD ASISQVNEKI NQSLAFIRKS DELLSAIGGY  480
IPEAPRDGQA YVRKDGEWVL LSTFLGGLVP RGSHHHHHH AWSHPQFEK               529

SEQ ID NO: 18            moltype = AA  length = 507
FEATURE                  Location/Qualifiers
REGION                   1..507
                         note = Peptide construct
source                   1..507
                         mol_type = protein
                         organism = synthetic construct
SEQUENCE: 18
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMGGG SGGGSGGGSA IASGVAVCK   120
LHLEGEVNKI KSALLSTNKA VVSLSNGVSV LTFKVLDLKN YIDKQLLPIL NKQSCSISNI  180
ETVIEFQQKN NRLLEITREF SVNAGVTTPV STYMLTNSEL LSLINDMPIT NDQKKLMSNN  240
VQIVRQQSYS IMCIIKEEVL AYVVQLPLYG VIDTPCWKLH TSPLCTTNTK EGSNICLTRT  300
DRGWYCDNAG SVSFFPQAET CKVQSNRVFC DTMNSLTLPS EVNLCNVDIF NPKYDCKIMT  360
SKTDVSSSVI TSLGAIVSCY GKTKCTASNK NRGIIKTFSN GCDYVSNKGV DTVSVGNTLY  420
YVNKQEGKSL YVKGEPIINF YDPLVFPSDE FDASISQVNE KINQSLAFIR KSDELLSAIG  480
GYIPEAPRDG QAYVRKDGEW VLLSTFL                                     507

SEQ ID NO: 19            moltype = AA  length = 531
FEATURE                  Location/Qualifiers
REGION                   1..531
                         note = Peptide construct
source                   1..531
                         mol_type = protein
                         organism = synthetic construct
SEQUENCE: 19
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMGGG SGGGSGGGSA IASGVAVCKV  120
LHLEGEVNKI KSALLSTNKA VVSLSNGVSV LTFKVLDLKN YIDKQLLPIL NKQSCSISNI  180
ETVIEFQQKN NRLLEITREF SVNAGVTTPV STYMLTNSEL LSLINDMPIT NDQKKLMSNN  240
VQIVRQQSYS IMCIIKEEVL AYVVQLPLYG VIDTPCWKLH TSPLCTTNTK EGSNICLTRT  300
DRGWYCDNAG SVSFFPQAET CKVQSNRVFC DTMNSLTLPS EVNLCNVDIF NPKYDCKIMT  360
SKTDVSSSVI TSLGAIVSCY GKTKCTASNK NRGIIKTFSN GCDYVSNKGV DTVSVGNTLY  420
YVNKQEGKSL YVKGEPIINF YDPLVFPSDE FDASISQVNE KINQSLAFIR KSDELLSAIG  480
GYIPEAPRDG QAYVRKDGEW VLLSTFLGGL VPRGSHHHHH HSAWSHPQFE K           531

SEQ ID NO: 20            moltype = AA  length = 509
FEATURE                  Location/Qualifiers
REGION                   1..509
                         note = Peptide construct
source                   1..509
                         mol_type = protein
                         organism = synthetic construct
SEQUENCE: 20
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMGGG SGGGSGGGSG SAIASGVAVC  120
KVLHLEGEVN KIKSALLSTN KAVVSLSNGV SVLTFKVLDL KNYIDKQLLP ILNKQSCSIS  180
```

```
NIETVIEFQQ KNNRLLEITR EFSVNAGVTT PVSTYMLTNS ELLSLINDMP ITNDQKKLMS    240
NNVQIVRQQS YSIMCIIKEE VLAYVVQLPL YGVIDTPCWK LHTSPLCTTN TKEGSNICLT    300
RTDRGWYCDN AGSVSFFPQA ETCKVQSNRV FCDTMNSLTL PSEVNLCNVD IFNPKYDCKI    360
MTSKTDVSSS VITSLGAIVS CYGKTKCTAS NKNRGIIKTF SNGCDYVSNK GVDTVSVGNT    420
LYYVNKQEGK SLYVKGEPII NFYDPLVFPS DEFDASISQV NEKINQSLAF IRKSDELLSA    480
IGGYIPEAPR DGQAYVRKDG EWVLLSTFL                                     509

SEQ ID NO: 21              moltype = AA  length = 533
FEATURE                    Location/Qualifiers
REGION                     1..533
                           note = Peptide construct
source                     1..533
                           mol_type = protein
                           organism = synthetic construct
SEQUENCE: 21
MELLILKANA ITTILTAVTF CFASGQNITE EFYQSTCSAV SKGYLSALRT GWYTSVITIE     60
LSNIKENKCN GTDAKVKLIK QELDKYKNAV TELQLLMGGG SGGGSGGGSG SAIASGVAVC    120
KVLHLEGEVN KIKSALLSTN KAVVSLSNGV SVLTFKVLDL KNYIDKQLLP ILNKQSCSIS    180
NIETVIEFQQ KNNRLLEITR EFSVNAGVTT PVSTYMLTNS ELLSLINDMP ITNDQKKLMS    240
NNVQIVRQQS YSIMCIIKEE VLAYVVQLPL YGVIDTPCWK LHTSPLCTTN TKEGSNICLT    300
RTDRGWYCDN AGSVSFFPQA ETCKVQSNRV FCDTMNSLTL PSEVNLCNVD IFNPKYDCKI    360
MTSKTDVSSS VITSLGAIVS CYGKTKCTAS NKNRGIIKTF SNGCDYVSNK GVDTVSVGNT    420
LYYVNKQEGK SLYVKGEPII NFYDPLVFPS DEFDASISQV NEKINQSLAF IRKSDELLSA    480
IGGYIPEAPR DGQAYVRKDG EWVLLSTFLG GLVPRGSHHH HHHSAWSHPQ FEK           533

SEQ ID NO: 22              moltype = AA  length = 509
FEATURE                    Location/Qualifiers
REGION                     1..509
                           note = Peptide construct
source                     1..509
                           mol_type = protein
                           organism = synthetic construct
SEQUENCE: 22
MELLILKANA ITTILTAVTF CFASGQNITE EFYQSTCSAV SKGYLSALRT GWYTSVITIE     60
LSNIKENKCN GTDAKVKLIK QELDKYKNAV TELQLLMGGG SGGGSGGGSG SAIASGVAVC    120
KVLHLEGEVN KIKSALLSTN KAVVCLSNGV CVLTFKVLDL KNYIDKQLLP ILNKQSCSIS    180
NIETVIEFQQ KNNRLLEITR EFSVNAGVTT PVSTYMLTNS ELLSLINDMP ITNDQKKLMS    240
NNVQIVRQQS YSIMCIIKEE VLAYVVQLPL YGVIDTPCWK LHTSPLCTTN TKEGSNICLT    300
RTDRGWYCDN AGSVSFFPQA ETCKVQSNRV FCDTMNSLTL PSEVNLCNVD IFNPKYDCKI    360
MTSKTDVSSS VITSLGAIVS CYGKTKCTAS NKNRGIIKTF SNGCDYVSNK GVDTVSVGNT    420
LYYVNKQEGK SLYVKGEPII NFYDPLVFPS DEFDASISQV NEKINQSLAF IRKSDELLSA    480
IGGYIPEAPR DGQAYVRKDG EWVLLSTFL                                     509

SEQ ID NO: 23              moltype = AA  length = 533
FEATURE                    Location/Qualifiers
REGION                     1..533
                           note = Peptide construct
source                     1..533
                           mol_type = protein
                           organism = synthetic construct
SEQUENCE: 23
MELLILKANA ITTILTAVTF CFASGQNITE EFYQSTCSAV SKGYLSALRT GWYTSVITIE     60
LSNIKENKCN GTDAKVKLIK QELDKYKNAV TELQLLMGGG SGGGSGGGSG SAIASGVAVC    120
KVLHLEGEVN KIKSALLSTN KAVVCLSNGV CVLTFKVLDL KNYIDKQLLP ILNKQSCSIS    180
NIETVIEFQQ KNNRLLEITR EFSVNAGVTT PVSTYMLTNS ELLSLINDMP ITNDQKKLMS    240
NNVQIVRQQS YSIMCIIKEE VLAYVVQLPL YGVIDTPCWK LHTSPLCTTN TKEGSNICLT    300
RTDRGWYCDN AGSVSFFPQA ETCKVQSNRV FCDTMNSLTL PSEVNLCNVD IFNPKYDCKI    360
MTSKTDVSSS VITSLGAIVS CYGKTKCTAS NKNRGIIKTF SNGCDYVSNK GVDTVSVGNT    420
LYYVNKQEGK SLYVKGEPII NFYDPLVFPS DEFDASISQV NEKINQSLAF IRKSDELLSA    480
IGGYIPEAPR DGQAYVRKDG EWVLLSTFLG GLVPRGSHHH HHHSAWSHPQ FEK           533

SEQ ID NO: 24              moltype = AA  length = 509
FEATURE                    Location/Qualifiers
REGION                     1..509
                           note = Peptide construct
source                     1..509
                           mol_type = protein
                           organism = synthetic construct
SEQUENCE: 24
MELLILKANA ITTILTAVTF CFASGQNITE EFYQSTCSAV SKGYLSALRT GWYTSVITIE     60
LSNIKENKCN GTDAKVKLIK QELDKYKNAV TELQLLMGGG SGGGSGGGSG SAIASGVAVC    120
KVLHLEGEVN KIKSALLSTN KAVVSLSNGV SVLTFKVLDL KNYIDKQLLP ILNKQSCSIS    180
NIETVIEFQQ KNNRLLEITR EFSVNAGVTT PVSTYMLTNS ELLSLINDMP ITNDQKKLMS    240
NNVQIVRQQS YSIMCIIKEE VLAYVVQLPL YGVIDTPCWK LHTSPLCTTN TKEGSNICLT    300
RTDRGWYCDN AGSVSFFPQA ETCKVQSNRV FCDTMNSLTL PSEVNLCNVD IFNPKYDCKI    360
MTSKTDVSSS VITSLGAIVS CYGKTKCTAS NKNRGIIKTF SNGCDYVSNK GVDTVSVGNT    420
LYYVNKQEGK SLYVKGEPII NFYDPLVFPS CEFDCSISQV NEKINQSLAF IRKSDELLSA    480
IGGYIPEAPR DGQAYVRKDG EWVLLSTFL                                     509
```

```
SEQ ID NO: 25              moltype = AA  length = 533
FEATURE                    Location/Qualifiers
REGION                     1..533
                           note = Peptide construct
source                     1..533
                           mol_type = protein
                           organism = synthetic construct
SEQUENCE: 25
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMGGG SGGGSGGGSG SAIASGVAVC  120
KVLHLEGEVN KIKSALLSTN KAVVSLSNGV SVLTFKVLDL KNYIDKQLLP ILNKQSCSIS  180
NIETVIEFQQ KNNRLLEITR EFSVNAGVTT PVSTYMLTNS ELLSLINDMP ITNDQKKLMS  240
NNVQIVRQQS YSIMCIIKEE VLAYVVQLPL YGVIDTPCWK LHTSPLCTTN TKEGSNICLT  300
RTDRGWYCDN AGSVSFFPQA ETCKVQSNRV FCDTMNSLTL PSEVNLCNVD IFNPKYDCKI  360
MTSKTDVSSS VITSLGAIVS CYGKTKCTAS NKNRGIIKTF SNGCDYVSNK GVDTVSVGNT  420
LYYVNKQEGK SLYVKGEPII NFYDPLVFPS CEFDCSISQV NEKINQSLAF IRKSDELLSA  480
IGGYIPEAPR DGQAYVRKDG EWVLLSTFLG GLVPRGSHHH HHHSAWSHPQ FEK         533

SEQ ID NO: 26              moltype = AA  length = 509
FEATURE                    Location/Qualifiers
REGION                     1..509
                           note = Peptide construct
source                     1..509
                           mol_type = protein
                           organism = synthetic construct
SEQUENCE: 26
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMGGG SGGGSGGGSG SAIASGVAVC  120
KVLHLEGEVN KIKSALLSTN KAVVSLSNGV SVLTFKVLDL KNYIDKQLLP ILNKQSCSIS  180
NIETVIEFQQ KNNRLLEITR EFSVNAGVTT PVSTYMLTNS ELLSLINDMP ITNDQKKLMS  240
NNVQIVRQQS YSIMCIIKEE VLAYVVQLPL YGVIDTPCWK LHTSPLCTTN TKEGSNICLT  300
RTDRGWYCDN AGSVSFFPQA ETCKVQSNRV FCDTMNSLTL PSEVNLCNVD IFNPKYDCKI  360
MTSKTDVSSS VITSLGAIVS CYGKTKCTAS NKNRGIIKTF SNGCDYVSNK GVDTVSVGNT  420
LYYVNKQEGK SLYVKGEPII NFYDPLVFPS CEFCASISQV NEKINQSLAF IRKSDELLSA  480
IGGYIPEAPR DGQAYVRKDG EWVLLSTFL                                    509

SEQ ID NO: 27              moltype = AA  length = 533
FEATURE                    Location/Qualifiers
REGION                     1..533
                           note = Peptide construct
source                     1..533
                           mol_type = protein
                           organism = synthetic construct
SEQUENCE: 27
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMGGG SGGGSGGGSG SAIASGVAVC  120
KVLHLEGEVN KIKSALLSTN KAVVSLSNGV SVLTFKVLDL KNYIDKQLLP ILNKQSCSIS  180
NIETVIEFQQ KNNRLLEITR EFSVNAGVTT PVSTYMLTNS ELLSLINDMP ITNDQKKLMS  240
NNVQIVRQQS YSIMCIIKEE VLAYVVQLPL YGVIDTPCWK LHTSPLCTTN TKEGSNICLT  300
RTDRGWYCDN AGSVSFFPQA ETCKVQSNRV FCDTMNSLTL PSEVNLCNVD IFNPKYDCKI  360
MTSKTDVSSS VITSLGAIVS CYGKTKCTAS NKNRGIIKTF SNGCDYVSNK GVDTVSVGNT  420
LYYVNKQEGK SLYVKGEPII NFYDPLVFPS CEFCASISQV NEKINQSLAF IRKSDELLSA  480
IGGYIPEAPR DGQAYVRKDG EWVLLSTFLG GLVPRGSHHH HHHSAWSHPQ FEK         533

SEQ ID NO: 28              moltype = AA  length = 509
FEATURE                    Location/Qualifiers
REGION                     1..509
                           note = Peptide construct
source                     1..509
                           mol_type = protein
                           organism = synthetic construct
SEQUENCE: 28
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMGGG SGGGSGGGSG SAIASGVAVC  120
KVLHLEGEVN KIKSALLSTN KAVVSLSNGV SVLTFKVLDL KNYIDKQLLP ILNKQSCSIS  180
NIETVIEFQQ KNNRLLEITR EFSVNAGVTT PVSTYMLTNS ELLSLINDMP ITNDQKKLMS  240
NNVQIVRQQS YSIMCIIKEE VLAYVVQLPL YGVIDTPCWK LHTSPLCTTN TKEGSNICLT  300
RTDRGWYCDN AGSVSFFPQA ETCKVQSNRV FCDTMNSLTL PSEVNLCNVD IFNPKYDCKI  360
MTSKTDVSSS VITSLGAIVS CYGKTKCTAS NKNRGIIKTF SNGCDYVSNK GVDTVSVGNT  420
LYYVNKQEGK SLYVKGEPII NFYDPLVFPS DEFDASISQV NEKINQSLAF IRKSDECCSA  480
IGGYIPEAPR DGQAYVRKDG EWVLLSTFL                                    509

SEQ ID NO: 29              moltype = AA  length = 533
FEATURE                    Location/Qualifiers
REGION                     1..533
                           note = Peptide construct
source                     1..533
                           mol_type = protein
                           organism = synthetic construct
```

```
SEQUENCE: 29
MELLILKANA  ITTILTAVTF  CFASGQNITE  EFYQSTCSAV  SKGYLSALRT  GWYTSVITIE   60
LSNIKENKCN  GTDAKVKLIK  QELDKYKNAV  TELQLLMGGG  SGGGSGGGSG  SAIASGVAVC  120
KVLHLEGEVN  KIKSALLSTN  KAVVSLSNGV  SVLTFKVLDL  KNYIDKQLLP  ILNKQSCSIS  180
NIETVIEFQQ  KNNRLLEITR  EFSVNAGVTT  PVSTYMLTNS  ELLSLINDMP  ITNDQKKLMS  240
NNVQIVRQQS  YSIMCIIKEE  VLAYVVQLPL  YGVIDTPCWK  LHTSPLCTTN  TKEGSNICLT  300
RTDRGWYCDN  AGSVSFFPQA  ETCKVQSNRV  FCDTMNSLTL  PSEVNLCNVD  IFNPKYDCKI  360
MTSKTDVSSS  VITSLGAIVS  CYGKTKCTAS  NKNRGIIKTF  SNGCDYVSNK  GVDTVSVGNT  420
LYYVNKQEGK  SLYVKGEPII  NFYDPLVFPS  DEFDASISQV  NEKINQSLAF  IRKSDECCSA  480
IGGYIPEAPR  DGQAYVRKDG  EWVLLSTFLG  GLVPRGSHHH  HHHSAWSHPQ  FEK         533

SEQ ID NO: 30           moltype = AA   length = 509
FEATURE                 Location/Qualifiers
REGION                  1..509
                        note = Peptide construct
source                  1..509
                        mol_type = protein
                        organism = synthetic construct
SEQUENCE: 30
MELLILKANA  ITTILTAVTF  CFASGQNITE  EFYQSTCSAV  SKGYLSALRT  GWYTSVITIE   60
LSNIKENKCN  GTDAKVKLIK  QELDKYKNAV  TELQLLMGGG  SGGGSGGGSG  SAIASGVAVC  120
KVLHLEGEVN  KIKSALLSTN  KAVVSLSNGV  SVLTFKVLDL  KNYIDKQLLP  ILNKQSCSIS  180
NIETVIEFQQ  KNNRLLEITR  EFSVNAGVTT  PVSTYMLTNS  ELLSLINDMP  ITNDQKKLMS  240
NNVQIVRQQS  YSIMCIIKEE  VLAYVVQLPL  YGVIDTPCWK  LHTSPLCTTN  TKEGSNICLT  300
RTDRGWYCDN  AGSVSFFPQA  ETCKVQSNRV  FCDTMNSLTL  PSEVNLCNVD  IFNPKYDCKI  360
MTSKTDVSSS  VITSLGAIVS  CYGKTKCTAS  NKNRGIIKTF  SNGCDYVSNK  GVDTVSVGNT  420
LYYVNKQEGK  SLYVKGEPII  NFYDPLVFPS  DEFDASISQV  NEKINQSLAC  IRKSDELLSA  480
IGGYIPEAPR  DGQAYVRKDG  EWVLLSTFL                                       509

SEQ ID NO: 31           moltype = AA   length = 533
FEATURE                 Location/Qualifiers
REGION                  1..533
                        note = Peptide construct
source                  1..533
                        mol_type = protein
                        organism = synthetic construct
SEQUENCE: 31
MELLILKANA  ITTILTAVTF  CFASGQNITE  EFYQSTCSAV  SKGYLSALRT  GWYTSVITIE   60
LSNIKENKCN  GTDAKVKLIK  QELDKYKNAV  TELQLLMGGG  SGGGSGGGSG  SAIASGVAVC  120
KVLHLEGEVN  KIKSALLSTN  KAVVSLSNGV  SVLTFKVLDL  KNYIDKQLLP  ILNKQSCSIS  180
NIETVIEFQQ  KNNRLLEITR  EFSVNAGVTT  PVSTYMLTNS  ELLSLINDMP  ITNDQKKLMS  240
NNVQIVRQQS  YSIMCIIKEE  VLAYVVQLPL  YGVIDTPCWK  LHTSPLCTTN  TKEGSNICLT  300
RTDRGWYCDN  AGSVSFFPQA  ETCKVQSNRV  FCDTMNSLTL  PSEVNLCNVD  IFNPKYDCKI  360
MTSKTDVSSS  VITSLGAIVS  CYGKTKCTAS  NKNRGIIKTF  SNGCDYVSNK  GVDTVSVGNT  420
LYYVNKQEGK  SLYVKGEPII  NFYDPLVFPS  DEFDASISQV  NEKINQSLAC  IRKSDELLSA  480
IGGYIPEAPR  DGQAYVRKDG  EWVLLSTFLG  GLVPRGSHHH  HHHSAWSHPQ  FEK         533

SEQ ID NO: 32           moltype = AA   length = 544
FEATURE                 Location/Qualifiers
REGION                  1..544
                        note = Peptide construct
source                  1..544
                        mol_type = protein
                        organism = synthetic construct
SEQUENCE: 32
MELLILKANA  ITTILTAVTF  CFASGQNITE  EFYQSTCSAV  SKGYLSALRT  GWYTSVITIE   60
LSNIKENKCN  GTDAKVKLIK  QELDKYKNAV  TELQLLMQST  PATNNRARRE  LPRFMNYTLN  120
NAKKTNVTLS  KKRKRRFLGF  LLGVGSAIAS  GVAVCKVLHL  EGEVNKIKSA  LLSTNKAVVC  180
LSNGVCVLTF  KVLDLKNYID  KQLLPILNKQ  SCSISNIETV  IEFQQKNNRL  LEITREFSVN  240
AGVTTPVSTY  MLTNSELLSL  INDMPITNDQ  KKLMSNNVQI  VRQQSYSIMC  IIKEEVLAYV  300
VQLPLYGVID  TPCWKLHTSP  LCTTNTKEGS  NICLTRTDRG  WYCDNAGSVS  FFPQAETCKV  360
QSNRVFCDTM  NSLTLPSEVN  LCNVDIFNPK  YDCKIMTSKT  DVSSSVITSL  GAIVSCYGKT  420
KCTASNKNRG  IIKTFSNGCD  YVSNKGVDTV  SVGNTLYYVN  KQEGKSLYVK  GEPIINFYDP  480
LVFPSDEFDA  SISQVNEKIN  QSLAFIRKSD  ELLSAIGGYI  PEAPRDGQAY  VRKDGEWVLL  540
STFL                                                                    544

SEQ ID NO: 33           moltype = AA   length = 568
FEATURE                 Location/Qualifiers
REGION                  1..568
                        note = Peptide construct
source                  1..568
                        mol_type = protein
                        organism = synthetic construct
SEQUENCE: 33
MELLILKANA  ITTILTAVTF  CFASGQNITE  EFYQSTCSAV  SKGYLSALRT  GWYTSVITIE   60
LSNIKENKCN  GTDAKVKLIK  QELDKYKNAV  TELQLLMQST  PATNNRARRE  LPRFMNYTLN  120
NAKKTNVTLS  KKRKRRFLGF  LLGVGSAIAS  GVAVCKVLHL  EGEVNKIKSA  LLSTNKAVVC  180
LSNGVCVLTF  KVLDLKNYID  KQLLPILNKQ  SCSISNIETV  IEFQQKNNRL  LEITREFSVN  240
AGVTTPVSTY  MLTNSELLSL  INDMPITNDQ  KKLMSNNVQI  VRQQSYSIMC  IIKEEVLAYV  300
```

```
VQLPLYGVID TPCWKLHTSP LCTTNTKEGS NICLTRTDRG WYCDNAGSVS FFPQAETCKV    360
QSNRVFCDTM NSLTLPSEVN LCNVDIFNPK YDCKIMTSKT DVSSSVITSL GAIVSCYGKT    420
KCTASNKNRG IIKTFSNGCD YVSNKGVDTV SVGNTLYYVN KQEGKSLYVK GEPIINFYDP    480
LVFPSDEFDA SISQVNEKIN QSLAFIRKSD ELLSAIGGYI PEAPRDGQAY VRKDGEWVLL    540
STFLGGLVPR GSHHHHHHSA WSHPQFEK                                      568

SEQ ID NO: 34           moltype = AA  length = 544
FEATURE                 Location/Qualifiers
REGION                  1..544
                        note = Peptide construct
source                  1..544
                        mol_type = protein
                        organism = synthetic construct
SEQUENCE: 34
MELLILKANA ITTILTAVTF CFASGQNITE EFYQSTCSAV SKGYLSALRT GWYTSVITIE     60
LSNIKENKCN GTDAKVKLIK QELDKYKNAV TELQLLMQST PATNNRARRE LPRFMNYTLN    120
NAKKTNVTLS KKRKRRFLGF LLGVGSAIAS GVAVCKVLHL EGEVNKIKSA LLSTNKAVVS    180
LSNGVSVLTF KVLDLKNYID KQLLPILNKQ SCSISNIETV IEFQQKNNRL LEITREFSVN    240
AGVTTPVSTY MLTNSELLSL INDMPITNDQ KKLMSNNVQI VRQQSYSIMC IIKEEVLAYV    300
VQLPLYGVID TPCWKLHTSP LCTTNTKEGS NICLTRTDRG WYCDNAGSVS FFPQAETCKV    360
QSNRVFCDTM NSLTLPSEVN LCNVDIFNPK YDCKIMTSKT DVSSSVITSL GAIVSCYGKT    420
KCTASNKNRG IIKTFSNGCD YVSNKGVDTV SVGNTLYYVN KQEGKSLYVK GEPIINFYDP    480
LVFPSCEFDC SISQVNEKIN QSLAFIRKSD ELLSAIGGYI PEAPRDGQAY VRKDGEWVLL    540
STFL                                                                544

SEQ ID NO: 35           moltype = AA  length = 568
FEATURE                 Location/Qualifiers
REGION                  1..568
                        note = Peptide construct
source                  1..568
                        mol_type = protein
                        organism = synthetic construct
SEQUENCE: 35
MELLILKANA ITTILTAVTF CFASGQNITE EFYQSTCSAV SKGYLSALRT GWYTSVITIE     60
LSNIKENKCN GTDAKVKLIK QELDKYKNAV TELQLLMQST PATNNRARRE LPRFMNYTLN    120
NAKKTNVTLS KKRKRRFLGF LLGVGSAIAS GVAVCKVLHL EGEVNKIKSA LLSTNKAVVS    180
LSNGVSVLTF KVLDLKNYID KQLLPILNKQ SCSISNIETV IEFQQKNNRL LEITREFSVN    240
AGVTTPVSTY MLTNSELLSL INDMPITNDQ KKLMSNNVQI VRQQSYSIMC IIKEEVLAYV    300
VQLPLYGVID TPCWKLHTSP LCTTNTKEGS NICLTRTDRG WYCDNAGSVS FFPQAETCKV    360
QSNRVFCDTM NSLTLPSEVN LCNVDIFNPK YDCKIMTSKT DVSSSVITSL GAIVSCYGKT    420
KCTASNKNRG IIKTFSNGCD YVSNKGVDTV SVGNTLYYVN KQEGKSLYVK GEPIINFYDP    480
LVFPSCEFDC SISQVNEKIN QSLAFIRKSD ELLSAIGGYI PEAPRDGQAY VRKDGEWVLL    540
STFLGGLVPR GSHHHHHHSA WSHPQFEK                                      568

SEQ ID NO: 36           moltype = AA  length = 544
FEATURE                 Location/Qualifiers
REGION                  1..544
                        note = Peptide construct
source                  1..544
                        mol_type = protein
                        organism = synthetic construct
SEQUENCE: 36
MELLILKANA ITTILTAVTF CFASGQNITE EFYQSTCSAV SKGYLSALRT GWYTSVITIE     60
LSNIKENKCN GTDAKVKLIK QELDKYKNAV TELQLLMQST PATNNRARRE LPRFMNYTLN    120
NAKKTNVTLS KKRKRRFLGF LLGVGSAIAS GVAVCKVLHL EGEVNKIKSA LLSTNKAVVS    180
LSNGVSVLTF KVLDLKNYID KQLLPILNKQ SCSISNIETV IEFQQKNNRL LEITREFSVN    240
AGVTTPVSTY MLTNSELLSL INDMPITNDQ KKLMSNNVQI VRQQSYSIMC IIKEEVLAYV    300
VQLPLYGVID TPCWKLHTSP LCTTNTKEGS NICLTRTDRG WYCDNAGSVS FFPQAETCKV    360
QSNRVFCDTM NSLTLPSEVN LCNVDIFNPK YDCKIMTSKT DVSSSVITSL GAIVSCYGKT    420
KCTASNKNRG IIKTFSNGCD YVSNKGVDTV SVGNTLYYVN KQEGKSLYVK GEPIINFYDP    480
LVFPSCEFCA SISQVNEKIN QSLAFIRKSD ELLSAIGGYI PEAPRDGQAY VRKDGEWVLL    540
STFL                                                                544

SEQ ID NO: 37           moltype = AA  length = 568
FEATURE                 Location/Qualifiers
REGION                  1..568
                        note = Peptide construct
source                  1..568
                        mol_type = protein
                        organism = synthetic construct
SEQUENCE: 37
MELLILKANA ITTILTAVTF CFASGQNITE EFYQSTCSAV SKGYLSALRT GWYTSVITIE     60
LSNIKENKCN GTDAKVKLIK QELDKYKNAV TELQLLMQST PATNNRARRE LPRFMNYTLN    120
NAKKTNVTLS KKRKRRFLGF LLGVGSAIAS GVAVCKVLHL EGEVNKIKSA LLSTNKAVVS    180
LSNGVSVLTF KVLDLKNYID KQLLPILNKQ SCSISNIETV IEFQQKNNRL LEITREFSVN    240
AGVTTPVSTY MLTNSELLSL INDMPITNDQ KKLMSNNVQI VRQQSYSIMC IIKEEVLAYV    300
VQLPLYGVID TPCWKLHTSP LCTTNTKEGS NICLTRTDRG WYCDNAGSVS FFPQAETCKV    360
QSNRVFCDTM NSLTLPSEVN LCNVDIFNPK YDCKIMTSKT DVSSSVITSL GAIVSCYGKT    420
KCTASNKNRG IIKTFSNGCD YVSNKGVDTV SVGNTLYYVN KQEGKSLYVK GEPIINFYDP    480
```

```
LVFPSCEFCA SISQVNEKIN QSLAFIRKSD ELLSAIGGYI PEAPRDGQAY VRKDGEWVLL    540
STFLGGLVPR GSHHHHHHSA WSHPQFEK                                       568

SEQ ID NO: 38            moltype = AA  length = 544
FEATURE                  Location/Qualifiers
REGION                   1..544
                         note = Peptide construct
source                   1..544
                         mol_type = protein
                         organism = synthetic construct
SEQUENCE: 38
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN    120
NAKKTNVTLS KKRKRRFLGF LLGVGSAIAS GVAVCKVLHL EGEVNKIKSA LLSTNKAVVS    180
LSNGVSVLTF KVLDLKNYID KQLLPILNKQ SCSISNIETV IEFQQKNNRL LEITREFSVN    240
AGVTTPVSTY MLTNSELLSL INDMPITNDQ KKLMSNNVQI VRQQSYSIMC IIKEEVLAYV    300
VQLPLYGVID TPCWKLHTSP LCTTNTKEGS NICLTRTDRG WYCDNAGSVS FFPQAETCKV    360
QSNRVFCDTM NSLTLPSEVN LCNVDIFNPK YDCKIMTSKT DVSSSVITSL GAIVSCYGKT    420
KCTASNKNRG IIKTFSNGCD YVSNKGVDTV SVGNTLYYVN KQEGKSLYVK GEPIINFYDP    480
LVFPSDEFDA SISQVNEKIN QSLAFIRKSD ECCSAIGGYI PEAPRDGQAY VRKDGEWVLL    540
STFL                                                                 544

SEQ ID NO: 39            moltype = AA  length = 568
FEATURE                  Location/Qualifiers
REGION                   1..568
                         note = Peptide construct
source                   1..568
                         mol_type = protein
                         organism = synthetic construct
SEQUENCE: 39
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN    120
NAKKTNVTLS KKRKRRFLGF LLGVGSAIAS GVAVCKVLHL EGEVNKIKSA LLSTNKAVVS    180
LSNGVSVLTF KVLDLKNYID KQLLPILNKQ SCSISNIETV IEFQQKNNRL LEITREFSVN    240
AGVTTPVSTY MLTNSELLSL INDMPITNDQ KKLMSNNVQI VRQQSYSIMC IIKEEVLAYV    300
VQLPLYGVID TPCWKLHTSP LCTTNTKEGS NICLTRTDRG WYCDNAGSVS FFPQAETCKV    360
QSNRVFCDTM NSLTLPSEVN LCNVDIFNPK YDCKIMTSKT DVSSSVITSL GAIVSCYGKT    420
KCTASNKNRG IIKTFSNGCD YVSNKGVDTV SVGNTLYYVN KQEGKSLYVK GEPIINFYDP    480
LVFPSDEFDA SISQVNEKIN QSLAFIRKSD ECCSAIGGYI PEAPRDGQAY VRKDGEWVLL    540
STFLGGLVPR GSHHHHHHSA WSHPQFEK                                       568

SEQ ID NO: 40            moltype = AA  length = 544
FEATURE                  Location/Qualifiers
REGION                   1..544
                         note = Peptide construct
source                   1..544
                         mol_type = protein
                         organism = synthetic construct
SEQUENCE: 40
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN    120
NAKKTNVTLS KKRKRRFLGF LLGVGSAIAS GVAVCKVLHL EGEVNKIKSA LLSTNKAVVS    180
LSNGVSVLTF KVLDLKNYID KQLLPILNKQ SCSISNIETV IEFQQKNNRL LEITREFSVN    240
AGVTTPVSTY MLTNSELLSL INDMPITNDQ KKLMSNNVQI VRQQSYSIMC IIKEEVLAYV    300
VQLPLYGVID TPCWKLHTSP LCTTNTKEGS NICLTRTDRG WYCDNAGSVS FFPQAETCKV    360
QSNRVFCDTM NSLTLPSEVN LCNVDIFNPK YDCKIMTSKT DVSSSVITSL GAIVSCYGKT    420
KCTASNKNRG IIKTFSNGCD YVSNKGVDTV SVGNTLYYVN KQEGKSLYVK GEPIINFYDP    480
LVFPSDEFDA SISQVNEKIN QSLACIRKSD ELLSAIGGYI PEAPRDGQAY VRKDGEWVLL    540
STFL                                                                 544

SEQ ID NO: 41            moltype = AA  length = 568
FEATURE                  Location/Qualifiers
REGION                   1..568
                         note = Peptide construct
source                   1..568
                         mol_type = protein
                         organism = synthetic construct
SEQUENCE: 41
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN    120
NAKKTNVTLS KKRKRRFLGF LLGVGSAIAS GVAVCKVLHL EGEVNKIKSA LLSTNKAVVS    180
LSNGVSVLTF KVLDLKNYID KQLLPILNKQ SCSISNIETV IEFQQKNNRL LEITREFSVN    240
AGVTTPVSTY MLTNSELLSL INDMPITNDQ KKLMSNNVQI VRQQSYSIMC IIKEEVLAYV    300
VQLPLYGVID TPCWKLHTSP LCTTNTKEGS NICLTRTDRG WYCDNAGSVS FFPQAETCKV    360
QSNRVFCDTM NSLTLPSEVN LCNVDIFNPK YDCKIMTSKT DVSSSVITSL GAIVSCYGKT    420
KCTASNKNRG IIKTFSNGCD YVSNKGVDTV SVGNTLYYVN KQEGKSLYVK GEPIINFYDP    480
LVFPSDEFDA SISQVNEKIN QSLACIRKSD ELLSAIGGYI PEAPRDGQAY VRKDGEWVLL    540
STFLGGLVPR GSHHHHHHSA WSHPQFEK                                       568
```

```
SEQ ID NO: 42           moltype = AA  length = 512
FEATURE                 Location/Qualifiers
REGION                  1..512
                        note = Peptide construct
source                  1..512
                        mol_type = protein
                        organism = synthetic construct
SEQUENCE: 42
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LSAIGGYIPE APRDGQAYVR KDGEWVLLST FL                                512

SEQ ID NO: 43           moltype = AA  length = 536
FEATURE                 Location/Qualifiers
REGION                  1..536
                        note = Peptide construct
source                  1..536
                        mol_type = protein
                        organism = synthetic construct
SEQUENCE: 43
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LSAIGGYIPE APRDGQAYVR KDGEWVLLST FLGGLVPRGS HHHHHHSAWS HPQFEK      536

SEQ ID NO: 44           moltype = AA  length = 477
FEATURE                 Location/Qualifiers
REGION                  1..477
                        note = Peptide construct
source                  1..477
                        mol_type = protein
                        organism = synthetic construct
SEQUENCE: 44
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMGGG SGGGSGGGSG SAIASGVAVC  120
KVLHLEGEVN KIKSALLSTN KAVVSLSNGV SVLTFKVLDL KNYIDKQLLP ILNKQSCSIS  180
NIETVIEFQQ KNNRLLEITR EFSVNAGVTT PVSTYMLTNS ELLSLINDMP ITNDQKKLMS  240
NNVQIVRQQS YSIMCIIKEE VLAYVVQLPL YGVIDTPCWK LHTSPLCTTN TKEGSNICLT  300
RTDRGWYCDN AGSVSFFPQA ETCKVQSNRV FCDTMNSLTL PSEVNLCNVD IFNPKYDCKI  360
MTSKTDVSSS VITSLGAIVS CYGKTKCTAS NKNRGIIKTF SNGCDYVSNK GVDTVSVGNT  420
LYYVNKQEGK SLYVKGEPII NFYDPLSAIG GYIPEAPRDG QAYVRKDGEW VLLSTFL     477

SEQ ID NO: 45           moltype = AA  length = 501
FEATURE                 Location/Qualifiers
REGION                  1..501
                        note = Peptide construct
source                  1..501
                        mol_type = protein
                        organism = synthetic construct
SEQUENCE: 45
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMGGG SGGGSGGGSG SAIASGVAVC  120
KVLHLEGEVN KIKSALLSTN KAVVSLSNGV SVLTFKVLDL KNYIDKQLLP ILNKQSCSIS  180
NIETVIEFQQ KNNRLLEITR EFSVNAGVTT PVSTYMLTNS ELLSLINDMP ITNDQKKLMS  240
NNVQIVRQQS YSIMCIIKEE VLAYVVQLPL YGVIDTPCWK LHTSPLCTTN TKEGSNICLT  300
RTDRGWYCDN AGSVSFFPQA ETCKVQSNRV FCDTMNSLTL PSEVNLCNVD IFNPKYDCKI  360
MTSKTDVSSS VITSLGAIVS CYGKTKCTAS NKNRGIIKTF SNGCDYVSNK GVDTVSVGNT  420
LYYVNKQEGK SLYVKGEPII NFYDPLSAIG GYIPEAPRDG QAYVRKDGEW VLLSTFLGGL  480
VPRGSHHHHH HSAWSHPQFE K                                            501

SEQ ID NO: 46           moltype = DNA  length = 25
FEATURE                 Location/Qualifiers
misc_feature            1..25
                        note = Primer
source                  1..25
                        mol_type = other DNA
                        organism = synthetic construct
SEQUENCE: 46
```

```
ctcaatttcc tcacttctcc agtgt                                              25

SEQ ID NO: 47          moltype = DNA  length = 24
FEATURE                Location/Qualifiers
misc_feature           1..24
                       note = Primer
source                 1..24
                       mol_type = other DNA
                       organism = synthetic construct
SEQUENCE: 47
cttgattcct cggtgtacct ctgt                                               24

SEQ ID NO: 48          moltype = DNA  length = 25
FEATURE                Location/Qualifiers
misc_feature           1..25
                       note = Primer
source                 1..25
                       mol_type = other DNA
                       organism = synthetic construct
SEQUENCE: 48
tcccattatg cctaggccag cagca                                              25

SEQ ID NO: 49          moltype = AA   length = 4
FEATURE                Location/Qualifiers
REGION                 1..4
                       note = Amino acid linker
source                 1..4
                       mol_type = protein
                       organism = synthetic construct
SEQUENCE: 49
GGGS                                                                      4
```

What is claimed is:

1. A recombinant respiratory syncytial virus (RSV) F protein trimer, comprising:
   an amino acid sequence set forth in SEQ ID NOs: 26 or 27 and a pharmaceutically acceptable excipient.

2. An RSV immunogenic composition comprising the recombinant RSV F trimer of claim 1, wherein the immunogenic composition formulated in an effective amount to produce an antigen-specific immune response directed against the recombinant RSV F trimer.

3. The immunogenic composition of claim 2, wherein the immunogenic composition is formulated with an adjuvant.

4. The immunogenic composition of claim 3, wherein the adjuvant is an aluminum adjuvant selected from amorphous aluminum hydroxyphosphate sulfate or an aqueous suspension of aluminum hydroxyphosphate.

5. The immunogenic composition of claim 3 formulated with a lipid nanoparticle comprising one or more cationic lipids and a poly(ethyleneglycol)-lipid (PEG lipid).

6. The immunogenic composition of claim 5, wherein the cationic lipids are selected from the group consisting of (2S)-1-({6-[(3))-cholest-5-en-3-yloxy]hexyl}oxy)-N,N-dimethyl-3-[(9 Z)-octadec-9-en-1-yloxy]propan-2-amine; (13Z,16Z)-N,N-dimethyl-3-nonyldocosa-13,16-dien-1-amine; and N,N-dimethyl-1-[(1S,2R)-2-octylcyclopropyl]heptadecan-8-amine; or a pharmaceutically acceptable salt thereof, or a stereoisomer of any of the foregoing.

7. The immunogenic composition of claim 5, which comprises 30-75 mole % ionizable cationic lipid and 0.1-20 mole % PEG-lipid.

8. The immunogenic composition of claim 3, wherein the adjuvant comprises one or more non-cationic lipids selected from a phospholipid, a phospholipid derivative, a fatty acid, a sterol, or a combination thereof, wherein the sterol is cholesterol, stigmasterol or stigmastanol;
   wherein the phospholipid is selected from phosphatidylserine, 1,2-Distearoyl-sn-glycero-3-phosphocholine (DSPC), 1,2-dipalmitoleoyl-sn-glycero-3-phosphocholine, 1,2-dimyristoyl-sn-glycero-3-phosphocholine (DMPC), dilauroylphosphatidylcholine (DLPC), 1,2-dieicosenoyl-sn-glycero-3-phosphocholine, and 1,2-dioleoyl-sn-glycero-3-phosphocholine (DOPC);
   wherein the PEG-lipid is 1,2-Dimyristoyl-sn-glycerol methoxypolyethylene glycol (PEG-DMG), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

9. A method of producing an immune response to RSV F in a subject, the method comprising administering to the subject an effective amount of the RSV F trimer of claim 1.

10. The RSV immunogenic composition of claim 2, wherein the amino acid sequence is set forth in SEQ ID NO: 26.

11. The RSV immunogenic composition of claim 2, wherein the amino acid sequence is set forth in SEQ ID NO: 27.

* * * * *

UNITED STATES PATENT AND TRADEMARK OFFICE
CERTIFICATE OF CORRECTION

| | | |
|---|---|---|
| PATENT NO. | : 12,234,265 B2 | Page 1 of 1 |
| APPLICATION NO. | : 18/068867 | |
| DATED | : February 25, 2025 | |
| INVENTOR(S) | : Lan Zhang et al. | |

It is certified that error appears in the above-identified patent and that said Letters Patent is hereby corrected as shown below:

In the Claims

In Column 81, Lines 50-51, please delete:
"consisting of (2S)-1-({6-[(3))-cholest-5-en-3-yloxy]hexyl}oxy)-N,N-dimethyl-3-[(9 Z)-octadec-9-en-1-yloxy]propan-2-amine;"

And replace with:
--- consisting of (2S)-1-({6-[(3β))-cholest-5-en-3-yloxy]hexyl}oxy)-N,N-dimethyl-3-[(9 Z)-octadec-9-en-1-yloxy]propan-2-amine; ---

Signed and Sealed this
Twenty-ninth Day of July, 2025

Coke Morgan Stewart
*Acting Director of the United States Patent and Trademark Office*